United States Patent [19]
Maynard et al.

[11] Patent Number: 5,932,571
[45] Date of Patent: Aug. 3, 1999

[54] SUBSTITUTED N-METHYL-N-(4-(4-(1H-BENZIMIDAZOL-2-YL) {1,4}DIAZEPAN-1-YL)-2-(ARYL) BUTYL) BENZAMIDES USEFUL FOR THE TREATMENT OF ALLERGIC DISEASES

[75] Inventors: George D. Maynard, Westbrook, Conn.; John M. Kane, Cincinnati, Ohio; Christopher R. Dalton, Mundelein, Ill.; Braulio Santiago, San Juan, Puerto Rico; Elizabeth M. Kudlacz, Groton, Conn.; Larry D. Bratton, Whitmore Lake, Mich.

[73] Assignee: Hoechst Marion Roussel, Inc., Bridgewater, N.J.

[21] Appl. No.: 09/036,155

[22] Filed: Mar. 6, 1998

Related U.S. Application Data

[63] Continuation-in-part of application No. 08/781,997, Jan. 6, 1997
[60] Provisional application No. 60/046,904, Feb. 21, 1996.
[51] Int. Cl.⁶ .......................... A61K 31/55; C07D 403/14
[52] U.S. Cl. .............................. 514/218; 540/575
[58] Field of Search .............................. 514/218; 540/575

[56] References Cited

U.S. PATENT DOCUMENTS

| | | | |
|---|---|---|---|
| 3,282,947 | 11/1966 | Grogan et al. | 260/293 |
| 3,862,173 | 1/1975 | Carr et al. | 260/240 R |
| 4,254,129 | 3/1981 | Carr et al. | 424/267 |
| 4,254,130 | 3/1981 | Carr et al. | 424/267 |
| 4,285,958 | 8/1981 | Carr et al. | 424/267 |
| 4,550,116 | 10/1985 | Soto et al. | 514/327 |
| 4,598,079 | 7/1986 | Beyerle et al. | 514/252 |
| 4,666,905 | 5/1987 | Downs et al. | 514/222 |
| 4,835,161 | 5/1989 | Janssens et al. | 514/303 |
| 4,908,372 | 3/1990 | Carr et al. | 514/322 |
| 4,960,776 | 10/1990 | Walsh et al. | 514/252 |
| 4,975,439 | 12/1990 | Van Daele et al. | 514/316 |
| 4,988,689 | 1/1991 | Janssens et al. | 514/212 |
| 5,010,078 | 4/1991 | Abou-Aharbia et al. | 514/252 |
| 5,023,256 | 6/1991 | Roberto et al. | 514/253 |
| 5,064,850 | 11/1991 | Audia | 514/406 |
| 5,166,136 | 11/1992 | Ward et al. | 514/15 |
| 5,182,399 | 1/1993 | Kane | 546/199 |
| 5,212,187 | 5/1993 | Alisch et al. | 514/342 |
| 5,214,040 | 5/1993 | Cuberes-Altisent et al. | 514/218 |
| 5,236,921 | 8/1993 | Emonds-Alt et al. | 514/252 |
| 5,272,150 | 12/1993 | Janssens et al. | 514/258 |
| 5,317,020 | 5/1994 | Emonds-Alt et al. | 514/255 |
| 5,322,850 | 6/1994 | Orjales-Venero et al. | 514/322 |
| 5,340,822 | 8/1994 | Emonds-Alt et al. | 514/254 |
| 5,371,093 | 12/1994 | Carr et al. | 514/321 |
| 5,411,971 | 5/1995 | Edmonds | 514/318 |
| 5,434,158 | 7/1995 | Shah | 514/278 |
| 5,534,525 | 7/1996 | Miller | 514/316 |
| 5,559,131 | 9/1996 | Miller | 514/329 |
| 5,635,509 | 6/1997 | Jacobs et al. | 514/274 |

FOREIGN PATENT DOCUMENTS

| | | |
|---|---|---|
| 1591692 | 5/1991 | Australia . |
| 1490995 | 9/1995 | Australia . |
| 0079545 | 5/1982 | European Pat. Off. . |
| 0145037 | 6/1985 | European Pat. Off. . |
| 0184257 | 6/1986 | European Pat. Off. . |
| 0282133 | 9/1988 | European Pat. Off. . |
| 0378254 | 7/1990 | European Pat. Off. . |
| 0428434 | 11/1990 | European Pat. Off. . |
| 0512902 | 5/1991 | European Pat. Off. . |
| 0482539 | 10/1991 | European Pat. Off. . |
| 0464927 | 1/1992 | European Pat. Off. . |
| 0533344 | 8/1992 | European Pat. Off. . |
| 0559538 | 3/1993 | European Pat. Off. . |
| 0625509 | 5/1994 | European Pat. Off. . |
| 0630887 | 5/1994 | European Pat. Off. . |
| 0517589 | 6/1991 | France . |
| 2601262 | 7/1976 | Germany . |
| 4297492 | 2/1991 | Jordan . |
| 9206086 | 10/1990 | WIPO . |
| 9222569 | 6/1991 | WIPO . |
| 9314113 | 1/1992 | WIPO . |
| 9201687 | 2/1992 | WIPO . |
| 9201697 | 2/1992 | WIPO . |
| 9300330 | 1/1993 | WIPO . |
| 9407495 | 4/1994 | WIPO . |
| 9426735 | 11/1994 | WIPO . |
| 9505377 | 2/1995 | WIPO . |
| 9508549 | 3/1995 | WIPO . |
| 9606094 | 2/1996 | WIPO . |
| 9610568 | 4/1996 | WIPO . |
| 9719074 | 5/1997 | WIPO . |

OTHER PUBLICATIONS

Barnes, et al., TIPS 11:185–189 (May 1990).
Ichinose, et al., The Lancet 340:1248–1251 (Nov.21, 1992).
Hagiwara, et al., "Studies on Neurokinin Antagonists 2.", Journal of Medicinal Chemistry, vol. 35, No. 17, 3184–3191, 1992.
Hagiwara, et al., Studies on Neurokinin Antagonists 1., J. Med. Chem, 35,2015–2025, 1992.

(List continued on next page.)

*Primary Examiner*—Mukund J. Shah
*Assistant Examiner*—Brenda Coleman
*Attorney, Agent, or Firm*—Barbara E. Kurys

[57] ABSTRACT

The present invention relates to novel N-methyl-N-(4-(4-(1H-benzimidazol-2-yl)[1,4]diazepan-1-yl)-2-(aryl)butyl) benzamide derivatives of the formula:

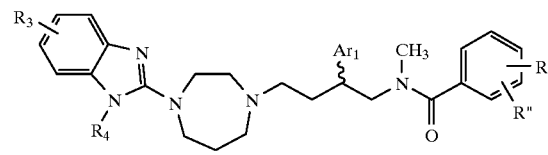

stereoisomers thereof, and pharmaceutically acceptable salts thereof which are useful as histamine receptor antagonists and tachykinin receptor antagonists. Such antagonists are useful in the treatment of allergic rhinitis, including seasonal rhinitis and sinusitis; inflammatory bowel diseases, including Crohn's disease and ulcerative colitis; asthma; bronchitis; and emesis.

19 Claims, No Drawings

OTHER PUBLICATIONS

Janssens, et al., J. Med. Chem. 28:1934–1943, (1985).
Janssens, et al., Drug Development Research 8:27–36, (1986).
Jansssens, et al., J. Med. Chem.,28(12):1925–1933, (1985).
Iemura, et al., Chem. Pharm. Bull., 37(4):967–972, (1989).
Janssens, et al., J. Med. Chem., 28(12):1943–1947, (1985).
Carr et al., The J. Organic Chem., 55(4):1399–1401, (1990).
Iemura, et al., Chem. Pharm. Bull., 37(4):962–966, (1989).
Maynard, Biorganic and Medicinal Chemistry Letters, vol. 3 (4), 753–756, 1993.
Wahlgren, J. Heterocyclic Chem., 26, 541–543, 1989.
Iemura, J. Heterocyclic Che., 24, 31–37, 1987.
Daijiro Hagiwara et. al., "Design of a Novel Dipeptide Substance P Antagonist FK888 and Its Pharmacological Profile", Fujisawa Pharmacetucial Co., Ltd. 1992.
Iemura, et al., J. Med. Chem., 29(7):1178–1183, (1986).
Hagiwara, et al., Studies on Neurokinin Antagonists 3., J. Med. Chem, 36, 2266–2278, 1993.
Emonds–Alt, et al., Life Sciences, 56(1):27–32, (1995).
Melloni, et al., Eur. J. Med. Chem., 26, 207–213 (1991).
Ward, et al., J. Med. Chem. 38, 4985–4992 (1995).
Armour, et al., Bioorganic & Med. Chem. Letters 6 (9), 1015–1020 (1996).

SUBSTITUTED N-METHYL-N-(4-(4-(1H-BENZIMIDAZOL-2-YL) {1,4}DIAZEPAN-1-YL)-2-(ARYL) BUTYL) BENZAMIDES USEFUL FOR THE TREATMENT OF ALLERGIC DISEASES

This application is a continuation-in-part of application Ser. No. 08/781,997, filed Jan. 6, 1997, which is hereby incorporated by reference, which claims the in benefit of U.S. Provisional Application Ser. No. 60/046,904, filed Feb. 21, 1996.

The present invention relates to novel substituted N-methyl-N-(4-(4-(1H-benzimidazol-2-yl)[1,4]diazepan-1-yl)-2-(aryl)butyl)benzamide derivatives (herein referred to as a compound or compounds of formula (1)) and their use as histamine receptor antagonists and tachykinin receptor antagonists. Such antagonists are useful in the treatment of asthma; bronchitis; inflammatory bowel diseases, including Crohn's disease and ulcerative colitis; allergic rhinitis, including seasonal rhinitis and sinusitis; allergies; and emesis.

The compounds of the present invention are useful in their pharmacological activities, such as histamine receptor antagonism and tachykinin receptor antagonism. Antagonism of histamine responses can be elicited through blocking of histamine receptors. Antagonism of tachykinin responses can be elicited through blocking of tachykinin receptors. One object of the present invention is to provide new and useful antagonists of histamine. A further object of the present invention is to provide new and useful antagonists of tachykinins. A particular object of the present invention are those compounds that exhibit both histamine and tachykinin receptor antagonism.

SUMMARY OF THE INVENTION

The present invention provides novel substituted N-methyl-N-(4-(4-(1H-benzimidazol-2-yl)[1,4]diazepan-1-yl)-2-(aryl)butyl)benzamide derivatives of the formula:

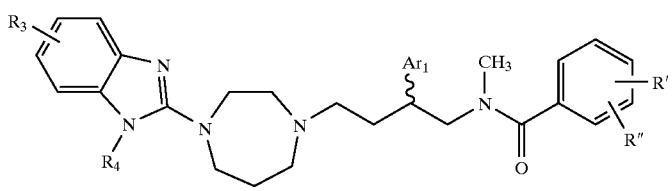

formula (1)

wherein
R' is from 1 to 3 substituents each independently chosen from the group consisting of hydrogen, halogen, —OCF$_3$, C$_1$–C$_6$ alkyl, and C$_1$–C$_6$ alkoxy;
R" is hydrogen or a radical chosen from the group consisting of

wherein
R$_{20}$ is selected from the group consisting of hydrogen, C$_1$–C$_4$ alkyl, and —CF$_3$;

R$_3$ is from 1 to 3 substituents each independently chosen from the group consisting of hydrogen, halogen, C$_1$–C$_6$ alkyl, and C$_1$–C$_6$ alkoxy;
Ar$_1$ is a radical chosen from the group consisting of

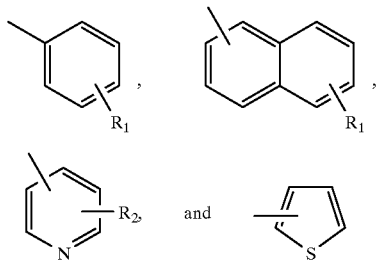

wherein
R$_1$ is from 1 to 3 substituents each independently chosen from the group consisting of hydrogen, halogen, hydroxy, CF$_3$, C$_1$–C$_6$ alkyl, and C$_1$–C$_6$ alkoxy;
R$_2$ is from 1 to 2 substituents each independently chosen from the group consisting of hydrogen, halogen, C$_1$–C$_6$ alkyl, and C$_1$–C$_6$ alkoxy;
R$_4$ is chosen from the group consisting of hydrogen, C$_1$–C$_6$ alkyl, —(CH$_2$)$_w$—O—(CH$_2$)$_t$CO$_2$R$_8$, —(CH$_2$)$_j$CN, —(CH$_2$)$_u$CO$_2$R$_6$, —(CH$_2$)$_u$C(O)NR$_{16}$R$_{17}$, —(CH$_2$)$_p$Ar$_2$, —(CH$_2$)$_w$—O—R$_7$, —CH$_2$CF$_3$, —CH$_2$CH$_2$CH$_2$CF$_3$, —(CH$_2$)$_2$CH=CH$_2$, —CH$_2$CH=CH$_2$, —CH$_2$CH=CHCH$_3$, —CH$_2$CH=CHCH$_2$CH$_3$, —CH$_2$CH=C(CH$_3$)$_2$, and —(CH$_2$)$_g$S(O)$_k$R$_{19}$,
wherein
w is an integer from 2 to 5;
t is an integer from 1 to 3;
j is an integer from 1 to 5;
u is an integer from 1 to 5;
p is 1 or 2;
g is 2 or 3;
k is an integer from 0, 1, or 2;
R$_6$ is hydrogen or C$_1$–C$_4$ alkyl;
R$_7$ is hydrogen, C$_1$–C$_4$ alkyl, —(CH$_2$)$_y$—CF$_3$, —CH$_2$CN or a radical chosen from the group consisting of

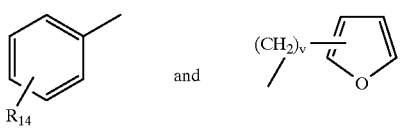

wherein
v is an integer from 1 to 3;
y is an integer from 0 to 2;

$R_{14}$ is chosen from the group consisting of hydrogen, halogen, $C_1$–$C_4$ alkyl, and —$CO_2R_{15}$ wherein $R_{15}$ is hydrogen or $C_1$–$C_4$ alkyl;

$R_8$ is hydrogen or $C_1$–$C_4$ alkyl;

$R_{16}$ is hydrogen or $C_1$–$C_4$ alkyl;

$R_{17}$ is hydrogen or $C_1$–$C_4$ alkyl;

$Ar_2$ is a radical chosen from the group consisting of

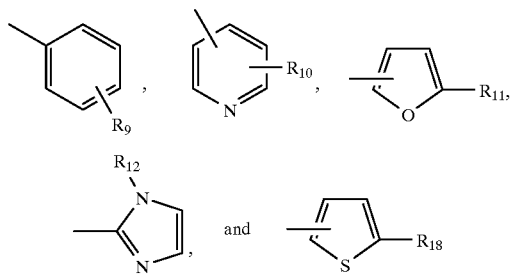

wherein $R_9$ is from 1 to 3 substituents each independently chosen from the group consisting of hydrogen, halogen, $CF_3$, $C_1$–$C_6$ alkyl, $C_1$–$C_6$ alkoxy, and —$CO_2R_{13}$ wherein $R_{13}$ is chosen from the group consisting of hydrogen and $C_1$–$C_4$ alkyl;

$R_{10}$ is from 1 to 2 substituents each independently chosen from the group consisting of hydrogen, halogen, $C_1$–$C_6$ alkyl, and $C_1$–$C_6$ alkoxy;

$R_{11}$ is chosen from the group consisting of hydrogen, —$CH_3$, and —$CH_2OH$;

$R_{12}$ is chosen from the group consisting of hydrogen, $C_1$–$C_4$ alkyl, and benzyl;

$R_{18}$ is chosen from the group consisting of hydrogen, halogen, —$CH_3$, and —$CH_2OH$;

$R_{19}$ is $C_1$–$C_4$ alkyl or a radical of the formula

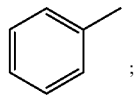

and stereoisomers, and pharmaceutically acceptable salts thereof.

As is appreciated by one of ordinary skill in the art the N-methyl-N-(4-(4-(1H-benzimidazol-2-yl)[1,4]diazepan-1-yl)-2-(aryl)butyl)benzamides of formula (1) exist as stereoisomers. Specifically, it is recognized that the present N-methyl-N-(4-(4-(1H-benzimidazol-2-yl)[1,4]diazepan-1-yl)-2-(aryl)butyl)benzamides exist as stereoisomers at the 2-position of the butyl, that is, at the point of attachment of the aryl substituent. Any reference in this application to one of the compounds of the formula (1) is meant to encompass either specific stereoisomers or a mixture of stereoisomers.

The specific stereoisomers can be prepared by stereospecific synthesis using enantiomerically pure or enantiomerically enriched starting materials. The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are known in the art and described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As used in this application:

a) the term "halogen" refers to a fluorine atom, chlorine atom, bromine atom, or iodine atom;

b) the term "$C_1$–$C_6$ alkyl" refers to a branched or straight chained alkyl radical containing from 1 to 6 carbon atoms, such as methyl, ethyl, n-propyl, isopropyl, n-butyl, isobutyl, t-butyl, pentyl, hexyl, cyclopentyl, cyclohexyl, etc.;

c) the term "$C_1$–$C_6$ alkoxy" refers to a straight or branched alkoxy group containing from 1 to 6 carbon atoms, such as methoxy, ethoxy, n-propoxy, isopropoxy, n-butoxy, isobutoxy, t-butoxy, pentoxy, hexoxy, cyclopentoxy, cyclohexoxy, etc.;

d) the designations —C(O)— or —(O)C— refer to a carbonyl group of the formula:

e) the designation "⁓" refers to a bond for which the stereochemistry is not designated;

f) as used in the examples and preparations, the following terms have the meanings indicated: "kg" refers to kilograms, "g" refers to grams, "mg" refers to milligrams, "µg" refers to micrograms, "mol" refers to moles, "mmol" refers to millimoles, "nmole" refers to nanomoles, "L" refers to liters, "mL" or "ml" refers to milliliters, "µL" refers to microliters, "°C." refers to degrees Celsius, "$R_f$" refers to retention factor, "mp" refers to melting point, "dec" refers to decomposition, "bp" refers to boiling point, "mm of Hg" refers to pressure in millimeters of mercury, "cm" refers to centimeters, "nm" refers to nanometers, "$[a]_D^{20}$" refers to specific rotation of the D line of sodium at 20° C. obtained in a 1 decimeter cell, "c" refers to concentration in g/mL, "THF" refers to tetrahydrofuran, "DMF" refers to dimethylformamide, "brine" refers to a saturated aqueous sodium chloride solution, "M" refers to molar, "mM" refers to millimolar, "µM" refers to micromolar, "nM" refers to nanomolar, "psi" refers to pounds per square inch, "TLC" refers to thin layer chromatography, "HPLC" refers to high performance liquid chromatography, "HRMS" refers to high resolution mass spectrum, "µCi" refers to microcuries, "i.p." refers to intraperitoneally, "i.v." refers to intravenously, and "DPM" refers to disintegrations per minute;

g) the designation

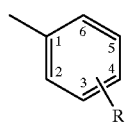

refers to a phenyl or a substituted phenyl and it is understood that the radical is attached at the 1-position and the substituent or substituents represented by R can be attached in any of the 2, 3, 4, 5, or 6 positions;

h) the designation

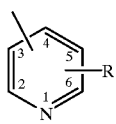

refers to a pyridine, substituted pyridine, pyridyl or substituted pyridyl and it is understood that the radical can be attached at either the 2-position, the 3-position, or the 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

i) the designation

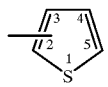

refers to a thiophene or thienyl and it is understood that the radical is attached at the 2 or 3-positions;

j) the designation

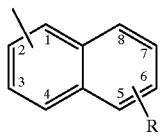

refers to a naphthalene, substituted naphthalene, naphthyl or substituted naphthyl and it is understood that the radical can be attached at either the 1-position or the 2-position, it is further understood that when the radical is attached at the 1-position the substituent or substituents represented by R can be attached in any of the 2, 3, 4, 5, 6, 7, or 8 positions and that when the radical is attached at the 2-position the substituent or substituents represented by R can be attached in any of the 1, 3, 4, 5, 6, 7, or 8 positions;

k) the term "enantiomeric excess" or "ee" refers to the percent by which one enantiomer, E1, is in excess in a mixture of the two enantiomers, E1 plus E2, such that {(E1-E2)-(E1+E2)}×100%=ee, with the designation "(+)–" refers to the plus enantiomer, "(–)–" refers to the minus enantiomer;

l) the term "$C_1$–$C_4$ alkyl" refers to a saturated straight or branched chain alkyl group containing from 1–4 carbon atoms and includes methyl, ethyl, propyl, isopropyl, n-butyl, s-butyl, isobutyl, and t-butyl;

m) the designations —$CO_2$R and —C(O)OR refer to a group of the formula:

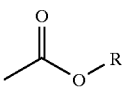

n) the designation —C(O)NRR refers to a group of the formula:

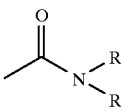

o) the designation

refers to a furan or furyl and it is understood that the radical is attached at either the 2-position or 3-position;

p) the term "pharmaceutically acceptable salts thereof" refers to either an acid addition salt or a basic addition salt;

q) the designation "◄■" refers to a bond that protrudes forward out of the plane of the page;

r) the designation "⋯⋯⋯" refers to a bond that protrudes backward out of the plane of the page.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

Preferred embodiments of formula (1) are given below:

Compounds wherein $R_4$ is —$(CH_2)_w$—O—$R_7$ are preferred;

Compounds wherein $R_4$ is —$(CH_2)_w$—O—$R_7$ and w is 2 are more preferred;

Compounds wherein $R_4$ is —$(CH_2)_p Ar_2$ are preferred;

Compounds wherein $R_4$ is —$(CH_2)_p Ar_2$ wherein p is 1 are more preferred;

Compounds wherein $R_4$ is —$(CH_2)_p Ar_2$ wherein p is 1 and $Ar_2$ is 4-fluorophenyl, fur-2-yl, fur-3-yl, 5-hydroxymethylfur-2-yl, or pyrid-2-yl are most preferred;

Compounds wherein $R_4$ is —$CH_2CH=CHCH_3$ are preferred.

Examples of compounds encompassed by the present invention include the following. It is understood that the examples encompass both the (+)-isomer and the (−)-isomer of the compound and mixtures thereof. This list is meant to be representative only and is not intended to limit the scope of the invention in any way:

N-Methyl-N-(4-(4-(1-(5-hydroxymethylfur-2-ylmethyl)-1H-benzimidazol-2-yl)[1,4]diazepan-1-yl)-2-phenylbutyl)benzamide;

N-Methyl-N-(4-(4-(1-(5-hydroxymethylfur-2-ylmethyl)-1H-benzimidazol-2-yl)[1,4]diazepan-1-yl)-2-phenylbutyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(4-fluorophenyl)butyl)benzamide;

N-Methyl-N-(4-(4-(1-(5-hydroxymethylfur-2-ylmethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(3,4-difluorophenyl)butyl)benzamide;

N-Methyl-N-(4-(4-(1-(5-hydroxymethylfur-2-ylmethyl)-1H-benzimidazol-2-yl)[1,4]diazepan-1-yl)-2-(3,4-difluorophenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(3-chlorophenyl)butyl)benzamide;

N-Methyl-N-(4-(4-(1-(5-hydroxymethylfur-2-ylmethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(4-chlorophenyl)butyl)benzamide;

N-Methyl-N-(4-(4-(1-(5-hydroxymethylfur-2-ylmethyl)-1H-benzimidazol-2-yl)[1,4]diazepan-1-yl)-2-(4-chlorophenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(3,4-dichlorophenyl)butyl)benzamide;

N-Methyl-N-(4-(4-(1-(5-hydroxymethylfur-2-ylmethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(3,4-dichlorophenyl)butyl)-3,5-bis(trifluoromethyl)benzamide;

N-Methyl-N-(4-(4-(1-(5-hydroxymethylfur-2-ylmethyl)-1H-benzimidazol-2-yl)[1,4]diazepan-1-yl)-2-(3,4-dichlorophenyl)butyl)-4-chlorobenzamide;

N-Methyl-N-(4-(4-(1-(5-hydroxymethylfur-2-ylmethyl)-1H-benzimidazol-2-yl)[1,4]diazepan-1-yl)-2-(3,4-dichlorophenyl)butyl)-4-methylbenzamide;

N-Methyl-N-(4-(4-(1-(5-hydroxymethylfur-2-ylmethyl)-1H-benzimidazol-2-yl)[1,4]diazepan-1-yl)-2-(3,4-dichlorophenyl)butyl)-4-t-butylbenzamide;

N-Methyl-N-(4-(4-(1-(5-hydroxymethylfur-2-ylmethyl)-1H-benzimidazol-2-yl)[1,4]diazepan-1-yl)-2-(3,4-dichlorophenyl)butyl)-2,4-dimethoxybenzamide;

N-Methyl-N-(4-(4-(1-(5-hydroxymethylfur-2-ylmethyl)-1H-benzimidazol-2-yl)[1,4]diazepan-1-yl)-2-(4-methoxyphenyl)butyl)benzamide;

N-Methyl-N-(4-(4-(1-(5-hydroxymethylfur-2-ylmethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(3-methoxyphenyl)butyl)benzamide;

N-Methyl-N-(4-(4-(1-(5-hydroxymethylfur-2-ylmethyl)-1H-benzimidazol-2-yl)[1,4]diazepan-1-yl)-2-(3-methoxyphenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(3,4-dimethoxyphenyl)butyl)benzamide;

N-Methyl-N-(4-(4-(1-(5-hydroxymethylfur-2-ylmethyl)-1H-benzimidazol-2-yl)[1,4]diazepan-1-yl)-2-(3,4-dimethoxyphenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(benzo[1,3]dioxol-5-yl)butyl)benzamide;

N-Methyl-N-(4-(4-(1-(5-hydroxymethylfur-2-ylmethyl)-1H-benzimidazol-2-yl)[1,4]diazepan-1-yl)-2-(benzo[1,3]dioxol-5-yl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(naphth-2-yl)butyl)benzamide;

N-Methyl-N-(4-(4-(1-(5-hydroxymethylfur-2-ylmethyl)-1H-benzimidazol-2-yl)[1,4]diazepan-1-yl)-2-(3-trifluoromethylphenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(4-trifluoromethylphenyl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(thien-2-yl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(pyrid-2-yl)butyl)benzamide;

N-Methyl-N-(4-(4-(1-(5-hydroxymethylfur-2-ylmethyl)-1H-benzimidazol-2-yl)[1,4]diazepan-1-yl)-2-(pyrid-2-yl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(pyrid-3-yl)butyl)benzamide;

N-Methyl-N-(4-(4-(1-(5-hydroxymethylfur-2-ylmethyl)-1H-benzimidazol-2-yl)[1,4]diazepan-1-yl)-2-(pyrid-3-yl)butyl)-3,4,5-trimethoxybenzamnide;

N-Methyl-N-(4-(4-(1-(5-hydroxymethylfur-2-ylmethyl)-1H-benzimidazol-2-yl)[1,4]diazepan-1-yl)-2-(pyrid-4-yl)butyl)-3,4,5-trimethoxybenzamide;

N-Methyl-N-(4-(4-(1-(5-hydroxymethylfur-2-ylmethyl)-1H-benzimidazol-2-yl)[1,4]diazepan-1-yl)-2-(pyrid-4-yl)butyl)benzamide;

N-Methyl-N-(4-(4-(1-(5-hydroxymethylfur-2-ylmethyl)-1H-benzimidazol-2-yl)[1,4]diazepan-1-yl)-2-(3,4-dimethylphenyl)butyl)-3,4,5-trimethoxybenzamide;

N-Methyl-N-(4-(4-(1H-benzimidazol-2-yl)[1,4]diazepan-1-yl)-2-phenylbutyl)benzamide;

N-Methyl-N-(4-(4-(1H-benzimidazol-2-yl)[1,4]diazepan-1-yl)-2-phenylbutyl)-3,4,5-trimethoxybenzamide;

N-Methyl-N-(4-(4-(1H-benzimidazol-2-yl)[1,4]diazepan-1-yl)-2-(4-fluorophenyl)butyl)benzamide;

N-Methyl-N-(4-(4-(1H-benzimidazol-2-yl)[1,4]diazepan-1-yl)-2-(4-fluorophenyl)butyl)-3,4,5-trimethoxybenzamide;

N-Methyl-N-(4-(4-(1H-benzimidazol-2-yl)[1,4]diazepan-1-yl)-2-(3,4-difluorophenyl)butyl)benzamide;
N-Methyl-N-(4-(4-(1H-benzimidazol-2-yl)[1,4]diazepan-1-yl)-2-(3,4-difluorophenyl)butyl)-3,4,5-trimethoxybenzamide;
N-Methyl-N-(4-(4-(1H-benzimidazol-2-yl)[1,4]diazepan-1-yl)-2-(3-chlorophenyl)butyl)benzamide;
N-Methyl-N-(4-(4-(1H-benzimidazol-2-yl)[1,4]diazepan-1-yl)-2-(3-chlorophenyl)butyl)-3,4,5-trimethoxybenzamide;
N-Methyl-N-(4-(4-(1H-benzimidazol-2-yl)[1,4]diazepan-1-yl)-2-(4-chlorophenyl)butyl)benzamide;
N-Methyl-N-(4-(4-(1H-benzimidazol-2-yl)[1,4]diazepan-1-yl)-2-(4-chlorophenyl)butyl)-3,4,5-trimethoxybenzamide;
N-Methyl-N-(4-(4-(1H-benzimidazol-2-yl)[1,4]diazepan-1-yl)-2-(3,4-dichlorophenyl)butyl)benzamide;
N-Methyl-N-(4-(4-(1H-benzimidazol-2-yl)[1,4]diazepan-1-yl)-2-(3,4-dichlorophenyl)butyl)-3,4,5-trimethoxybenzamide;
N-Methyl-N-(4-(4-(1H-benzimidazol-2-yl)[1,4]diazepan-1-yl)-2-(3,4-dichlorophenyl)butyl)-3,5-bis(trifluoromethyl)benzamide;
N-Methyl-N-(4-(4-(1H-benzimidazol-2-yl)[1,4]diazepan-1-yl)-2-(3,4-dichlorophenyl)butyl)-4-chlorobenzamide;
N-Methyl-N-(4-(4-(1H-benzimidazol-2-yl)[1,4]diazepan-1-yl)-2-(3,4-dichlorophenyl)butyl)-4-methylbenzamide;
N-Methyl-N-(4-(4-(1H-benzimidazol-2-yl)[1,4]diazepan-1-yl)-2-(3,4-dichlorophenyl)butyl)-4-t-butylbenzamide;
N-Methyl-N-(4-(4-(1H-benzimidazol-2-yl)[1,4]diazepan-1-yl)-2-(3,4-dichlorophenyl)butyl)-2,4-dimethoxybenzamide;
N-Methyl-N-(4-(4-(1H-benzimidazol-2-yl)[1,4]diazepan-1-yl)-2-(4-methoxyphenyl)butyl)benzamide;
N-Methyl-N-(4-(4-(1H-benzimidazol-2-yl)[1,4]diazepan-1-yl)-2-(4-methoxyphenyl)butyl)-3,4,5-trimethoxybenzamide;
N-Methyl-N-(4-(4-(1H-benzimidazol-2-yl)[1,4]diazepan-1-yl)-2-(3-methoxyphenyl)butyl)benzamide;
N-Methyl-N-(4-(4-(1H-benzimidazol-2-yl)[1,4]diazepan-1-yl)-2-(3-methoxyphenyl)butyl)-3,4,5-trimethoxybenzamide;
N-Methyl-N-(4-(4-(1H-benzimidazol-2-yl)[1,4]diazepan-1-yl)-2-(3,4-dimethoxyphenyl)butyl)benzamide;
N-Methyl-N-(4-(4-(1H-benzimidazol-2-yl)[1,4]diazepan-1-yl)-2-(3,4-dimethoxyphenyl)butyl)-3,4,5-trimethoxybenzamide;
N-Methyl-N-(4-(4-(1H-benzimidazol-2-yl)[1,4]diazepan-1-yl)-2-(benzo[1,3]dioxol-5-yl)butyl)benzamide;
N-Methyl-N-(4-(4-(1H-benzimidazol-2-yl)[1,4]diazepan-1-yl)-2-(benzo[1,3]dioxol-5-yl)butyl)-3,4,5-trimethoxybenzamide;
N-Methyl-N-(4-(4-(1H-benzimidazol-2-yl)[1,4]diazepan-1-yl)-2-(naphth-2-yl)butyl)benzamide;
N-Methyl-N-(4-(4-(1H-benzimidazol-2-yl)[1,4]diazepan-1-yl)-2-(3-trifluoromethylphenyl)butyl)-3,4,5-trimethoxybenzamide;
N-Methyl-N-(4-(4-(1H-benzimidazol-2-yl)[1,4]diazepan-1-yl)-2-(4-trifluoromethylphenyl)butyl)-3,4,5-trimethoxybenzamide;
N-Methyl-N-(4-(4-(1H-benzimidazol-2-yl)[1,4]diazepan-1-yl)-2-(thien-2-yl)butyl)-3,4,5-trimethoxybenzamide;
N-Methyl-N-(4-(4-(1H-benzimidazol-2-yl)[1,4]diazepan-1-yl)-2-(pyrid-2-yl)butyl)benzamide;
N-Methyl-N-(4-(4-(1H-benzimidazol-2-yl)[1,4]diazepan-1-yl)-2-(pyrid-2-yl)butyl)-3,4,5-trimethoxybenzamide;
N-Methyl-N-(4-(4-(1H-benzimidazol-2-yl)[1,4]diazepan-1-yl)-2-(pyrid-3-yl)butyl)benzamide;
N-Methyl-N-(4-(4-(1H-benzimidazol-2-yl)[1,4]diazepan-1-yl)-2-(pyrid-3-yl)butyl)-3,4,5-trimethoxybenzamide;
N-Methyl-N-(4-(4-(1H-benzimidazol-2-yl)[1,4]diazepan-1-yl)-2-(pyrid-4-yl)butyl)-3,4,5-trimethoxybenzamide;
N-Methyl-N-(4-(4-(1H-benzimidazol-2-yl)[1,4]diazepan-1-yl)-2-(pyrid-4-yl)butyl)benzamide;
N-Methyl-N-(4-(4-(1H-benzimidazol-2-yl)[1,4]diazepan-1-yl)-2-(3,4-dimethylphenyl)butyl)-3,4,5-trimethoxybenzamide;
N-Methyl-N-(4-(4-(1-(2-ethoxyethyl)-1H-benzimidazol-2-yl)[1,4]diazepan-1-yl)-2-phenylbutyl)benzamide;
N-Methyl-N-(4-(4-(1-(2-ethoxyethyl)-1H-benzimidazol-2-yl)[1,4]diazepan-1-yl)-2-phenylbutyl)-3,4,5-trimethoxybenzamide;
N-Methyl-N-(4-(4-(1-(2-ethoxyethyl)-1H-benzimidazol-2-yl)[1,4]diazepan-1-yl)-2-(4-fluorophenyl)butyl)benzamide;
N-Methyl-N-(4-(4-(1-(2-ethoxyethyl)-1H-benzimidazol-2-yl)[1,4]diazepan-1-yl)-2-(4-fluorophenyl)butyl)-3,4,5-trimethoxybenzamide;
N-Methyl-N-(4-(4-(1-(2-ethoxyethyl)-1H-benzimidazol-2-yl)[1,4]diazepan-1-yl)-2-(3,4-difluorophenyl)butyl)benzamide;
N-Methyl-N-(4-(4-(1-(2-ethoxyethyl)-1H-benzimidazol-2-yl)[1,4]diazepan-1-yl)-2-(3,4-difluorophenyl)butyl)-3,4,5-trimethoxybenzamide;
N-Methyl-N-(4-(4-(1-(2-ethoxyethyl)-1H-benzimidazol-2-yl)[1,4]diazepan-1-yl)-2-(3-chlorophenyl)butyl)benzamide;
N-Methyl-N-(4-(4-(1-(2-ethoxyethyl)-1H-benzimidazol-2-yl)[1,4]diazepan-1-yl)-2-(3-chlorophenyl)butyl)-3,4,5-trimethoxybenzamide;
N-Methyl-N-(4-(4-(1-(2-ethoxyethyl)-1H-benzimidazol-2-yl)[1,4]diazepan-1-yl)-2-(4-chlorophenyl)butyl)benzamide;
N-Methyl-N-(4-(4-(1-(2-ethoxyethyl)-1H-benzimidazol-2-yl)[1,4]diazepan-1-yl)-2-(4-chlorophenyl)butyl)-3,4,5-trimethoxybenzamide;
N-Methyl-N-(4-(4-(1-(2-ethoxyethyl)-1H-benzimidazol-2-yl)[1,4]diazepan-1-yl)-2-(3,4-dichlorophenyl)butyl)benzamide;
N-Methyl-N-(4-(4-(1-(2-ethoxyethyl)-1H-benzimidazol-2-yl)[1,4]diazepan-1-yl)-2-(3,4-dichlorophenyl)butyl)-3,4,5-trimethoxybenzamide;
N-Methyl-N-(4-(4-(1-(2-ethoxyethyl)-1H-benzimidazol-2-yl)[1,4]diazepan-1-yl)-2-(3,4-dichlorophenyl)butyl)-3,5-bis(trifluoromethyl)benzamide;
N-Methyl-N-(4-(4-(1-(2-ethoxyethyl)-1H-benzimidazol-2-yl)[1,4]diazepan-1-yl)-2-(3,4-dichlorophenyl)butyl)-4-chlorobenzamide;
N-Methyl-N-(4-(4-(1-(2-ethoxyethyl)-1H-benzimidazol-2-yl)[1,4]diazepan-1-yl)-2-(3,4-dichlorophenyl)butyl)-4-methylbenzamide;
N-Methyl-N-(4-(4-(1-(2-ethoxyethyl)-1H-benzimidazol-2-yl)[1,4]diazepan-1-yl)-2-(3,4-dichlorophenyl)butyl)-4-t-butylbenzamide;
N-Methyl-N-(4-(4-(1-(2-ethoxyethyl)-1H-benzimidazol-2-yl)[1,4]diazepan-1-yl)-2-(3,4-dichlorophenyl)butyl)-2,4-dimethoxybenzamide;
N-Methyl-N-(4-(4-(1-(2-ethoxyethyl)-1H-benzimidazol-2-yl)[1,4]diazepan-1-yl)-2-(4-methoxyphenyl)butyl)benzamide;
N-Methyl-N-(4-(4-(1-(2-ethoxyethyl)-1H-benzimidazol-2-yl)[1,4]diazepan-1-yl)-2-(4-methoxyphenyl)butyl)-3,4,5-trimethoxybenzamide;
N-Methyl-N-(4-(4-(1-(2-ethoxyethyl)-1H-benzimidazol-2-yl)[1,4]diazepan-1-yl)-2-(3-methoxyphenyl)butyl)benzamide;

N-Methyl-N-(4-(4-(1-(2-ethoxyethyl)-1H-benzimidazol-2-yl)[1,4]diazepan-1-yl)-2-(3-methoxyphenyl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(3,4-dimethoxyphenyl)butyl) benzamide;

N-Methyl-N-(4-(4-(1-(2-ethoxyethyl)-1H-benzimidazol-2-yl)[1,4]diazepan-1-yl)-2-(3,4-dimethoxyphenyl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(benzo[1,3]dioxol-5-yl)butyl) benzamide;

N-Methyl-N-(4-(4-(1-(2-ethoxyethyl)-1H-benzimidazol-2-yl)[1,4]diazepan-1-yl)-2-(benzo[1,3]dioxol-5-yl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(naphth-2-yl)butyl)benzamide;

N-Methyl-N-(4-(4-(1-(2-ethoxyethyl)-1H-benzimidazol-2-yl)[1,4]diazepan-1-yl)-2-(3-trifluoromethylphenyl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(4-trifluoromethylphenyl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(thien-2-yl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(pyrid-2-yl)butyl)benzamide;

N-Methyl-N-(4-(4-(1-(2-ethoxyethyl)-1H-benzimidazol-2-yl)[1,4]diazepan-1-yl)-2-(pyrid-2-yl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(pyrid-3-yl)butyl)benzamide;

N-Methyl-N-(4-(4-(1-(2-ethoxyethyl)-1H-benzimidazol-2-yl)[1,4]diazepan-1-yl)-2-(pyrid-3-yl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(pyrid-4-yl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(pyrid-4-yl)butyl)benzamide;

N-Methyl-N-(4-(4-(1-(2-ethoxyethyl)-1H-benzimidazol-2-yl)[1,4]diazepan-1-yl)-2-(3,4-dimethylphenyl)butyl)-3,4,5-trimethoxybenzamide;

N-Methyl-N-(4-(4-(1-(2-ethoxyethyl)-1H-benzimidazol-2-yl)[1,4]diazepan-1-yl)-2-(4-fluorophenyl)butyl)-5-trifluoromethoxy-2-methoxybenzamide;

N-Methyl-N-(4-(4-(1-(2-ethoxyethyl)-1H-benzimidazol-2-yl)[1,4]diazepan-1-yl)-2-(4-fluorophenyl)butyl)-2-methoxy-5-(1H-tetrazol-1-yl)benzamide;

N-Methyl-N-(4-(4-(1-(2-ethoxyethyl)-1H-benzimidazol-2-yl)[1,4]diazepan-1-yl)-2-(4-fluorophenyl)butyl)-2-methoxy-5-(4H-triazol-4-yl)benzamide;

N-Methyl-N-(4-(4-(1-(2-ethoxyethyl)-1H-benzimidazol-2-yl)[1,4]diazepan-1-yl)-2-(3,4-dichlorophenyl)butyl)-2-methoxy-5-(1H-tetrazol-1-yl)benzamide;

N-Methyl-N-(4-(4-(1-(2-ethoxyethyl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(N-methylacetamido)-1H-benzimidazol-2-yl)[1,4]diazepan-1-yl)-2-phenylbutyl)benzamide;

N-Methyl-N-(4-(4-(1-(N,N-dimethylacetamido)-1H-benzimidazol-2-yl)[1,4]diazepan-1-yl)-2-phenylbutyl)-3,4,5-trimethoxybenzamide;

N-Methyl-N-(4-(4-(1-(acetamido)-1H-benzimidazol-2-yl)[1,4]diazepan-1-yl)-2-(4-fluorophenyl)butyl)benzamide;

N-Methyl-N-(4-(4-(1-(N-methylacetamido)-1H-benzimidazol-2-yl)[1,4]diazepan-1-yl)-2-(4-fluorophenyl)butyl)-3,4,5-trimethoxybenzamide;

N-Methyl-N-(4-(4-(1-(N,N-dimethylacetamido)-1H-benzimidazol-2-yl)[1,4]diazepan-1-yl)-2-(3-chlorophenyl)butyl)benzamide;

N-Methyl-N-(4-(4-(1-(N-methylacetamido)-1H-benzimidazol-2-yl)[1,4]diazepan-1-yl)-2-(3-chlorophenyl)butyl)-3,4,5-trimethoxybenzamide;

N-Methyl-N-(4-(4-(1-(acetamido)-1H-benzimidazol-2-yl)[1,4]diazepan-1-yl)-2-(3,4-dichlorophenyl)butyl)benzamide;

N-Methyl-N-(4-(4-(1-(N-methylacetamido)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(N-methylacetamido)-1H-benzimidazol-2-yl)[1,4]diazepan-1-yl)-2-(4-methoxyphenyl)butyl)benzamide;

N-Methyl-N-(4-(4-(1-(N,N-dimethylacetamido)-1H-benzimidazol-2-yl)[1,4]diazepan-1-yl)-2-(4-methoxyphenyl)butyl)-3,4,5-trimethoxybenzamide;

N-Methyl-N-(4-(4-(1-(pyrid-2-ylmethyl)-1H-benzimidazol-2-yl)[1,4]diazepan-1-yl)-2-phenylbutyl)benzamide;

N-Methyl-N-(4-(4-(1-(pyrid-2-ylmethyl)-1H-benzimidazol-2-yl)[1,4]diazepan-1-yl)-2-phenylbutyl)-3,4,5-trimethoxybenzamide;

N-Methyl-N-(4-(4-(1-(pyrid-2-ylmethyl)-1H-benzimidazol-2-yl)[1,4]diazepan-1-yl)-2-(4-fluorophenyl)butyl)benzamide;

N-Methyl-N-(4-(4-(1-(pyrid-2-ylmethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(pyrid-2-ylmethyl)-1H-benzimidazol-2-yl)[1,4]diazepan-1-yl)-2-(3-chlorophenyl)butyl)benzamide;

N-Methyl-N-(4-(4-(1-(pyrid-2-ylmethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(pyrid-2-ylmethyl)-1H-benzimidazol-2-yl)[1,4]diazepan-1-yl)-2-(3,4-dichlorophenyl)butyl)benzamide;

N-Methyl-N-(4-(4-(1-(pyrid-2-ylmethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(pyrid-2-ylmethyl)-1H-benzimidazol-2-yl)[1,4]diazepan-1-yl)-2-(4-methoxyphenyl)butyl)benzamide;

N-Methyl-N-(4-(4-(1-(pyrid-2-ylmethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(ethoxycabonylmethyl)-1H-benzimidazol-2-yl)[1,4]diazepan-1-yl)-2-phenylbutyl)benzamide;

N-Methyl-N-(4-(4-(1-(ethoxycabonylmethyl)-1H-benzimidazol-2-yl)[1,4]diazepan-1-yl)-2-phenylbutyl)-3,4,5-trimethoxybenzamide;

N-Methyl-N-(4-(4-(1-(2-(ethoxycarbonyl)ethyl)-1H-benzimidazol-2-yl)[1,4]diazepan-1-yl)-2-(4-fluorophenyl)butyl)benzamide;

N-Methyl-N-(4-(4-(1-(ethoxycabonylmethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(3-(4-fluorophenoxy)propyl)-1H-benzimidazol-2-yl)[1,4]diazepan-1-yl)-2-(3-chlorophenyl)butyl)benzamide;

N-Methyl-N-(4-(4-(1-(ethoxycabonylmethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(3-(4-fluorophenoxy)propyl)-1H-benzimidazol-2-yl)[1,4]diazepan-1-yl)-2-(3,4-dichlorophenyl)butyl)benzamide;

N-Methyl-N-(4-(4-(1-(ethoxycabonylmethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(2-phenoxyethyl)-1H-benzimidazol-2-yl)[1,4]diazepan-1-yl)-2-(4-methoxyphenyl)butyl)benzamide;

N-Methyl-N-(4-(4-(1-(ethoxycabonylmethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(ethyl)-1H-benzimidazol-2-yl)[1,4]diazepan-1-yl)-2-phenylbutyl)benzamide;

N-Methyl-N-(4-(4-(1-(methyl)-1H-benzimidazol-2-yl)[1,4]diazepan-1-yl)-2-phenylbutyl)-3,4,5-trimethoxybenzamide;

N-Methyl-N-(4-(4-(1-(methyl)-1H-benzimidazol-2-yl)[1,4]diazepan-1-yl)-2-(4-fluorophenyl)butyl)benzamide;

N-Methyl-N-(4-(4-(1-(ethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(methyl)-1H-benzimidazol-2-yl)[1,4]diazepan-1-yl)-2-(3-chlorophenyl)butyl)benzamide;

N-Methyl-N-(4-(4-(1-(propyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(methyl)-1H-benzimidazol-2-yl)[1,4]diazepan-1-yl)-2-(3,4-dichlorophenyl)butyl)benzamide;

N-Methyl-N-(4-(4-(1-(ethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(butyl)-1H-benzimidazol-2-yl)[1,4]diazepan-1-yl)-2-(4-methoxyphenyl)butyl)benzamide;

N-Methyl-N-(4-(4-(1-(methyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(4-fluorobenzyl)-1H-benzimidazol-2-yl)[1,4]diazepan-1-yl)-2-phenylbutyl)benzamide;

N-Methyl-N-(4-(4-(1-(4-fluorobenzyl)-1H-benzimidazol-2-yl)[1,4]diazepan-1-yl)-2-phenylbutyl)-3,4,5-trimethoxybenzamide;

N-Methyl-N-(4-(4-(1-(4-fluorobenzyl)-1H-benzimidazol-2-yl)[1,4]diazepan-1-yl)-2-(4-fluorophenyl)butyl)benzamide;

N-Methyl-N-(4-(4-(1-(4-fluorobenzyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(4-fluorobenzyl)-1H-benzimidazol-2-yl)[1,4]diazepan-1-yl)-2-(3-chlorophenyl)butyl)benzamide;

N-Methyl-N-(4-(4-(1-(4-fluorobenzyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(4-fluorobenzyl)-1H-benzimidazol-2-yl)[1,4]diazepan-1-yl)-2-(3,4-dichlorophenyl)butyl)benzamide;

N-Methyl-N-(4-(4-(1-(4-fluorobenzyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(4-fluorobenzyl)-1H-benzimidazol-2-yl)[1,4]diazepan-1-yl)-2-(4-methoxyphenyl)butyl)benzamide;

N-Methyl-N-(4-(4-(1-(4-fluorobenzyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-phenylbutyl)benzamide;

N-Methyl-N-(4-(4-(1-(2-(2,2,2-trifluoroethoxy)ethyl)-1H-benzimidazol-2-yl)[1,4]diazepan-1-yl)-2-phenylbutyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(4-fluorophenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(3,4-difluorophenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(3,4-difluorophenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(3-chlorophenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(4-chlorophenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(4-chlorophenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)-3,5-bis(trifluoromethyl)benzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)-4-chlorobenzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)-4-methylbenzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)-4-t-butylbenzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)-2,4-dimethoxybenzamide;

N-Methyl-N-(4-(4-(1-(2-(2,2,2-trifluoroethoxy)ethyl)-1H-benzimidazol-2-yl)[1,4]diazepan-1-yl)-2-(4-methoxyphenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(3-methoxyphenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(3-methoxyphenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(3,4-dimethoxyphenyl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(3,4-dimethoxyphenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(benzo[1,3]dioxol-5-yl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(benzo[1,3]dioxol-5-yl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(naphth-2-yl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(3-trifluoromethylphenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(4-trifluoromethylphenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(thien-2-yl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(pyrid-2-yl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(pyrid-2-yl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(pyrid-3-yl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(pyrid-3-yl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(pyrid-4-yl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(pyrid-4-yl)butyl)benzamide;

N-Methyl-N-(4-(4-(1-(2-(2,2,2-trifluoroethoxy)ethyl)-1H-benzimidazol-2-yl)[1,4]diazepan-1-yl)-2-(3,4-dimethylphenyl)butyl)-3,4,5-trimethoxybenzamide;

N-Methyl-N-(4-(4-(1-(2-(2,2,2-trifluoroethoxy)ethyl)-1H-benzimidazol-2-yl)[1,4]diazepan-1-yl)-2-(4-fluorophenyl)butyl)-2-methoxy-5-(1H-tetrazol-1-yl)benzamide;

N-Methyl-N-(4-(4-(1-(2-(2,2,2-trifluoroethoxy)ethyl)-1H-benzimidazol-2-yl)[1,4]diazepan-1-yl)-2-(4-fluorophenyl)butyl)-2-methoxy-5-(4H-triazol-4-yl)benzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)2-methoxy-5-(1H-tetrazol-1-yl)benzamide;

N-Methyl-N-(4-(4-(1-(2-(2,2,2-trifluoroethoxy)ethyl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(pentyl)-1H-benzimidazol-2-yl)[1,4]diazepan-1-yl)-2-phenylbutyl)benzamide;

N-Methyl-N-(4-(4-(1-(pentyl)-1H-benzimidazol-2-yl)[1,4]diazepan-1-yl)-2-phenylbutyl)-3,4,5-trimethoxybenzamide;

N-Methyl-N-(4-(4-(1-(pentyl)-1H-benzimidazol-2-yl)[1,4]diazepan-1-yl)-2-(4-fluorophenyl)butyl)benzamide;

N-Methyl-N-(4-(4-(1-(pentyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(pentyl)-1H-benzimidazol-2-yl)[1,4]diazepan-1-yl)-2-(3,4-difluorophenyl)butyl)benzamide;

N-Methyl-N-(4-(4-(1-(pentyl)-1H-benzimidazol-2-yl)[1,4]diazepan-1-yl)-2-(3,4-difluorophenyl)butyl)-3,4,5-trimethoxybenzamide;

N-Methyl-N-(4-(4-(1-(pentyl)-1H-benzimidazol-2-yl)[1,4]diazepan-1-yl)-2-(3-chlorophenyl)butyl)benzamide;

N-Methyl-N-(4-(4-(1-(pentyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(pentyl)-1H-benzimidazol-2-yl)[1,4]diazepan-1-yl)-2-(4-chlorophenyl)butyl)benzamide;

N-Methyl-N-(4-(4-(1-(pentyl)-1H-benzamidazol-2-yl)[1,4]diazepan-1-yl)-2-(4-chlorophenyl)butyl)-3,4,5-trimethoxybenzamide;

N-Methyl-N-(4-(4-(1-(pentyl)-1H-benzimidazol-2-yl)[1,4]diazepan-1-yl)-2-(3,4-dichlorophenyl)butyl)benzamide;

N-Methyl-N-(4-(4-(1-(pentyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(pentyl)-1H-benzimidazol-2-yl)[1,4]diazepan-1-yl)-2-(3,4-dichlorophenyl)butyl)-3,5-bis(trifluoromethyl)benzamide;

N-Methyl-N-(4-(4-(1-(pentyl)-1H-benzimidazol-2-yl)[1,4]diazepan-1-yl)-2-(3,4-dichlorophenyl)butyl)-4-chlorobenzamide;

N-Methyl-N-(4-(4-(1-(pentyl)-1H-benzimidazol-2-yl)[1,4]diazepan-1-yl)-2-(3,4-dichlorophenyl)butyl)-4-methylbenzamide;

N-Methyl-N-(4-(4-(1-(pentyl)-1H-benzimidazol-2-yl)[1,4]diazepan-1-yl)-2-(3,4-dichlorophenyl)butyl)-4-t-butylbenzamide;

N-Methyl-N-(4-(4-(1-(pentyl)-1H-benzimidazol-2-yl)[1,4]diazepan-1-yl)-2-(3,4-dichlorophenyl)butyl)-2,4-dimethoxybenzamide;

N-Methyl-N-(4-(4-(1-(pentyl)-1H-benzimidazol-2-yl)[1,4]diazepan-1-yl)-2-(4-methoxyphenyl)butyl)benzamide;

N-Methyl-N-(4-(4-(1-(pentyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(pentyl)-1H-benzimidazol-2-yl)[1,4]diazepan-1-yl)-2-(3-methoxyphenyl)butyl)benzamide;

N-Methyl-N-(4-(4-(1-(pentyl)-1H-benzimidazol-2-yl)[1,4]diazepan-1-yl)-2-(3-methoxyphenyl)butyl)-3,4,5-trimethoxybenzamide;

N-Methyl-N-(4-(4-(1-(pentyl)-1H-benzimidazol-2-yl)[1,4]diazepan-1-yl)-2-(3,4-dimethoxyphenyl)butyl)benzamide;

N-Methyl-N-(4-(4-(1-(pentyl)-1H-benzimidazol-2-yl)[1,4]diazepan-1-yl)-2-(3,4-dimethoxyphenyl)butyl)-3,4,5-trimethoxybenzamide;

N-Methyl-N-(4-(4-(1-(pentyl)-1H-benzimidazol-2-yl)[1,4]diazepan-1-yl)-2-(benzo[1,3]dioxol-5-yl)butyl)benzamide;

N-Methyl-N-(4-(4-(1-(pentyl)-1H-benzimidazol-2-yl)[1,4]diazepan-1-yl)-2-(benzo[1,3]dioxol-5-yl)butyl)-3,4,5-trimethoxybenzamide;

N-Methyl-N-(4-(4-(1-(pentyl)-1H-benzimidazol-2-yl)[1,4]diazepan-1-yl)-2-(naphth-2-yl)butyl)benzamide;

N-Methyl-N-(4-(4-(1-(pentyl)-1H-benzimidazol-2-yl)[1,4]diazepan-1-yl)-2-(3-trifluoromethylphenyl)butyl)-3,4,5-trimethoxybenzamide;

N-Methyl-N-(4-(4-(1-(pentyl)-1H-benzimidazol-2-yl)[1,4]diazepan-1-yl)-2-(4-trifluoromethylphenyl)butyl)-3,4,5-trimethoxybenzamide;

N-Methyl-N-(4-(4-(1-(pentyl)-1H-benzimidazol-2-yl)[1,4]diazepan-1-yl)-2-(thien-2-yl)butyl)-3,4,5-trimethoxybenzamide;

N-Methyl-N-(4-(4-(1-(pentyl)-1H-benzimidazol-2-yl)[1,4]diazepan-1-yl)-2-(pyrid-2-yl)butyl)benzamide;
N-Methyl-N-(4-(4-(1-(pentyl)-1H-benzimidazol-2-yl)[1,4]diazepan-1-yl)-2-(pyrid-2-yl)butyl)-3,4,5-trimethoxybenzamide;
N-Methyl-N-(4-(4-(1-(pentyl)-1H-benzimidazol-2-yl)[1,4]diazepan-1-yl)-2-(pyrid-3-yl)butyl)benzamide;
N-Methyl-N-(4-(4-(1-(pentyl)-1H-benzimidazol-2-yl)[1,4]diazepan-1-yl)-2-(pyrid-3-yl)butyl)-3,4,5-trimethoxybenzamide;
N-Methyl-N-(4-(4-(1-(pentyl)-1H-benzimidazol-2-yl)[1,4]diazepan-1-yl)-2-(pyrid-4-yl)butyl)-3,4,5-trimethoxybenzamide;
N-Methyl-N-(4-(4-(1-(pentyl)-1H-benzimidazol-2-yl)[1,4]diazepan-1-yl)-2-(pyrid-4-yl)butyl)benzamide;
N-Methyl-N-(4-(4-(1-(pentyl)-1H-benzimidazol-2-yl)[1,4]diazepan-1-yl)-2-(3,4-dimethylphenyl)butyl)-3,4,5-trimethoxybenzamide;
N-Methyl-N-(4-(4-(1-(pentyl)-1H-benzimidazol-2-yl)[1,4]diazepan-1-yl)-2-(4-fluorophenyl)butyl)-2-methoxy-5-(1H-tetrazol-1-yl)benzamide;
N-Methyl-N-(4-(4-(1-(pentyl)-1H-benzimidazol-2-yl)[1,4]diazepan-1-yl)-2-(4-fluorophenyl)butyl)-2-methoxy-5-(4H-triazol-4-yl)benzamide;
N-Methyl-N-(4-(4-(1-(pentyl)-1H-benzimidazol-2-yl)[1,4]diazepan-1-yl)-2-(3,4-dichlorophenyl)butyl)2-methoxy-5-(1H-tetrazol-1-yl)benzamide;
N-Methyl-N-(4-(4-(1-(pentyl)-1H-benzimidazol-2-yl)[1,4]diazepan-1-yl)-2-(3,4-dichlorophenyl)butyl)-2-methoxy-5-(4H-triazol-4-yl)benzamide;
N-Methyl-N-(4-(4-(1-(fur-3-ylmethyl)-1H-benzimidazol-2-yl)[1,4]diazepan-1-yl)-2-phenylbutyl)benzamide;
N-Methyl-N-(4-(4-(1-(fur-3-ylmethyl)-1H-benzimidazol-2-yl)[1,4]diazepan-1-yl)-2-phenylbutyl)-3,4,5-trimethoxybenzamide;
N-Methyl-N-(4-(4-(1-(fur-3-ylmethyl)-1H-benzimidazol-2-yl)[1,4]diazepan-1-yl)-2-(4-fluorophenyl)butyl)benzamide;
N-Methyl-N-(4-(4-(1-(fur-3-ylmethyl)-1H-benzimidazol-2-yl)[1,4]diazepan-1-yl)-2-(4-fluorophenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(3,4-difluorophenyl)butyl)benzamide;
N-Methyl-N-(4-(4-(1-(fur-3-ylmethyl)-1H-benzimidazol-2-yl)[1,4]diazepan-1-yl)-2-(3,4-difluorophenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(3-chlorophenyl)butyl)benzamide;
N-Methyl-N-(4-(4-(1-(fur-3-ylmethyl)-1H-benzimidazol-2-yl)[1,4]diazepan-1-yl)-2-(3-chlorophenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(4-chlorophenyl)butyl)benzamide;
N-Methyl-N-(4-(4-(1-(fur-3-ylmethyl)-1H-benzimidazol-2-yl)[1,4]diazepan-1-yl)-2-(4-chlorophenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(3,4-dichlorophenyl)butyl)benzamide;
N-Methyl-N-(4-(4-(1-(fur-3-ylmethyl)-1H-benzimidazol-2-yl)[1,4]diazepan-1-yl)-2-(3,4-dichlorophenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(3,4-dichlorophenyl)butyl)-3,5-bis(trifluoromethyl)benzamide;
N-Methyl-N-(4-(4-(1-(fur-3-ylmethyl)-1H-benzimidazol-2-yl)[1,4]diazepan-1-yl)-2-(3,4-dichlorophenyl)butyl)-4-chlorobenzamide;
N-Methyl-N-(4-(4-(1-(fur-3-ylmethyl)-1H-benzimidazol-2-yl)[1,4]diazepan-1-yl)-2-(3,4-dichlorophenyl)butyl)-4-methylbenzamide;
N-Methyl-N-(4-(4-(1-(fur-3-ylmethyl)-1H-benzimidazol-2-yl)[1,4]diazepan-1-yl)-2-(3,4-dichlorophenyl)butyl)-4-t-butylbenzamide;
N-Methyl-N-(4-(4-(1-(fur-3-ylmethyl)-1H-benzimidazol-2-yl)[1,4]diazepan-1-yl)-2-(3,4-dichlorophenyl)butyl)-2,4-dimethoxybenzamide;
N-Methyl-N-(4-(4-(1-(fur-3-ylmethyl)-1H-benzimidazol-2-yl)[1,4]diazepan-1-yl)-2-(4-methoxyphenyl)butyl)benzamide;
N-Methyl-N-(4-(4-(1-(fur-3-ylmethyl)-1H-benzimidazol-2-yl)[1,4]diazepan-1-yl)-2-(4-methoxyphenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(3-methoxyphenyl)butyl)benzamide;
N-Methyl-N-(4-(4-(1-(fur-3-ylmethyl)-1H-benzimidazol-2-yl)[1,4]diazepan-1-yl)-2-(3-methoxyphenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(3,4-dimethoxyphenyl)butyl)benzamide;
N-Methyl-N-(4-(4-(1-(fur-3-ylmethyl)-1H-benzimidazol-2-yl)[1,4]diazepan-1-yl)-2-(3,4-dimethoxyphenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(benzo[1,3]dioxol-5-yl)butyl)benzamide;
N-Methyl-N-(4-(4-(1-(fur-3-ylmethyl)-1H-benzimidazol-2-yl)[1,4]diazepan-1-yl)-2-(benzo[1,3]dioxol-5-yl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(naphth-2-yl)butyl)benzamide;
N-Methyl-N-(4-(4-(1-(fur-3-ylmethyl)-1H-benzimidazol-2-yl)[1,4]diazepan-1-yl)-2-(3-trifluoromethylphenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(4-trifluoromethylphenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(thien-2-yl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(pyrid-2-yl)butyl)benzamide;
N-Methyl-N-(4-(4-(1-(fur-3-ylmethyl)-1H-benzimidazol-2-yl)[1,4]diazepan-1-yl)-2-(pyrid-2-yl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(pyrid-3-yl)butyl)benzamide;
N-Methyl-N-(4-(4-(1-(fur-3-ylmethyl)-1H-benzimidazol-2-yl)[1,4]diazepan-1-yl)-2-(pyrid-3-yl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(pyrid-4-yl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(pyrid-4-yl)butyl)benzamide;
N-Methyl-N-(4-(4-(1-(fur-3-ylmethyl)-1H-benzimidazol-2-yl)[1,4]diazepan-1-yl)-2-(3,4-dimethylphenyl)butyl)-3,4,5-trimethoxybenzamide;
N-Methyl-N-(4-(4-(1-(fur-3-ylmethyl)-1H-benzimidazol-2-yl)[1,4]diazepan-1-yl)-2-(4-fluorophenyl)butyl)-5-trifluoromethoxy-2-methoxybenzamide;

N-Methyl-N-(4-(4-(1-(fur-3-ylmethyl)-1H-benzimidazol-2-yl)[1,4]diazepan-1-yl)-2-(4-fluorophenyl)butyl)-2-methoxy-5-(1H-tetrazol-1-yl)benzamide;

N-Methyl-N-(4-(4-(1-(fur-3-ylmethyl)-1H-benzimidazol-2-yl)[1,4]diazepan-1-yl)-2-(4-fluorophenyl)butyl)-2-methoxy-5-(4H-triazol-4-yl)benzamide;

N-Methyl-N-(4-(4-(1-(fur-3-ylmethyl)-1H-benzimidazol-2-yl)[1,4]diazepan-1-yl)-2-(3,4-dichlorophenyl)butyl)2-methoxy-5-(1H-tetrazol-1-yl)benzamide;

N-Methyl-N-(4-(4-(1-(fur-3-ylmethyl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(fur-2-ylmethyl)-1H-benzimidazol-2-yl)[1,4]diazepan-1-yl)-2-phenylbutyl)benzamide;

N-Methyl-N-(4-(4-(1-(fur-2-ylmethyl)-1H-benzimidazol-2-yl)[1,4]diazepan-1-yl)-2-phenylbutyl)-3,4,5-trimethoxybenzamide;

N-Methyl-N-(4-(4-(1-(fur-2-ylmethyl)-1H-benzimidazol-2-yl)[1,4]diazepan-1-yl)-2-(4-fluorophenyl)butyl)benzamide;

N-Methyl-N-(4-(4-(1-(fur-2-ylmethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(3,4-difluorophenyl)butyl)benzamide;

N-Methyl-N-(4-(4-(1-(fur-2-ylmethyl)-1H-benzimidazol-2-yl)[1,4]diazepan-1-yl)-2-(3,4-difluorophenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(3-chlorophenyl)butyl)benzamide;

N-Methyl-N-(4-(4-(1-(fur-2-ylmethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(4-chlorophenyl)butyl)benzamide;

N-Methyl-N-(4-(4-(1-(fur-2-ylmethyl)-1H-benzimidazol-2-yl)[1,4]diazepan-1-yl)-2-(4-chlorophenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(3,4-dichlorophenyl)butyl)benzamide;

N-Methyl-N-(4-(4-(1-(fur-2-ylmethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(3,4-dichlorophenyl)butyl)-3,5-bis(trifluoromethyl)benzamide;

N-Methyl-N-(4-(4-(1-(fur-2-ylmethyl)-1H-benzimidazol-2-yl)[1,4]diazepan-1-yl)-2-(3,4-dichlorophenyl)butyl)-4-chlorobenzamide;

N-Methyl-N-(4-(4-(1-(fur-2-ylmethyl)-1H-benzimidazol-2-yl)[1,4]diazepan-1-yl)-2-(3,4-dichlorophenyl)butyl)-4-methylbenzamide;

N-Methyl-N-(4-(4-(1-(fur-2-ylmethyl)-1H-benzimidazol-2-yl)[1,4]diazepan-1-yl)-2-(3,4-dichlorophenyl)butyl)-4-t-butylbenzamide;

N-Methyl-N-(4-(4-(1-(fur-2-ylmethyl)-1H-benzimidazol-2-yl)[1,4]diazepan-1-yl)-2-(3,4-dichlorophenyl)butyl)-2,4-dimethoxybenzamide;

N-Methyl-N-(4-(4-(1-(fur-2-ylmethyl)-1H-benzimidazol-2-yl)[1,4]diazepan-1-yl)-2-($^4$-methoxyphenyl)butyl)benzamide;

N-Methyl-N-(4-(4-(1-(fur-2-ylmethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(3-methoxyphenyl)butyl)benzamide;

N-Methyl-N-(4-(4-(1-(fur-2-ylmethyl)-1H-benzimidazol-2-yl)[1,4]diazepan-1-yl)-2-(3-methoxyphenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(3,4-dimethoxyphenyl)butyl)benzamide;

N-Methyl-N-(4-(4-(1-(fur-2-ylmethyl)-1H-benzimidazol-2-yl)[1,4]diazepan-1-yl)-2-(3,4-dimethoxyphenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(benzo[1,3]dioxol-5-yl)butyl)benzamide;

N-Methyl-N-(4-(4-(1-(fur-2-ylmethyl)-1H-benzimidazol-2-yl)[1,4]diazepan-1-yl)-2-(benzo[1,3]dioxol-5-yl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(naphth-2-yl)butyl)benzamide;

N-Methyl-N-(4-(4-(1-(fur-2-ylmethyl)-1H-benzimidazol-2-yl)[1,4]diazepan-1-yl)-2-(3-trifluoromethylphenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(4-trifluoromethylphenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(thien-2-yl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(pyrid-2-yl)butyl)benzamide;

N-Methyl-N-(4-(4-(1-(fur-2-ylmethyl)-1H-benzimidazol-2-yl)[1,4]diazepan-1-yl)-2-(pyrid-2-yl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(pyrid-3-yl)butyl)benzamide;

N-Methyl-N-(4-(4-(1-(fur-2-ylmethyl)-1H-benzimidazol-2-yl)[1,4]diazepan-1-yl)-2-(pyrid-3-yl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(pyrid-4-yl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(pyrid-4-yl)butyl)benzamide;

N-Methyl-N-(4-(4-(1-(fur-2-ylmethyl)-1H-benzimidazol-2-yl)[1,4]diazepan-1-yl)-2-(3,4-dimethylphenyl)butyl)-3,4,5-trimethoxybenzamide;

N-Methyl-N-(4-(4-(1-(fur-2-ylmethyl)-1H-benzimidazol-2-yl)[1,4]diazepan-1-yl)-2-(4-fluorophenyl)butyl)-5-trifluoromethoxy-2-methoxybenzamide;

N-Methyl-N-(4-(4-(1-(fur-2-ylmethyl)-1H-benzimidazol-2-yl)[1,4]diazepan-1-yl)-2-(4-fluorophenyl)butyl)-2-methoxy-5-(1H-tetrazol-1-yl)benzamide;

N-Methyl-N-(4-(4-(1-(fur-2-ylmethyl)-1H-benzimidazol-2-yl)[1,4]diazepan-1-yl)-2-(4-fluorophenyl)butyl)-2-methoxy-5-(4H-triazol-4-yl)benzamide N-Methyl-N-(4-(4-(1-(fur-2-ylmethyl)-1H-benzimidazol-2-yl)[1,4]diazepan-1-yl)-2-(3,4-dichlorophenyl)butyl)2-methoxy-5-(1H-tetrazol-1-yl)benzamide;

N-Methyl-N-(4-(4-(1-(fur-2-ylmethyl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(2,2,2-trifluoroethyl)-1H-benzimidazol-2-yl)[1,4]diazepan-1-yl)-2-phenylbutyl)benzamide;

N-Methyl-N-(4-(4-(1-(2,2,2-trifluoroethyl)-1H-benzimidazol-2-yl)[1,4]diazepan-1-yl)-2-phenylbutyl)-3,4,5-trimethoxybenzamide;

N-Methyl-N-(4-(4-(1-(2,2,2-trifluoroethyl)-1H-benzimidazol-2-yl)[1,4]diazepan-1-yl)-2-(4-fluorophenyl)butyl)benzamide;

N-Methyl-N-(4-(4-(1-(2,2,2-trifluoroethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(2,2,2-trifluoroethyl)-1H-benzimidazol-2-yl)[1,4]diazepan-1-yl)-2-(3-chlorophenyl)butyl)benzamide;

N-Methyl-N-(4-(4-(1-(2,2,2-trifluoroethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(2,2,2-trifluoroethyl)-1H-benzimidazol-2-yl)[1,4]diazepan-1-yl)-2-(3,4-dichlorophenyl)butyl)benzamide;

N-Methyl-N-(4-(4-(1-(2,2,2-trifluoroethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(2,2,2-trifluoroethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(2,2,2-trifluoroethyl)-1H-benzimidazol-2-yl)[1,4]diazepan-1-yl)-2-(4-fluorophenyl)butyl)-5-trifluoromethoxy-2-methoxybenzamide;

N-Methyl-N-(4-(4-(1-(2,2,2-trifluoroethyl)-1H-benzimidazol-2-yl)[1,4]diazepan-1-yl)-2-(4-fluorophenyl)butyl)-2-methoxy-5-(1H-tetrazol-1-yl)benzamide;

N-Methyl-N-(4-(4-(1-(2,2,2-trifluoroethyl)-1H-benzimidazol-2-yl)[1,4]diazepan-1-yl)-2-(4-fluorophenyl)butyl)-2-methoxy-5-(4H-triazol-4-yl)benzamide;

N-Methyl-N-(4-(4-(1-(2,2,2-trifluoroethyl)-1H-benzimidazol-2-yl)[1,4]diazepan-1-yl)-2-(3,4-dichlorophenyl)butyl)2-methoxy-5-(1H-tetrazol-1-yl)benzamide;

N-Methyl-N-(4-(4-(1-(2,2,2-trifluoroethyl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(2-(trifluoromethoxy)ethyl)-1H-benzimidazol-2-yl)[1,4]diazepan-1-yl)-2-phenylbutyl)benzamide;

N-Methyl-N-(4-(4-(1-(2-(trifluoromethoxy)ethyl)-1H-benzimidazol-2-yl)[1,4]diazepan-1-yl)-2-phenylbutyl)-3,4,5-trimethoxybenzamide;

N-Methyl-N-(4-(4-(1-(2-(trifluoromethoxy)ethyl)-1H-benzimidazol-2-yl)[1,4]diazepan-1-yl)-2-(4-fluorophenyl)butyl)benzamide;

N-Methyl-N-(4-(4-(1-(2-(trifluoromethoxy)ethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(2-(trifluoromethoxy)ethyl)-1H-benzimidazol-2-yl)[1,4]diazepan-1-yl)-2-(3-chlorophenyl)butyl)benzamide;

N-Methyl-N-(4-(4-(1-(2-(trifluoromethoxy)ethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(2-(trifluoromethoxy)ethyl)-1H-benzimidazol-2-yl)[1,4]diazepan-1-yl)-2-(3,4-dichlorophenyl)butyl)benzamide;

N-Methyl-N-(4-(4-(1-(2-(trifluoromethoxy)ethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(2-(trifluoromethoxy)ethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(2-(trifluoromethoxy)ethyl)-1H-benzimidazol-2-yl)[1,4]diazepan-1-yl)-2-(4-fluorophenyl)butyl)-5-trifluoromethoxy-2-methoxybenzamide;

N-Methyl-N-(4-(4-(1-(2-(trifluoromethoxy)ethyl)-1H-benzimidazol-2-yl)[1,4]diazepan-1-yl)-2-(4-fluorophenyl)butyl)-2-methoxy-5-(1H-tetrazol-1-yl)benzamide;

N-Methyl-N-(4-(4-(1-(2-(trifluoromethoxy)ethyl)-1H-benzimidazol-2-yl)[1,4]diazepan-1-yl)-2-(4-fluorophenyl)butyl)-2-methoxy-5-(4H-triazol-4-yl)benzamide;

N-Methyl-N-(4-(4-(1-(2-(trifluoromethoxy)ethyl)-1H-benzimidazol-2-yl)[1,4]diazepan-1-yl)-2-(3,4-dichlorophenyl)butyl)2-methoxy-5-(1H-tetrazol-1-yl)benzamide;

N-Methyl-N-(4-(4-(1-(2-(trifluoromethoxy)ethyl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(2-phenylsulfonylethyl)-1H-benzimidazol-2-yl)[1,4]diazepan-1-yl)-2-phenylbutyl)benzamide;

N-Methyl-N-(4-(4-(1-(2-phenylsulfonylethyl)-1H-benzimidazol-2-yl)[1,4]diazepan-1-yl)-2-phenylbutyl)-3,4,5-trimethoxybenzamide;

N-Methyl-N-(4-(4-(1-(2-phenylsulfonylethyl)-1H-benzimidazol-2-yl)[1,4]diazepan-1-yl)-2-(4-fluorophenyl)butyl)benzamide;

N-Methyl-N-(4-(4-(1-(2-phenylsulfonylethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(2-phenylsulfonylethyl)-1H-benzimidazol-2-yl)[1,4]diazepan-1-yl)-2-(3-chlorophenyl)butyl)benzamide;

N-Methyl-N-(4-(4-(1-(2-phenylsulfonylethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(2-phenylsulfonylethyl)-1H-benzimidazol-2-yl)[1,4]diazepan-1-yl)-2-(3,4-dichlorophenyl)butyl)benzamide;

N-Methyl-N-(4-(4-(1-(2-phenylsulfonylethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(2-phenylsulfonylethyl)-1H-benzimidazol-2-yl)[1,4]diazepan-1-yl)-2-(4-methoxyphenyl)butyl)benzamide;

N-Methyl-N-(4-(4-(1-(2-phenylsulfonylethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(2-ethylsulfonylethyl)-1H-benzimidazol-2-yl)[1,4]diazepan-1-yl)-2-phenylbutyl)benzamide;

N-Methyl-N-(4-(4-(1-(2-methylsulfonylethyl)-1H-benzimidazol-2-yl)[1,4]diazepan-1-yl)-2-phenylbutyl)-3,4,5-trimethoxybenzamide;

N-Methyl-N-(4-(4-(1-(2-ethylsulfonylethyl)-1H-benzimidazol-2-yl)[1,4]diazepan-1-yl)-2-(4-fluorophenyl)butyl)benzamide;

N-Methyl-N-(4-(4-(1-(2-methylsulfonylethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(2-methylsulfonylethyl)-1H-benzimidazol-2-yl)[1,4]diazepan-1-yl)-2-(3-chlorophenyl)butyl)benzamide;

N-Methyl-N-(4-(4-(1-(2-ethylsulfonylethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(2-methylsulfonylethyl)-1H-benzimidazol-2-yl)[1,4]diazepan-1-yl)-2-(3,4-dichlorophenyl)butyl)benzamide;

N-Methyl-N-(4-(4-(1-(2-methylsulfonylethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(2-methylsulfonylethyl)-1H-benzimidazol-2-yl)[1,4]diazepan-1-yl)-2-(4-methoxyphenyl)butyl)benzamide;

N-Methyl-N-(4-(4-(1-(2-ethylsulfonylethyl)-1H-benzimidazol-2-yl)[1,4]diazepan-1-yl)-2-(4-methoxyphenyl)butyl)-3,4,5-trimethoxybenzamide;

N-Methyl-N-(4-(4-(1-(but-2-en-1-yl)-1H-benzimidazol-2-yl)[1,4]diazepan-1-yl)-2-(4-fluorophenyl)butyl)benzamide;

N-Methyl-N-(4-(4-(1-(but-2-en-1-yl)-1H-benzimidazol-2-yl)[1,4]diazepan-1-yl)-2-(4-fluorophenyl)butyl)-3,4,5-trimethoxybenzamide;

N-Methyl-N-(4-(4-(1-(but-2-en-1-yl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(but-2-en-1-yl)-1H-benzimidazol-2-yl)[1,4]diazepan-1-yl)-2-(4-fluorophenyl)butyl)-5-trifluoromethoxy-2-methoxybenzamide;

N-Methyl-N-(4-(4-(1-(but-2-en-1-yl)-1H-benzimidazol-2-yl)[1,4]diazepan-1-yl)-2-(4-fluorophenyl)butyl)-2-methoxy-5-(4H-triazol-4-yl)benzamide ;

N-Methyl-N-(4-(4-(1-(but-2-en-1-yl)-1H-benzimidazol-2-yl)[1,4]diazepan-1-yl)-2-(3,4-dichlorophenyl)butyl)2-methoxy-5-(1H-tetrazol-1-yl)benzamide;

N-Methyl-N-(4-(4-(1-(but-2-en-1-yl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(allyl)-1H-benzimidazol-2-yl)[1,4]diazepan-1-yl)-2-(4-fluorophenyl)butyl)benzamide;

N-Methyl-N-(4-(4-(1-(allyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(allyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(allyl)-1H-benzimidazol-2-yl)[1,4]diazepan-1-yl)-2-(4-fluorophenyl)butyl)-5-trifluoromethoxy-2-methoxybenzamide;

N-Methyl-N-(4-(4-(1-(allyl)-1H-benzimidazol-2-yl)[1,4]diazepan-1-yl)-2-(4-fluorophenyl)butyl)-2-methoxy-5-(1H-tetrazol-1-yl)benzamide;

N-Methyl-N-(4-(4-(1-(allyl)-1H-benzimidazol-2-yl)[1,4]diazepan-1-yl)-2-(4-fluorophenyl)butyl)-2-methoxy-5-(4H-triazol-4-yl)benzamide;

N-Methyl-N-(4-(4-(1-(allyl)-1H-benzimidazol-2-yl)[1,4]diazepan-1-yl)-2-(3,4-dichlorophenyl)butyl)2-methoxy-5-(1H-tetrazol-1-yl)benzamide;

N-Methyl-N-(4-(4-(1-(allyl)-1H-benzimidazol-2-yl)[1,4]diazepan-1-yl)-2-(3,4-dichlorophenyl)butyl)-2-methoxy-5-(4H-triazol-4-yl)benzamide;

N-Methyl-N-(4-(4-(1-(2-cyanoethyl)-1H-benzimidazol-2-yl)[1,4]diazepan-1-yl)-2-phenylbutyl)benzamide;

N-Methyl-N-(4-(4-(1-(2-cyanoethyl)-1H-benzimidazol-2-yl)[1,4]diazepan-1-yl)-2-phenylbutyl)-3,4,5-trimethoxybenzamide;

N-Methyl-N-(4-(4-(1-(2-cyanoethyl)-1H-benzimidazol-2-yl)[1,4]diazepan-1-yl)-2-(4-fluorophenyl)butyl)benzamide;

N-Methyl-N-(4-(4-(1-(2-cyanoethyl)-1H-benzimidazol-2-yl)[1,4]diazepan-1-yl)-2-(4-fluorophenyl)butyl)-3,4,5-trimethoxybenzamide;

N-Methyl-N-(4-(4-(1-(2-cyanoethyl)-1H-benzimidazol-2-yl)[1,4]diazepan-1-yl)-2-(3-chlorophenyl)butyl)benzamide;

N-Methyl-N-(4-(4-(1-(2-cyanoethyl)-1H-benzimidazol-2-yl)[1,4]diazepan-1-yl)-2-(3-chlorophenyl)butyl)-3,4,5-trimethoxybenzamide;

N-Methyl-N-(4-(4-(1-(2-cyanoethyl)-1H-benzimidazol-2-yl)[1,4]diazepan-1-yl)-2-(3,4-dichlorophenyl)butyl)benzamide;

N-Methyl-N-(4-(4-(1-(2-cyanoethyl)-1H-benzimidazol-2-yl)[1,4]diazepan-1-yl)-2-(3,4-dichlorophenyl)butyl)-3,4,5-trimethoxybenzamide;

N-Methyl-N-(4-(4-(1-(2-cyanoethyl)-1H-benzimidazol-2-yl)[1,4]diazepan-1-yl)-2-(4-methoxyphenyl)butyl)benzamide;

N-Methyl-N-(4-(4-(1-(2-cyanoethyl)-1H-benzimidazol-2-yl)[1,4]diazepan-1-yl)-2-(4-methoxyphenyl)butyl)-3,4,5-trimethoxybenzamide.

General synthetic procedures for preparing these compounds of formula (1) is set forth in Reaction Schemes A.1 and A.2. The reagents and starting materials are readily available to one of ordinary skill in the art. In Reaction Schemes A.1 and A.2, all substituents, unless otherwise indicated, are as previously defined.

Reaction Scheme A.1

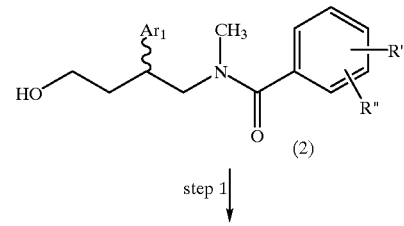

step 1

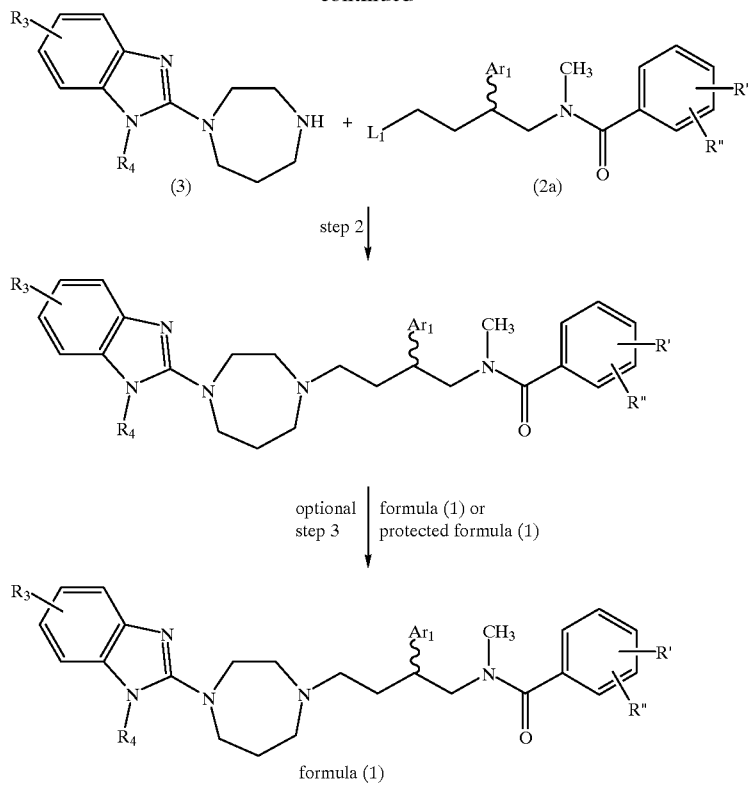

formula (1)

In Reaction Scheme A.1, step 1, the hydroxy group of an appropriate alcohol of structure 2 is converted to an appropriate leaving group to give a compound of structure 2a. An appropriate alcohol of structure 2 is one in which the stereochemistry is as desired in the final product of formula (1) and R', R", and $Ar_1$ are as desired in the final product of formula (1). Alternately, an appropriate alcohol of structure 2 can be one in which the stereochemistry gives rise after resolution to stereochemistry as desired in the final product of formula (1) and R', R', and $Ar_1$ are as desired in the final product of formula (1). An appropriate alcohol of structure 2 can also be one in which the stereochemistry and R' and R' are as desired in the final product of formula (1) and $Ar_1$ gives rise upon deprotection to $Ar_1$ as desired in the final product of formula (1). Alternately, an appropriate alcohol of structure 2 can also be one in which the stereochemistry gives rise after resolution to stereochemistry as desired in the final product of formula (1), R' and R" are as desired in the final product of formula (1), and $Ar_1$ gives rise upon deprotection to $Ar_1$ as desired in the final product of formula (1).

An appropriate alcohol of structure 2 can be prepared by methods described herein and by methods which are well known and appreciated in the art, such as U.S. Pat. Nos. 5,317,020 and 5,236,921, which are hereby incorporated by reference; European Patent Application Nos. 0 428 434, published May 22, 1991, 0 630 887, published Dec. 28, 1994, and 0 559 538, published Sep. 8, 1993; PCT Application Nos. WO 9417045, published Aug. 4, 1994 and WO 95415961, published Jun. 15, 1995; *Bioorganic & Medicinal Chemistry Letters*, 3, 319–322 (1993); and *Bioorganic & Medicinal Chemistry Letters*, 3, 925–930 (1993).

An appropriate leaving group, $L_1$, is one which can be displaced by a 4-(1H-benzimidazol-2-yl)[1,4]-diazepane of structure 3 to give rise to a compound of formula (1).

Appropriate leaving groups, $L_1$ include but are not limited to chloro, bromo, iodo, mesylate, tosylate, benzenesulfonate, and the like. The conversion of hydroxy groups to leaving groups such as chloro, bromo, iodo, mesylate, tosylate, and benzenesulfonate is well known and appreciated in the art.

For example, compounds in which $L_1$ is bromo are formed by contacting an appropriate alcohol of structure 2 with 1.0 to 1.5 molar equivalents of carbon tetrabromide and 1.0 to 1.75 molar equivalents triphenylphosphine. (P. J. Kocienski et al. *J. Org. Chem.*, 4, 353–355 (1977)). The reaction is carried out by combining the alcohol of structure 2 with carbon tetrabromide in a suitable solvent, such as dichloromethane or chloroform and then adding a solution of triphenylphosphine in a suitable solvent, such as dichloromethane or chloroform. Generally the reaction is carried out at temperatures of from −10° C. to ambient temperature. Generally, the reactions require from 5 minutes to 24 hours. The product can be isolated and purified by techniques well known in the art, such as extraction, evaporation, trituration, chromatography, and recrystallization.

Compounds in which $L_1$ is bromo are also formed by contacting an appropriate alcohol of structure 2 with a slight molar excess of triphenylphosphine dibromide. (R. F Borch et al. *J. Am. Chem. Soc.*, 4, 1612–1619 (1977)). The reaction may be carried out by contacting an appropriate alcohol of structure 2 with preformed triphenylphosphine dibromide. The reaction is carried out in a suitable solvent, such as tetrahydrofuran and diethyl ether. The reaction is carried out in the presence of a suitable base, such as pyridine. Generally the reaction is carried out at temperatures of from 0° C. to 50° C. Generally, the reactions require from 5 minutes to 24 hours. The product can be isolated and purified by techniques well known in the art, such as extraction, evaporation, trituration, chromatography, and recrystallization.

Alternately, for example, compounds in which $L_1$ is mesylate are formed by contacting an appropriate alcohol of structure 2 with a molar excess of methanesulfonyl chloride. The reaction is carried out in a suitable solvent, such as dichloromethane, chloroform, toluene, benzene, or pyridine. The reaction is carried out in the presence of a suitable base, such as triethylamine, diisopropylethylamine, or pyridine. Generally the reaction is carried out at temperatures of from −20° C. to 50° C. Generally, the reactions require from 1 hour to 24 hours. The product can be isolated and purified by techniques well known in the art, such as extraction, evaporation, trituration, chromatography, and recrystallization.

Compounds of structure 2a in which $L_1$ is iodo can be prepared from compounds of structure 2a in which $L_1$ is mesylate, chloro, or bromo by an exchange reaction, such as the Finkelstein reaction.

For example, a compound of structure 2a in which $L_1$ is mesylate, chloro, or bromo is contacted with from 1.0 to 10.0 molar equivalents of an iodide salt, such as sodium iodide or potassium iodide. The reaction is carried out in a suitable solvent, such as acetone, butanone, tetrahydrofuran, tetrahydrofuran/water mixtures, toluene, and acetonitrile. Generally, the reaction is carried out at temperatures of from ambient temperature to the refluxing temperature of the solvent. Generally, the reactions require from 1 hour to 24 hours. The product can be isolated and purified by techniques well known in the art, such as extraction, evaporation, trituration, chromatography, and recrystallization.

In Reaction Scheme A.1, step 2, the compound of structure 2a reacts with an appropriate 4-(1H-benzimidazol-2-yl)[1,4]diazepane compound of structure 3 or a salt thereof to give a protected compound of formula (1) or a compound of formula (1).

An appropriate 4-(1H-benzimidazol-2-yl)[1,4]diazepane of structure 3 or salt thereof is one in which $R_3$ and $R_4$ are as desired in the final product of formula (1) or $R_4$ gives rise after deprotection or modification to $R_4$ as desired in the final product of formula (1). Appropriate 4-(1H-benzimidazol-2-yl)[1,4]diazepanes of structure 3 are well known and appreciated in the art. Appropriate 4-(1H-benzimidazol-2-yl)[1,4]diazepanes of structure 3 may be prepared by methods known in the art such as described in *J. Med. Chem.* 29, 1178–1183 (1986) and *Chem. Pharm. Bull.*, 37 962–966 (1989); and by methods analogous to those methods and to those described herein by carrying out suitable deprotections, protections, and alkylations, and modifications, such as the reduction of esters, as are well known in the art, in the order and number required for formation of an appropriate 4-(1H-benzimidazol-2-yl)[1,4] diazepane of structure 3.

For example, the compound of structure 2a is contacted with an appropriate 4-(1H-benzimidazol-2-yl)[1,4] diazepane compound of structure 3 or salt thereof to give a protected compound of formula (1) or a compound of formula (1). The reaction is carried out in a suitable solvent, such as dioxane, tetrahydrofuran, tetrahydrofuran/water mixtures, acetone, acetone/water mixtures, ethyl acetate, ethyl acetate/water mixtures, pyridine, acetonitrile, toluene, toluene/water mixtures, chlorobenzene, or dimethylformamide, with acetonitrile being preferred. The reaction is carried out in the presence of from 1.0 to 6.0 molar equivalents of a suitable base, such as sodium carbonate, sodium bicarbonate, potassium carbonate, potassium bicarbonate, triethylamine, pyridine, or diisopropylethylamine, with diisopropylethylamine being preferred. When a salt of an appropriate 4-(1H-benzimidazol-2-yl)[1,4]diazepane of structure 3 is used, a molar excess of a suitable base may be required to absorb the acid liberated from the salt. The reaction may be facilitated by the addition of a catalytic amount, 0.1 to 0.5 molar equivalents, of an iodide salt, such as sodium iodide, potassium iodide, or tetrabutyl ammonium iodide. The reaction is generally carried out at temperatures of from ambient temperature to the refluxing temperature of the solvent. Generally, the reactions require 1 to 72 hours. The product can be isolated and purified by techniques well known in the art, such as extraction, evaporation, trituration, chromatography, and recrystallization.

In Reaction Scheme A.1, optional step 3, a compound of formula (1) or a protected compound of formula (1) in which $R_4$ is hydrogen is modified to give a compound of formula (1) or a protected compound of formula (1) in which $R_4$ is not hydrogen. Also encompassed by Reaction Scheme A.1, optional step 3, a protected compound of formula (1) is deprotected to give a compound of formula (1).

A modification reaction encompasses the formation of amides and the alkylation of the benzimidazole nitrogen. The formation of amides from esters and acids is well known and appreciated in the art. The alkylation of a benzimidazole nitrogen using a suitable alkylating agent is well known and appreciated in the art.

For example, a compound of formula (1) in which $R_4$ is hydrogen is contacted with a suitable alkylating agent. A suitable alkylating agent is one which transfers a group $R_4$ as is desired in the final product of formula (1). Suitable alkylating agents include but are not limited to benzyl bromide, benzyl chloride, 4-methylbenzyl bromide, 4-methoxybenzyl chloride, benzyl bromide, benzyl chloride, 4-fluorobenzyl bromide, 4-fluorobenzyl chloride, 2-(chloromethyl)furan, 3-(chloromethyl)furan, 2-(bromomethyl)thiophene, 3-(chloromethyl)thiophene, 2-(chloromethyl)pyridine, 3-(chloromethyl)pyridine, 4-(chloromethyl)pyridine, 2-chloroethyl ethyl ether, 2-chloroethyl methyl ether, benzyl chloride, 4-methoxybenzyl chloride, ethyl chloroacetate, t-butyl bromoacetate, methyl bromoacetate, methyl iodide, ethyl iodide, propyl iodide, isopropyl iodide, butyl bromide, pentyl bromide, pentyl iodide, hexyl bromide, 2,2,2-trifluoroethyl bromide, 2,2,2-trifluoroethyl iodide, 2,2,2-trifluoroethyl trifluoromethanesulfonate, 4,4,4-trifluorobutyl bromide, phenoxyethyl chloride, 2-(4-fluorophenoxy)ethyl bromide, methyl 2-(chloromethyl)benzoate, methyl 3-(chloromethyl)benzoate, methyl 4-(chloromethyl) benzoate, ethyl 2-(chloromethyl)benzoate, propyl 2-(chloromethyl)benzoate, N,N-dimethyl-4-(chloromethyl) benzamide, iodoacetamide. The reaction is carried out in a suitable solvent, such as dioxane, tetrahydrofuran, tetrahydrofuran/water mixtures, acetone, or acetonitrile. The reaction is carried out in the presence of from 1.0 to 6.0 molar equivalents of a suitable base, such as sodium carbonate, sodium bicarbonate, potassium carbonate, potassium bicarbonate, triethylamine, 1,8-diazabicyclo[5.4.0] undec-7-ene, 1,5-diazabicyclo[4.3.0]non-5-ene, sodium hydride, potassium hydride, potassium bis(trimethylsilyl) amide, lithium bis(trimethylsilyl)amide, or diisopropylethylamine. The reaction is generally carried out at temperatures of from −78° C. to the refluxing temperature of the solvent. Generally, the reactions require 1 to 72 hours. The product can be isolated and purified by techniques well known in the art, such as extraction, evaporation, trituration, chromatography, and recrystallization.

An alkylation of a benzimidazole nitrogen encompasses the Michael addition using a,b-unsaturated electrophiles. A suitable alkylating agent is one which transfers a group $R_4$, as desired in the final product of formula (1) or a protected group $R_4$ which gives rise after deprotection to $R_4$ as desired in the final product of formula (1), such as acrylonitrile, methyl acrylate, t-butyl acrylate, methyl vinyl sulfone, phenyl vinyl sulfone, and the like. The reaction is carried out in a suitable solvent, such as tetrahydrofuran or diethyl ether. The reaction is carried out in the presence of from 1.0 to 6.0 molar equivalents of a suitable base, such as sodium hydride, potassium hydride, potassium bis(trimethylsilyl) amide, lithium bis(trimethylsilyl)amide, or sec-butyl lithium. The reaction is generally carried out at temperatures of from −78° C. to the refluxing temperature of the solvent. Generally, the reactions require 1 to 72 hours. The product can be isolated and purified by techniques well known in the art, such as extraction, evaporation, trituration, chromatography, and recrystallization.

A deprotection reaction, such as the removal of hydroxy protecting groups or hydrolysis of an ester, utilizing suitable protecting groups such as those described in *Protecting Groups in Organic Synthesis* by T. Greene is well known and appreciated in the art.

of structure 2b can be one in which the stereochemistry gives rise after resolution to stereochemistry as desired in the final product of formula (1) and R', R', and $Ar_1$ are as desired in the final product of formula (1). An appropriate aldehyde of structure 2b can also be one in which the stereochemistry and R' and R' are as desired in the final product of formula (1) and $Ar_1$ gives rise upon deprotection to $Ar_1$ as desired in the final product of formula (1). Alternately, an appropriate aldehyde of structure 2b can also be one in which the stereochemistry gives rise after resolution to stereochemistry as desired in the final product of formula (1), R' and R" are as desired in the final product of formula (1), and $Ar_1$ gives rise upon deprotection to $Ar_1$ as desired in the final product of formula (1).

An appropriate aldehyde of structure 2b can be prepared from a homologous alkene by formation of the cis-diol followed by oxidative cleavage, as described in *Bioorganic & Medicinal Chemistry Letters*, 3, 319–322 (1993) or by methods analogous thereto, such as described in *J. Am. Chem. Soc.* 104, 1737 (1982) and *Tet.*, 44, 5525 (1988) or by the action of ozone on a homologous alkene by methods well known in the art. An appropriate aldehyde of structure 2b

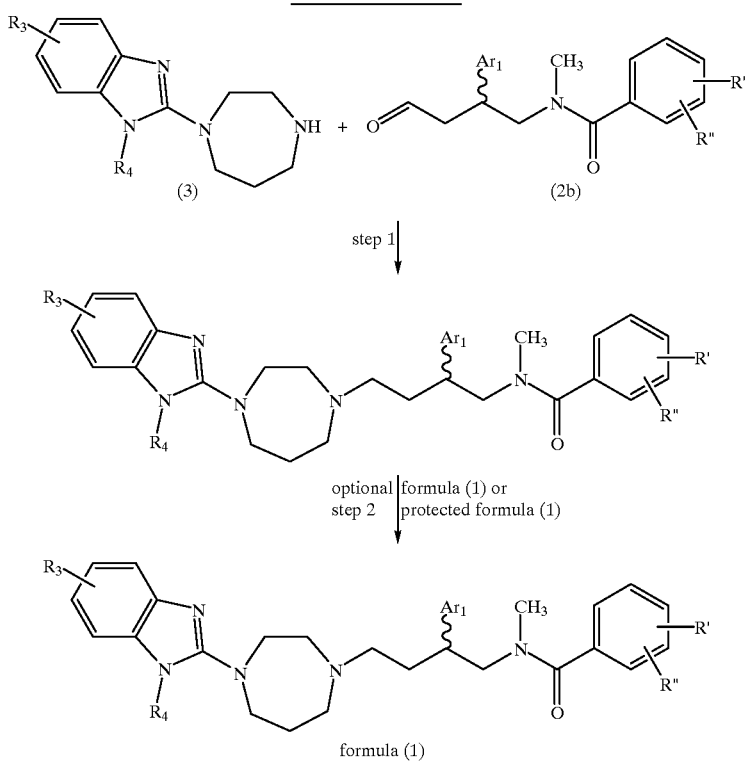

Reaction Scheme A.2

In Reaction Scheme A.2, step 1, an appropriate aldehyde of structure 2b reacts in an reductive amination with an appropriate piperidine of structure 3 or a salt thereof to give a protected compound of formula (1) or a compound of formula (1). Such reductive animation reactions are well known in the art, see *Bioorganic & Medicinal Chemistry Letters*, 3, 319–322 (1993) and *J. Am. Chem. Soc.*, 93 2897–2904 (1971).

An appropriate aldehyde of structure 2b is one in which the stereochemistry is as desired in the final product of formula (1) and R', R", and $Ar_1$ are as desired in the final product of formula (1). Alternately, an appropriate aldehyde can be prepared by oxidation of an alcohol of structure 2, such as by the method of Swern which is well known and appreciated in the art. An appropriate 4-(1H-benzimidazol-2-yl)[1,4]diazepane compound of structure 3 or salt thereof is one as described in Reaction Scheme A.1, step 2.

For example, an appropriate aldehyde of structure 2b is contacted with an appropriate 4-(1H-benzimidazol-2-yl)[1,4]diazepane compound of structure 3 or salt thereof to give a protected compound of formula (1) or a compound of formula (1). The reaction is carried out in a suitable solvent, such as methanol, ethanol, tetrahydrofuran, or mixtures of methanol or ethanol and tetrahydrofuran. The reaction may be carried out in the presence of a drying agent, such as sodium sulfate or molecular sieves. The reaction is carried out in the presence of from 1.0 to 6.0 molar equivalents of a suitable reducing agent, such as, sodium borohydride or sodium cyanoborohydride with sodium cyanoborohydride being preferred. It may be advantageous to allow Schiff base formation to proceed before addition of the suitable reducing agent. The reaction is generally carried out at temperatures of from 0° C. to the refluxing temperature of the solvent. Generally, the reactions require 1 to 72 hours. The product can be isolated and purified by techniques well known in the art, such as filtration, extraction, evaporation, trituration, chromatography, and recrystallization.

In Reaction Scheme A.2, optional step 2, a protected compound of formula (1) is deprotected or a compound of formula (1) or a protected compound of formula (1) in which $R_4$ is hydrogen is modified to give a compound of formula (1) or a protected compound of formula (1) in which $R_4$ is not hydrogen and then deprotected, as required, as described in Reaction Scheme A.1, optional step 3.

A general synthetic procedure for preparing the alcohols of structure 2 is set forth in Reaction Scheme B. The reagents and starting materials are readily available to one of ordinary skill in the art. In Scheme B, all substituents, unless otherwise indicated, are as previously defined.

In Reaction Scheme B. step 1, an appropriate nitrile of structure 5 is alkylated with an appropriate protected alcohol of structure 4 to give an 4-(protected-hydroxy)butyronitrile of structure 6.

An appropriate nitrile of structure 5 is one in which $Ar_1$ is as desired in the final product of formula (1) or $Ar_1$ gives rise after deprotection to $Ar_1$ as desired in the final product of formula (1). An appropriate protected alcohol of structure 4 is one in which the leaving group, $L_2$, can be displaced by an anion derived from an appropriate nitrile of structure 5. Suitable leaving groups include but are not limited to chloro, bromo, iodo, and mesylate with bromo and iodo being preferred. The selection and use of a suitable hydroxy protecting group, $Pg_1$, such as those described in *Protecting Groups in Organic Synthesis* by T. Greene are well known and appreciated in the art. The use of tetrahydropyran-2-yl and t-butyldimethylsilyl hydroxy protecting groups are generally preferred.

For example, the appropriate nitrile of structure 5 is contacted with 0.8 to 1.2 molar equivalents of the appropriate protected alcohol of structure 4 under phase transfer catalysis conditions. The reaction is carried out in the presence of a 2 to 10 fold molar excess of a suitable base, such as sodium hydroxide or potassium hydroxide. The reaction is carried out in a solvent, such as water, ethyl

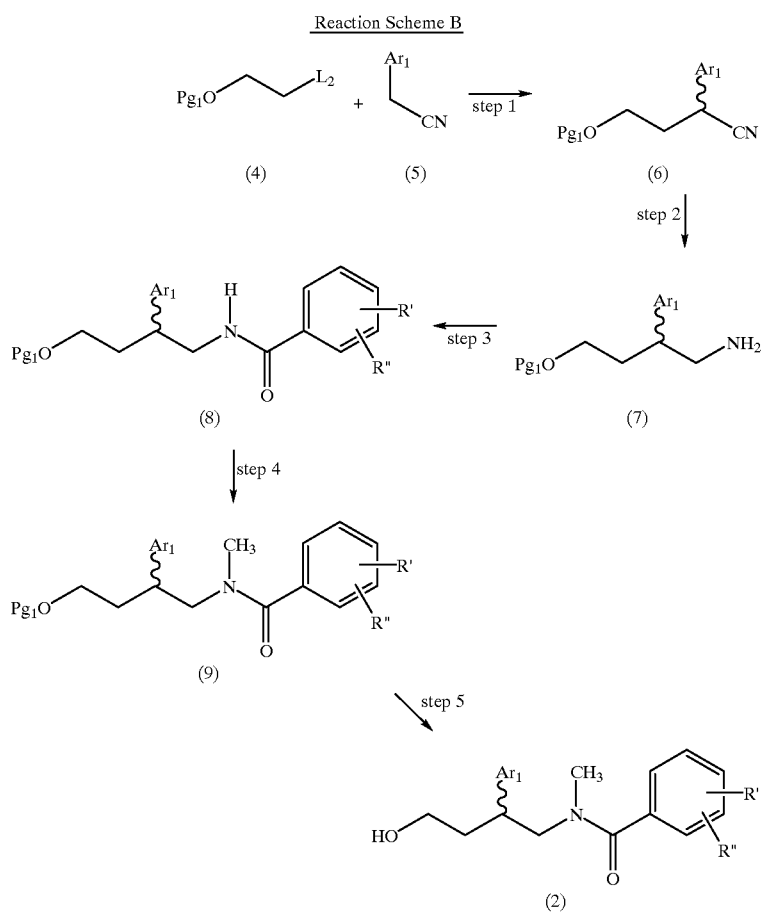

Reaction Scheme B acetate/water mixtures, dichloromethane/water mixtures, or tetrahydrofuran/water mixtures. The reaction is carried out in the presence of a suitable phase transfer catalyst, such as benzyltriethylammonium chloride, benzyltriethylammonium bromide, benzyltriethylammonium iodide, benzyltrimethylammonium chloride, benzyltributylammonium chloride, tetrabutylammonium chloride, tetrabutylammonium bromide, tetrabutylammonium iodide, tetrabutylammonium hydrogen sulfate, and the like. The reaction is generally carried out at temperatures of from −20° C. to 60° C. Generally, the reactions require 1 to 72 hours. The product can be isolated and purified by techniques well known in the art, such as extraction, evaporation, trituration, chromatography, and recrystallization.

Alternately, for example, the appropriate nitrile of structure 5 is contacted with 1.0 to 1.2 molar equivalents of the appropriate protected alcohol of structure 4. The reaction is carried out in the presence of an equimolar amount of a suitable base, such as sodium hydride, sodium bis(trimethylsilyl)amide, potassium bis(trimethylsilyl)amide, potassium t-butoxide, s-butyl lithium, and lithium diisopropylamide. The reaction is carried out in a solvent, such as dimethylformamide or tetrahydrofuran. The reaction is generally carried out at temperatures of from −78° C. to 0° C. Generally, the reactions require 1 to 72 hours. The product can be isolated and purified by techniques well known in the art, such as extraction, evaporation, distillation, trituration, chromatography, and recrystallization.

In Reaction Scheme B, step 2, the 4-(protected-hydroxy)butyronitrile of structure 6 is reduced to give an amino compound of structure 7.

For example, the 4-(protected-hydroxy)butyronitrile of structure 6 is contacted with an excess of an appropriate reducing agent, such as sodium borohydride in the presence of cobalt (II) chloride hexahydrate or hydrogen in the presence of a suitable catalyst, such as Raney nickel or platinum oxide. For compounds of structure 6 in which $Ar_1$ is thienyl and pyridyl, sodium borohydride in the presence of cobalt (II) chloride hexahydrate is preferred.

When sodium borohydride in the presence of cobalt chloride is used, the reaction is carried out in a suitable solvent, such as methanol, or ethanol. The reaction is generally carried out at temperatures of from 0° C. to 50° C. Generally, the reactions require 1 to 72 hours. The product can be isolated and purified by techniques well known in the art, such as extraction with aqueous acid, evaporation, trituration, distillation, chromatography, and recrystallization.

When Raney nickel is used, the reaction is carried out in a suitable solvent containing ammonia, such as ethanol/aqueous ammonium hydroxide or methanol/aqueous ammonium hydroxide. The reaction is generally carried out at temperatures of from ambient temperature to 70° C. The reaction is carried out with hydrogen at pressures of from 15 psi to 120 psi in an apparatus designed for carrying out reactions under pressure, such as a Parr hydrogenation apparatus. The product can be isolated by carefully removing the catalyst by filtration and evaporation. The product can be purified by extraction, evaporation, trituration, chromatography, and recrystallization.

When platinum oxide is used, the reaction is carried out in a suitable solvent such as ethanol, methanol, chloroform, ethanol/chloroform mixtures, or methanol/chloroform mixtures. The reaction is generally carried out at temperatures of from ambient temperature to 50° C. The reaction is carried out with hydrogen at pressures of from 15 psi to 120 psi in an apparatus designed for carrying out reactions under pressure, such as a Parr hydrogenation apparatus. Generally, an amine intermediate is obtained under these conditions and is isolated by carefully removing the catalyst by filtration and evaporation. Generally, the reaction requires 8 to 48 hours. The product can be purified by extraction, evaporation, trituration, chromatography, and recrystallization.

In Reaction Scheme B, step 3, the amino compound of structure 7 is benzoylated with an appropriate benzoylating agent to give a benzamide of structure 8. An appropriate benzoylating agent is an agent capable of transferring a benzoyl group or substituted benzoyl group, such as a benzoyl halide, substituted benzoyl halide, benzoyl anhydride, substituted benzoyl anhydride, benzoyl mixed anhydride, or substituted benzoyl mixed anhydride to give a benzamide of structure 8. An appropriate benzoylating agent gives a benzamide of structure 8 in which R' and R" are as desired in the final product of formula (1).

For example, the amino compound of structure 7 is contacted with 1 to 1.5 molar equivalents of an appropriate benzoylating agent. The reaction is carried out in a suitable solvent, such as dichloromethane, tetrahydrofuran, acetonitrile, dimethylformamide, or pyridine. The reaction is carried out in the presence of a base, such as sodium carbonate, sodium bicarbonate, triethylamine, N-methylmorpholine, diisopropylethylamine, or pyridine. The reaction is generally carried out at temperatures of from −20° C. to 50° C. Generally, the reactions require 1 to 6 hours. The product can be isolated and purified by techniques well known in the art, such as extraction, evaporation, trituration, chromatography, and recrystallization.

Alternately, for example, the amino compound of structure 7 is contacted with 1 to 1.5 molar equivalents of an appropriate benzoylating agent under Schotten-Baumann conditions. The reaction is carried out in a suitable solvent, such as ethyl acetate/water mixtures, acetone/water mixtures, tetrahydrofuran/water mixtures, or dichloromethane/water mixtures. The reaction is carried out in the presence of a base, such as sodium carbonate, sodium bicarbonate, potassium carbonate, potassium bicarbonate, or sodium hydroxide. The reaction is generally carried out at temperatures of from 0° C. to the refluxing temperature of the solvent. Generally, the reactions require 1 to 6 hours. The product can be isolated and purified by techniques well known in the art, such as extraction, evaporation, trituration, chromatography, and recrystallization.

In Reaction Scheme B, step 4, a benzamide of structure 8 is methylated with an appropriate methylating agent to give a N-methylbenzamide of structure 9. An appropriate methylating agent is one that transfers a methyl to a benzamide of structure 8, including iodomethane, bromomethane, dimethylsulfate, trimethyloxonium tetrafluoroborate, and the like.

For example, a benzamide of structure 8 is contacted with 1 to 4 molar equivalents of the appropriate methylating agent. The reaction is carried out in the presence of from 1 to 4 molar equivalents of a suitable base, such as sodium hydride, sodium bis(trimethylsilyl)amide, potassium t-butoxide, n-butyllithium, sec-butyl lithium, and lithium diisopropylamide with sodium hydride and sodium bis(trimethylsilyl)amide being preferred. The reaction is carried out in a solvent, such as dimethylformamide or tetrahydrofuran. The reaction is generally carried out at temperatures of from −20° C. to 60° C. Generally, the reactions require 1 to 72 hours. The product can be isolated and purified by techniques well known in the art, such as extraction, evaporation, trituration, chromatography, and recrystallization.

In Reaction Scheme B, step 5, the N-methylbenzamide of structure 9 is deprotected to give an alcohol of structure 2.

A deprotection reaction, such as the removal of hydroxy protecting groups utilizing suitable protecting groups such as those described in *Protecting Groups in Organic Synthesis* by T. Greene is well known and appreciated in the art.

The following examples and preparations present typical syntheses of the compounds of formula (1). These examples are understood to be illustrative only and are not intended to limit the scope of the invention in any way.

PREPARATION 1.1

Synthesis of 4-(1-(2-ethoxyethyl)-1H-benzimidazol-2-yl)[1,4]diazepane

According to the method of R. Iemura et al., *J. Med. Chem.*, 29 1178–1183 (1986), combine 1-chloro-2-nitrobenzene (69.0 g, 440 mmol) and 2-aminoethyl ethyl ether (102.5 g, 1.15 mol) and heat to reflux. After 18 hours, cool and dilute the reaction mixture with ethyl acetate (400 mL). Extract with brine. Dry the organic layer over $Na_2SO_4$, filter, and evaporate in vacuo to give a residue. Chromatograph the residue on silica gel eluting with dichloromethane to give N-(2-ethoxyethyl)-2-nitroaniline.

Combine N-(2-ethoxyethyl)-2-nitroaniline (85.4 g, 406 mmol) and ethanol (300 mL). Add a solution of sodium hydroxide (6 g) in water (60 mL). Heat to reflux. Remove the heating and add portionwise zinc metal (106 g, 1.62 mol) at a rate such that the reaction is maintained at reflux. After the addition of zinc metal is complete stir for 30 minutes. Filter the reaction mixture and rinse with water. Extract the filtrate three times with ethyl acetate. Dry the combined organic layers over $Na_2SO_4$, filter, and evaporate in vacuo to give a residue. Chromatograph the residue on silica gel eluting with ethyl acetate to give 1-(2-ethoxyethyl)-1,2-phenylenediamine.

Combine 1-(2-ethoxyethyl)-1,2-phenylenediamine (55.4 g, 307 mmol) and urea (37.5 g, 624 mmol). Heat at 150° C. After 5 hour, cool to ambient temperature and stir. After 18 hours, partition the reaction mixture between ethyl acetate and water. Separate the layers and extract the aqueous layer three times with ethyl acetate. Combine the organic layers and extract with aqueous 1 M hydrochloric acid solution. Dry the organic layer over $Na_2SO_4$, filter, and evaporate in vacuo to give a residue. Chromatograph the residue on silica gel eluting with dichloromethane to give the 2-hydroxy-1-(2-ethoxyethyl)-1H-benzimidazole.

Combine 2-hydroxy-1-(2-ethoxyethyl)-1H-benzimidazole (36.4 g, 177 mmol) and phosphorous oxychloride (72 mL) and reflux. After 30 minutes, cool to ambient temperature and pour the reaction mixture onto crushed ice. Adjust the pH to about 9 using aqueous 50% sodium hydroxide solution. Extract three times with ethyl acetate. Combine the organic layers and extract with brine. Dry the organic layer over $Na_2SO_4$, filter, and evaporate in vacuo to give a residue. Chromatograph the residue on silica gel eluting with ethyl acetate to give the 2-chloro-1-(2-ethoxyethyl)-1H-benzimidazole.

Combine 2-chloro-1-(2-ethoxyethyl)-1H-benzimidazole (12.2 g, 54.2 mmol) and [1,4]diazepane (11.34 g, 113 mmol), 1,8-diazabicyclo[5.4.0]undec-7-ene (9 mL), and pyridine (90 mL). Heat to reflux. After 18 hours, cool to ambient temperature and evaporate in vacuo to give a residue. Partition the residue between aqueous 1 M sodium hydroxide solution and ethyl acetate. Separate the layers and extract the aqueous layer two times with ethyl acetate. Combine the organic layers, dry over $Na_2SO_4$, filter, and evaporate in vacuo to give a residue. Chromatograph the residue on silica gel eluting sequentially with 30% methanol/ethyl acetate and then 2% concentrated aqueous ammonia/methanol to give the title compound: $R_f$=0.26 (silica gel, 2% concentrated aqueous ammonia/methanol).

Alternately, combine 2-chloro-1-(2-ethoxyethyl)-1H-benzimidazole (15.56 g, 69.3 mmol) and [1,4]diazepane (13.89 g, 138.7 mmol), 1,8-diazabicyclo[5.4.0]undec-7-ene (12.34 mL, 83.1 mmol), and pyridine (200 mL). Heat to reflux. After 18 hours, cool to ambient temperature and evaporate in vacuo to give a residue. Partition the residue between aqueous 1 M sodium hydroxide solution and dichloromethane. Separate the layers and extract the aqueous layer two times with dichloromethane. Combine the organic layers, extract with aqueous 1 M sodium hydroxide solution, water, and then brine. Dry the organic layer over $Na_2SO_4$, filter, and evaporate in vacuo to give a residue. Chromatograph the residue on silica gel eluting with 2% concentrated aqueous ammonia/methanol to give the title compound: $R_f$=0.26 (silica gel, 2% concentrated aqueous ammonia/methanol).

PREPARATION 1.2

Synthesis of 4-(1-(2-ethoxyethyl)-1H-benzimidazol-2-yl)[1,4]diazepane

Combine 2-chloro-1H-benzimidazole (21.1.4 g, 138.4 mmol) and dimethylformamide (200 mL). Add portionwise, sodium hydride (24.0 g, 60% in oil, 153.3 mmol). After 15 minutes, add 2-chloroethyl ethyl ether (21.9 g, 201,5 mmol). Heat to 60° C. After 18 hours, cool the reaction mixture and dilute with ethyl acetate. Extract with a saturated aqueous sodium bicarbonate solution, water, and then brine. Dry the organic layer over $MgSO_4$, filter, and evaporate in vacuo to give a residue. Chromatograph the residue on silica gel eluting sequentially with 10% ethyl acetate/hexane and then 30% ethyl acetate hexane to give the 2-chloro-1-(2-ethoxyethyl)-1H-benzimidazole: $R_f$=0.74 (silica gel, 7/3 ethyl acetate/hexane).

Combine 2-chloro-1-(2-ethoxyethyl)-1H-benzimidazole (22.3 g, 99.4 mmol), 1-methyl[1,4]diazepane (19 mL, 152.8 mmol), and triethylamine (75 mL). Heat to 70° C. After 18 hours, add 1-methyl[1,4]diazepane (10 mL) and continue to heat at reflux. After 96 hours, cool to ambient temperature and partition the reaction mixture between water and ethyl acetate. Separate the layers and extract the organic layer with a saturated aqueous sodium bicarbonate solution and then brine. Dry the organic layer over $MgSO_4$, filter, and evaporate in vacuo to give a residue. Chromatograph the residue on silica gel eluting sequentially with 50% ethyl acetate/hexane and then 10% methanol/dichloromethane to give 1-methyl-4-(1-(2-ethoxyethyl)-1H-benzimidazol-2-yl)[1,4]diazepane: $R_f$=0.52 (silica gel, dichloromethane/methanol/concentrated aqueous ammonia, 90/10/0.1).

Combine 1-methyl-4-(1-(2-ethoxyethyl)-1H-benzimidazol-2-yl)[1,4]diazepane (1.79 g, 5.9 mmol) and ethyl chloroformate (0.75 mL, 7.8 mmol) in toluene (20 mL). Heat to 80° C. After 2 hours, cool the reaction mixture and dilute with ethyl acetate. Extract with a saturated aqueous sodium bicarbonate solution, dry the organic layer over $MgSO_4$, filter, and evaporate in vacuo to give 1-ethoxycarbonyl-4-(1-(2-ethoxyethyl)-1H-benzimidazol-2-yl)[1,4]diazepane: $R_f$=0.87 (silica gel, dichloromethane/methanol, 90/10). Combine 1-ethoxycarbonyl-4-(1-(2-ethoxyethyl)-1H-benzimidazol-2-yl)[1,4]diazepane (17.2 g, 47.6 mmol), hydrazine hydrate (40 mL), and potassium hydroxide (40.7 g, 725 mmol) in ethylene glycol (150 mL).

Heat to reflux. After 5 hours, cool the reaction mixture and dilute with water (500 mL). Extract three times with dichloromethane. Combine the dichloromethane layers and extract with a saturated aqueous sodium bicarbonate solution and then brine. Dry the organic layer over $MgSO_4$, filter, and evaporate in vacuo to give the title compound: $R_f$=0.25 (silica gel, dichloromethane/methanol, 90/10).

PREPARATION 2

Synthesis of 4-(1-(2-ethoxyethyl)-1H-benzimidazol-2-yl)[1,4]diazepane hydriodic acid salt Combine 4-(1-(2-ethoxyethyl)-1H-benzimidazol-2-yl)[1,4]diazepane (1.30 g), 48% hydriodic acid (10 mL), ethanol (10 mL), and diethyl ether (80 mL) and stir. After 30 minutes add diethyl ether, (800 mL) and continue to stir to give a solid. Collect the solid by filtration and dry in vacuo to give the title compound: mp; 156–163° C.

PREPARATION 3

Synthesis of 1-(t-butyldimethylsilyloxy)-2-bromoethane

Combine imidazole (59.9 g, 880 mmol), t-butyldimethylsilyl chloride (60.3 g, 400 mmol), and dimethylformamide (300 mL). Cool to 0° C. in a salt-ice bath. Add dropwise 2-bromoethanol (50.0 g, 400 mmol) at such a rate that the temperature of the reaction mixture does not rise above 0° C. After 2 hours, warm to ambient temperature. After 18 hours, extract the reaction mixture three times with hexane. Combine the hexane layers and extract three times with a saturated aqueous solution of ammonium chloride, three times with a saturated aqueous solution of sodium bicarbonate, and then brine. Dry the organic layer over $Na_2SO_4$, filter, and evaporate in vacuo to give the title compound.

PREPARATION 4

Synthesis of 1-(t-butyldimethylsilyloxy)-2-iodoethane

Prepare by the method of Preparation 3 using 2-iodoethanol to give the title compound.

EXAMPLE 1

N-Methyl-N-(4-(4-(1-(2-ethoxyethyl)-1H-benzimidazol-2-yl)[1,4diazepan-1-yl)-2-(4-fluorophenyl)butyl)-3,4,5-trimethoxybenzamide 1.1.1 Synthesis of 2-(4-fluorophenyl)-4-(t-butyldimethylsilyloxy)butyronitrile As adapted from the procedure of *Org. Syn. Collective Volume VI*, 897–900 (1988), combine 4-fluorophenylacetonitrile (56.5 g, 418 mmol), an aqueous 50% sodium hydroxide solution (106.3 g, 1330 mmol), and benzyltriethylammonium chloride (0.95 g) in water (100 mL). Warm to about 30° C. and stir vigorously. Add dropwise over about 30 minutes 1-(t-butyldimethylsilyloxy)-2-bromoethane (50 g, 209 mmol). When the addition is complete, warm to about 40° C. and continue to stir vigorously. After 18 hours, dilute the reaction mixture with ethyl acetate and stir. After 30 minutes, separate the organic layer and extract three times with aqueous saturated ammonium chloride solution, two times with an aqueous saturated sodium bicarbonate solution, and then brine. Dry the organic layer over $Na_2SO_4$, filter, and concentrate in vacuo to give a residue. Distill the residue to give the title compound: bp; 100–115° C. at 0.2 mm Hg. $R_f$=0.35 (silica gel, 1/1 dichloromethane/hexane).

1.1.2 Synthesis of 2-(4-fluorophenyl)-4-(t-butyldimethylsilyloxy)butyronitrile

Combine 4-fluorophenylacetonitrile (5.0 g, 37.0 mmol), and tetrahydrofuran (45 mL). Cool to about –65° C. using a dry-ice/acetone bath. Add a solution of potassium bis(trimethylsilyl)amide (89 mL, 0.5 M in toluene, 44.5 mmol). After 1 hour, add a solution of 1-(t-butyldimethylsilyloxy)-2-iodoethane (12.7 g, 44.4 mmol) in tetrahydrofuran (10 mL). After the addition of 1-(t-butyldimethylsilyloxy)-2-iodoethane is complete, warm to ambient temperature. After 18 hours, dilute the reaction mixture with tetrahydrofuran and extract three times with aqueous saturated ammonium chloride solution and then twice with brine. Dry the organic layer over $Na_2SO_4$, filter, and concentrate in vacuo to give a residue. Chromatograph the residue on silica gel eluting with 1/1 dichloromethane/hexane to give the title compound.

1.1.3 Synthesis of 2-(4-fluorophenyl)-4-(t-butyldimethylsilyloxy)butyronitrile

Combine 4-fluorophenylacetonitrile (1.0 g, 7.4 mmol), and tetrahydrofuran (9 mL). Cool to about –70° C. using a dry-ice/acetone bath. Add a solution of potassium bis(trimethylsilyl)amide (14.8 mL, 0.5 M in toluene, 7.4 mmol). After 2 hours, add, via cannula, the solution prepared above to a cooled (–25° C.) solution of 1-(t-butyldimethylsilyloxy)-2-iodoethane (2.1 g, 7.4 mmol) in tetrahydrofuran (4 mL). After the addition to 1-(t-butyldimethylsilyloxy)-2-iodoethane is complete, warm to ambient temperature. After 18 hours, dilute the reaction mixture with tetrahydrofuran and extract three times with

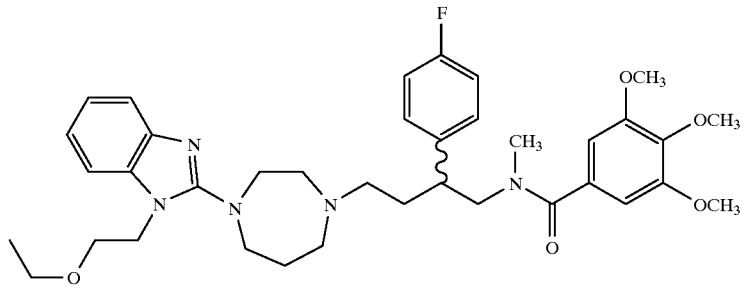

aqueous saturated ammonium chloride solution and then twice with brine. Dry the organic layer over $Na_2SO_4$, filter,

1.1.4 Synthesis of 2-(4-fluorophenyl)-4-(t-butyldimethylsilyloxy)butyronitrile Combine 4-fluorophenylacetonitrile (1.0 g, 7.4 mmol), and tetrahydrofuran (20 mL). Cool to about −70° C. using a dry-ice/acetone bath. Add a solution of s-butyl lithium (6.3 mL, 1.3 M in cyclohexane, 8.1 mmol). After 1 hour, add a solution of 1-(t-butyldimethylsilyloxy)-2-iodoethane (2.1 g, 7.4 mmol) in tetrahydrofuran (4 mL). After 2 hours, warm to ambient temperature. After 18 hours, dilute the reaction mixture with ethyl acetate and extract twice with aqueous saturated ammonium chloride solution and then twice with brine. Dry the organic layer over $Na_2SO_4$, filter, and concentrate in vacuo to give a residue. Chromatograph the residue on silica gel eluting with 1/1 dichloromethane/hexane to give the title compound.

1.2 Synthesis of 2-(4-fluorophenyl)-4-(t-butyldimethylsilyloxy)butylamine

Combine 2-(4-fluorophenyl)-4-(t-butyldimethylsilyloxy)butyronitrile (43.0 g, 146.5 mmol) and ethanol (200 mL) in a Parr bottle. Add Raney nickel (129 g) to the reaction mixture. Add a solution of concentrated ammonium hydroxide (40 mL). Hydrogenate on a Parr shaker at 50 psi. After 24 hours, filter through a celite pad and rinse the solids with ethanol. Concentrate the filtrate in vacuo to give the title compound.

1.3 Synthesis of N-(2-(4-fluorophenyl)-4-(t-butyldimethylsilyloxy)butyl)-3,4,5-trimethoxybenzamide Combine 2-(4-fluorophenyl)-4-(t-butyldimethylsilyloxy)butylamine (7.33 g, 24.6 mmol) and sodium carbonate (2.61 g, 24.6 mmol) in 4/1 ethyl acetate/water (400 mL). Cool the reaction mixture to 0° C. with a salt-ice bath. Slowly, add a solution of 3,4,5-trimethoxybenzoyl chloride (5.96, 25.9 mmol) in ethyl acetate (50 mL) at such a rate that the temperature of the reaction mixture does not rise above 5° C. After 2 hours, warm to ambient temperature. After 18 hours, separate the layers and extract the organic layer twice with a saturated aqueous solution of ammonium chloride, twice with a saturated aqueous solution of sodium bicarbonate and then with brine. Dry the organic layer over $Na_2SO_4$, filter, and concentrate in vacuo to obtain a residue. Chromatograph the residue on silica gel eluting with 50% ethyl acetate/hexane to give, after drying, the title compound: mp; 113–114° C. Elemental Analysis calculated for $C_{26}H_{38}FNO_3Si$: C 63.51; H 7.79; N 2.85; Found: C 63.43; H 7.51; N 2.66. $R_f$=0.30 (silica gel, 50% ethyl acetate/hexane).

1.4 Synthesis of N-methyl-N-(2-(4-fluorophenyl)-4-(t-butyldimethylsilyloxy)butyl)-3,4,5-trimethoxybenzamide Combine hexane washed sodium hydride (0.48 g, 50% in oil, 10.0 mmol) and dimethylformamide (5 mL). Cool the reaction mixture to 0° C. with a salt-ice bath. Slowly, add a solution of N-(2-(4-fluorophenyl)-4-(t-butyldimethylsilyloxy)butyl)-3,4,5-trimethoxybenzamide (4.0 g, 8.1 mmol) in dimethylformamide (10 mL). Stir until gas evolution ceases. Add iodobutane (0.62 mL, 10.0 mmol). After 16 hours, dilute the reaction mixture with ethyl acetate and extract three times with water and then brine. Dry the organic layer over $Na_2SO_4$, filter, and concentrate in vacuo to give a residue. Chromatograph the residue on silica gel eluting with 1/1 ethyl acetate/hexane to give, after drying, the title compound: $R_f$=0.15 (silica gel, 1/1 ethyl acetate/hexane). Elemental Analysis calculated for $C_{27}H_{40}FNO_3Si$: C 64.13; H 7.97; N 2.77; Found: C 63.73; H 7.90; N 2.88.

1.5 Synthesis of N-methyl-N-(2-(4-fluorophenyl)-4-hydroxybutyl)-3,4,5-trimethoxybenzamide Combine N-methyl-N-(2-(4-fluorophenyl)-4-(t-butyldimethylsilyloxy)butyl)-3,4,5-trimethoxybenzamide (3.9 g, 7.65 mmol) and methanol (40 mL). Add ammonium fluoride (1.71 g, 46.0 mmol). Heat to reflux. After 20 hours, concentrate in vacuo to give a residue. Combine the residue with water and dichloromethane. Separate the layers and extract the aqueous layer twice with dichloromethane. Combine the organic layers and dry over $Na_2SO_4$, filter, and concentrate in vacuo to give the title compound: mp; 30–35° C. $R_f$=0.30 (silica gel, 10/1 ethyl acetate/methanol).

1.6 Synthesis of N-methyl-N-(2-(4-fluorophenyl)-4-methanesulfonylbutyl)-3,4,5-trimethoxybenzamide Combine N-methyl-N-(2-(4-fluorophenyl)-4-hydroxybutyl)-3,4,5-trimethoxybenzamide (2.5 g, 6.36 mmol), diisopropylethylamine (2.4 mL, 14.0 mmol), and anhydrous dichloromethane (25 mL). Cool the reaction mixture to 0° C. with an ice bath. Slowly, add methanesulfonyl chloride (0.69 mL, 8.9 mmol). After 1 hour, dilute the reaction mixture with dichloromethane and extract 3 times with aqueous 1M hydrochloric acid solution, 2 times with a saturated solution of sodium bicarbonate, and then brine. Dry the organic layer over $Na_2SO_4$, filter, and concentrate in vacuo to obtain the title compound: $R_f$=0.43 (silica gel, 10/1 ethyl acetate/methanol).

1.7 Synthesis of N-methyl-N-(4-(4-(1-(2-ethoxyethyl)-1H-benzimidazol-2-yl)[1,4]diazepan-1-yl)-2-(4-fluorophenyl)butyl)-3,4,5-trimethoxybenzamide Combine N-methyl-N-(2-(4-fluorophenyl)-4-methanesulfonylbutyl)-3,4,5-trimethoxybenzamide (0.53 g, 1.17 mmol), diisopropylethylamine (1.22 mL, 7.0 mmol), and 4-(1-(2-ethoxyethyl)-1H-benzimidazol-2-yl)[1,4]diazepane hydriodic acid salt (0.96 g, 1.76 mmol) in acetonitrile (20 mL). Heat to reflux. After 18 hours, cool the reaction mixture, dilute with ethyl acetate, and extract with a saturated solution of sodium bicarbonate and then brine. Dry the organic layer over $Na_2SO_4$, filter, and concentrate in vacuo to obtain a residue. Chromatograph the residue on silica gel eluting with 1/2 ethyl acetate/methanol to give, after drying, the title compound: $R_f$=0.25 (silica gel, 2/1 ethyl acetate/methanol).

1.8 Synthesis of N-methyl-N-(4-(4-(1-(2-ethoxyethyl)-1H-benzimidazol-2-yl)[1,4]diazepan-1-yl)-2-(4-fluorophenyl)butyl)-3,4,5-trimethoxybenzamide methanesulfonic acid salt Combine N-methyl-N-(4-(4-(1-(2-ethoxyethyl)-1H-benzimidazol-2-yl)[1,4]diazepan-1-yl)-2-(4-fluorophenyl)butyl)-3,4,5-trimethoxybenzamide (0.52 g, 0.79 mmol) and 10% methanol/ethyl acetate (22 mL). Add methanesulfonic acid (0.12 mL, 1.7 mmol) and stir. After 18 hours, concentrate the reaction mixture in vacuo to give a residue. Triturate the residue with diethyl ether to give a solid. Twice, decant the solvent and add more diethyl ether. Decant the solvent and cool to 0° C. After 18 hours, collect the solid and dry to give the title compound: mp; 60–70° C.

PREPARATION 5

Synthesis of 1-(tetrahydropyran-2-yloxy)-2-bromoethane

Combine 2-bromoethanol (14.2 mL, 200 mmol) and dihydropyrane (18.25 mL, 200 mmol) in dichloromethane (20 mL). Add pyridinium p-toluenesulfonic acid (5 g, 20 mmol). After 2.5 hours, dilute the reaction mixture with diethyl ether and extract with water, 1/1 water/brine, water, and then brine. Dry the organic layer over $MgSO_4$, filter, and evaporate in vacuo to give a residue. Distill the residue to give the title compound: bp; 80–90° C. at 15–20 mm Hg.

EXAMPLE 2

N-Methyl-N-(4-(4-(1-(2-ethoxyethyl)-1H-benzimidazol-2-yl)[1,4]diazepan-1-yl)-2-(3,4-dichlorophenyl)butyl)-benzamide

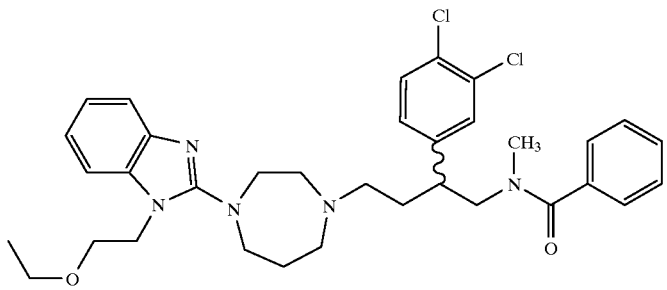

2.1 Synthesis of 2-(3,4-dichlorophenyl)-4-(tetrahydropyran-2-yloxy)butyronitrile Combine sodium hydride (1.2 g, 50 mmol) and tetrahydrofuran (20 mL). Add dropwise a solution of 3,4-dichlorophenylacetonitrile (8.9 g, 47.8 mmol) in tetrahydrofuran (50 mL) at about 0° C. When the addition is complete, allow to warm to ambient temperature and stir. After 2.5 hours, cool to 0° C. and add 1-(tetrahydropyran-2-yloxy)-2-bromoethane (10.0 g, 47.9 mmol). Warm to ambient temperature. After 16 hours, pour the reaction mixture into saturated ammonium chloride and extract with diethyl ether. Separate the organic layer and extract with water and brine. Dry the organic layer over MgSO$_4$, filter and concentrate in vacuo to give a residue. Chromatograph the residue on silica gel eluting sequentially with 5% ethyl acetate/hexane, 10% ethyl acetate/hexane, and 20% ethyl acetate in hexane to give the title compound.

2.2 Synthesis of 2-(3,4-dichlorophenyl)-4-(tetrahydropyran-2-yloxy)butylamine

Combine 2-(3,4-dichlorophenyl)-4-(tetrahydropyran-2-yloxy)butyronitrile (7 g) and ethanol (20 mL) in a Parr bottle. Add Raney nickel (1 g) to the reaction mixture. Add a solution of concentrated ammonium hydroxide (3.5 mL). Hydrogenate on a Parr shaker at 50 psi. After 24 hours, filter through a celite pad and rinse the solids with ethanol. Concentrate the filtrate in vacuo to obtain a residue. Chromatograph the residue in vacuo on silica gel eluting sequentially with 50% ethyl acetate/hexane and 10% methanol/dichloromethane to give the title compound.

2.3 Synthesis of N-(2-(3,4-dichlorophenyl)-4-(tetrahydropyran-2-yloxy)butyl)benzamide Combine 2-(3,4-dichlorophenyl)-4-(tetrahydropyran-2-yloxy)butylamine (3.05 g, 9.6 mmol) and N-methylmorpholine (2.2 mL, 20 mmol) in anhydrous dichloromethane (25 mL). Cool the reaction mixture to 0° C. with a salt-ice bath. Slowly, add benzoyl chloride (1.2 mL, 10.3 mmol). After 1 hour, extract the reaction mixture with a saturated solution of sodium bicarbonate and then water. Dry the organic layer over MgSO$_4$, filter, and concentrate in vacuo to obtain a residue. Chromatograph the residue on silica gel eluting sequentially with 35% ethyl acetate/hexane and then with 50% ethyl acetate/hexane to give the title compound.

2.4 Synthesis of N-methyl-N-(2-(3,4-dichlorophenyl)-4-(tetrahydropyran-2-yloxy)butyl)benzamide Combine N-(2-(3,4-dichlorophenyl)-4-(tetrahydropyran-2-yloxy)butyl)benzamide (3.84 g) and tetrahydrofuran (20 mL). Add sodium hydride (0.28 g, 11.5 mmol) and stir until gas evolution ceases. Add iodomethane (1.5 mL, 24.1 mmol). After 6 hours, dilute the reaction mixture with diethyl ether and extract with a saturated solution of ammonium chloride. Separate the organic layer and extract with sodium bisulfite solution, water, and brine. Dry the organic layer over MgSO$_4$, filter, and concentrate in vacuo to give the title compound.

2.5 Synthesis of N-methyl-N-(2-(3,4-dichlorophenyl)-4-hydroxybutyl)benzamide

Combine N-methyl-N-(2-(3,4-dichlorophenyl)-4-(tetrahydropyran-2-yloxy)butyl)benzamide (3.7 g) and methanol (30 mL). Add p-toluenesulfonic acid hydrate (0.73 g) and stir. After 18 hours, concentrate in vacuo to give a residue. Combine the residue and dichloromethane and extract with a saturated solution of sodium bicarbonate and then water. Dry the organic layer over MgSO$_4$, filter, and concentrate in vacuo to obtain a residue. Chromatograph the residue on silica gel eluting sequentially with 50% ethyl acetate/hexane and then ethyl acetate to give the title compound.

2.6 Synthesis of N-methyl-N-(2-(3,4-dichlorophenyl)-4-methanesulfonylbutyl)benzamide Combine N-methyl-N-(2-(3,4-dichlorophenyl)-4-hydroxybutyl)benzamide (0.5 g), diisopropylethylamine (0.3 mL, 1.7 mmol), and anhydrous dichloromethane (8 mL). Cool the reaction mixture to 0° C. with an ice bath. Slowly, add methanesulfonyl chloride (0.13 mL, 1.7 mmol). Warm to ambient temperature. After 18 hours, quench the reaction by the addition of ice. Separate the organic layer and extract 3 times with 1M hydrochloric acid solution and 2 times with a saturated solution of sodium bicarbonate. Dry the organic layer over Na$_2$SO$_4$, filter, and concentrate in vacuo to obtain the title compound.

2.7 Synthesis of N-Methyl-N-(4-(4-(1-(2-ethoxyethyl)-1H-benzimidazol-2-yl)[1,4]diazepan-1-yl)-2-(3,4-dichlorophenyl)butyl)benzamide Prepare by the method of Example 1.7 using N-methyl-N-(2-(3,4-dichlorophenyl)-4-methanesulfonylbutyl)benzamide and 4-(1-(2-ethoxyethyl)-1H-benzimidazol-2-yl)[1,4]diazepane hydriodic acid salt to give the title compound.

PREPARATION 6.1

Synthesis of 4-(1-(5-hydroxymethylfur-2-ylmethyl)-1H-benzimidazol-2-yl)[1,4]diazepane Combine 2-chlorobenzimidazole (10.0 g, 66 mmol), and dimethylformamide (100 mL). Add portionwise sodium hydride (1.63 g, 68 mmol). After the evolution of gas ceases, add a solution of ethyl 2-chloromethyl-5-furoate (12.45 g, 0.66 mmol) in dimethylformamide (20 mL). After 18 hours, dilute the reaction mixture with water and extract four times with diethyl ether. Combine the organic layers and extract with water and then brine. Dry the organic layer over $Na_2SO_4$, filter, and evaporate in vacuo to give a residue. Chromatograph the residue eluting with 5% methanol/0.2% concentrated aqueous ammonia solution/dichloromethane to give 2-chloro-1-(5-ethyoxycarbonylfur-2-ylmethyl)-1H-benzimidazole.

Combine 2-chloro-1-(5-ethyoxycarbonylfur-2-ylmethyl)-1H-benzimidazole (9.50 g, 31.2 mmol) and [1,4]diazepane (6.24 g, 62.3 mmol), 1,8-diazabicyclo[5.4.0]undec-7-ene (5.6 mL, 37.4 mmol), and pyridine (90 mL). Heat to reflux. After 18 hours, cool to ambient temperature and evaporate in vacuo to give a residue. Chromatograph the residue on silica gel eluting sequentially with methanol and then 2% concentrated aqueous ammonia/methanol to give 4-(1-(5-ethyoxycarbonylfur-2-ylmethyl)-1H-benzimidazol-2-yl)[1,4]diazepane. Combine 4-(1-(5-ethyoxycarbonylfur-2-ylmethyl)-1H-benzimidazol-2-yl)[1,4]diazepane (1.0 g, 2.7 mmol) and tetrahydrofuran (10 mL). Add a solution of lithium aluminum hydride (2.7 mL, 1.0 M in tetrahydrofuran, 2.7 mmol). After 18 hours pour the reaction mixture into a beaker, dilute with dichloromethane, and cool to 0° C. With stirring add portionwise, Glauber's salt ($Na_2SO_4.10H_2O$) until the evolution of gas ceases. Add dichloromethane to about double the volume, add celite, stir to form a thick slurry, and filter. Evaporate the filtrate in vacuo to give the title compound.

PREPARATION 6.2

Synthesis of 4-(1-(5-hydroxymethylfur-2-ylmethyl)-1H-benzimidazol-2-yl)[1,4]diazepane Combine 1-ethoxycarbonyl-4-(1H-benzimidazol-2-yl)[1,4]diazepane (10 mmol) and sodium hydride (10 mmol) in dimethylformamide (20 mL). After gas evolution ceases, add ethyl 5-chloromethyl-2-furoate (10 mmol) and stir. After 3 days, evaporate in vacuo to give a residue. Combine the residue and ethyl acetate. Extract with water and brine. Dry the organic layer over $Na_2SO_4$, filter, and evaporate in vacuo to give 1-ethoxycarbonyl-4-(1-(5-(ethoxycarbonyl)fur-2-ylmethyl)-1H-benzimidazol-2-yl)[1,4]diazepane.

Combine 1-ethoxycarbonyl-4-(1-(5-(ethoxycarbonyl)fur-2-ylmethyl)-1H-benzimidazol-2-yl)[1,4]diazepane (5 mmol) and lithium aluminum hydride (5 mmol) in tetrahydrofuran. Heat to reflux. After 12 hour, cool and carefully quench the reaction mixture with 10% aqueous ammonium chloride solution. Extract the reaction mixture with ethyl acetate. Dry the organic layer over $Na_2SO_4$, filter, and evaporate in vacuo to give 1-ethoxycarbonyl-4-(1-(5-hydroxymethylfur-2-ylmethyl)-1H-benzimidazol-2-yl)[1,4]diazepane.

Alternatively, combine 4-(1-(5-(ethoxycarbonyl)fur-2-ylmethyl)-1H-benzimidazol-2-yl)[1,4]diazepane (1.0 g, 2.7 mmol) and tetrahydrofuran (10 mL). Add a solution of lithium aluminum hydride in tetrahydrofuran (2.7 mL, 1 M, 2.7 mmol). After 18 hour, quench by slow portionwise addition of Glauber's salt ($Na_2SO_4.10H_2O$) until gas evolution ceases. Add dichloromethane (20 mL) and celite and stir. Filter and evaporate in vacuo to give the title compound.

Combine 1-ethoxycarbonyl-4-(1-(5-hydroxymethylfur-2-ylmethyl)-1H-benzimidazol-2-yl)[1,4]diazepane (4 mmol) and sodium hydroxide (8 mmol) in isopropanol (20 mL). Heat to reflux. After 2 days, evaporate the reaction mixture in vacuo to give a residue. Combine the residue and ethyl acetate. Extract with water and brine. Dry the organic layer over $Na_2SO_4$, filter, and evaporate in vacuo to give the title compound.

Alternately, combine 4-(1-(5-(ethoxycarbonyl)fur-2-ylmethyl)-1H-benzimidazol-2-yl)[1,4]diazepane (10 mmol) and lithium aluminum hydride (10 mmol) in tetrahydrofuran. Heat to reflux. After 12 hour, cool and carefully quench the reaction mixture with water (0.4 mL), 15% aqueous sodium hydroxide solution (0.4 mL) and water (1.2 mL). Filter and extract the filtrate with ethyl acetate. Dry the organic layer over $Na_2SO_4$, filter, and evaporate in vacuo to give the title compound.

EXAMPLE 3

N-Methyl-N-(4-(4-(1-(5-hydroxymethylfur-2-ylmethyl)-1H-benzimidazol-2-yl)[1,4]diazepan-1-yl)-2-(4-fluorophenyl)butyl)-3,4,5-trimethoxybenzamide

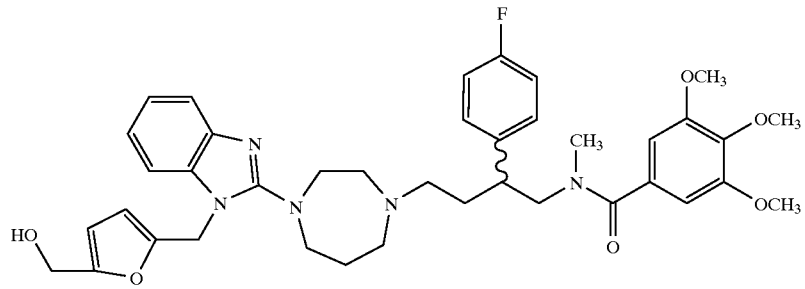

3.1 Synthesis of N-methyl-N-(4-(4-(1-(5-hydroxymethylfur-2-ylmethyl)-1H-benzimidazol-2-yl)[1,4]diazepan-1-yl)-2-(4-fluorophenyl)butyl)-3,4,5-trimethoxybenzamide Prepare by the method of Example 1.7 using N-methyl-N-(2-(4-fluorophenyl)-4-methanesulfonylbutyl)-3,4,5-trimethoxybenzamide and 4-(1-(5-hydroxymethylfur-2-ylmethyl)-1H-benzimidazol-2-yl)[1,4]diazepane to give the title compound.

EXAMPLE 4

N-Methyl-N-(4-(4-(1-(2-ethoxyethyl)-1H-benzimidazol-2-yl)[1,4]diazepan-1-yl)-2-(4-methoxyphenyl)butyl)benzamide

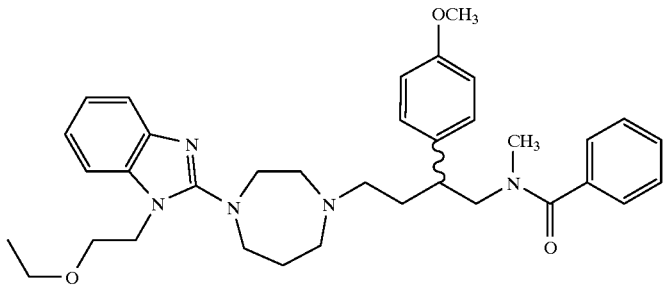

4.1 Synthesis of 2-(4-methoxyphenyl)-4-(t-butyldimethylsilyloxy)butyronitrile

Prepare by the method of Example 1.1.1 using 4-methoxyphenylacetonitrile and 1-(t-butyldimethylsilyloxy)-2-bromoethane to give the title compound.

4.2 Synthesis of 2-(4-methoxyphenyl)-4-(t-butyldimethylsilyloxy)butylamine

Prepare by the method of Example 1.2 using 2-(4-methoxyphenyl)-4-(t-butyldimethylsilyloxy)butyronitrile to give the title compound.

4.3 Synthesis of N-(2-(4-methoxyphenyl)-4-(t-butyldimethylsilyloxy)butyl)benzamide Prepare by the method of Example 1.3 using 2-(4-methoxyphenyl)-4-(t-butyldimethylsilyloxy)butylamine and benzoyl chloride to give the title compound.

4.4 Synthesis of N-methyl-N-(2-(4-methoxyphenyl)-4-(t-butyldimethylsilyloxy)butyl)benzamide Prepare by the method of Example 1.4 using N-(2-(4-methoxyphenyl)-4-(t-butyldimethylsilyloxy)butyl)benzamide to give the title compound.

4.5 Synthesis of N-methyl-N-(2-(4-methoxyphenyl)-4-hydroxybutyl)benzamide

Prepare by the method of Example 1.5 using N-methyl-N-(2-(4-methoxyphenyl)-4-(t-butyldimethylsilyloxy)butyl)benzamide to give the title compound.

4.6 Synthesis of N-methyl-N-(2-(4-methoxyphenyl)-4-methanesulfonylbutyl)benzamide Prepare by the method of Example 1.6 using N-methyl-N-(2-(4-methoxyphenyl)-4-hydroxybutyl)benzamide and methanesulfonyl chloride to give the title compound.

4.7 Synthesis of N-methyl-N-(4-(4-(1-(2-ethoxyethyl)-1H-benzimidazol-2-yl)[1,4]diazepan-1-yl)-2-(4-methoxyphenyl)butyl)benzamide Prepare by the method of Example 1.7 using N-methyl-N-(2-(4-methoxyphenyl)-4-methanesulfonylbutyl)benzamide and 4-(1-(2-ethoxyethyl)-1H-benzimidazol-2-yl)[1,4]diazepane hydriodic acid salt to give the title compound.

EXAMPLE 5

N-Methyl-N-(4-(4-(1-(2-ethoxyethyl)-1H-benzimidazol-2-yl)[1,4]diazepan-1-yl)-2-phenylbutyl)benzamide

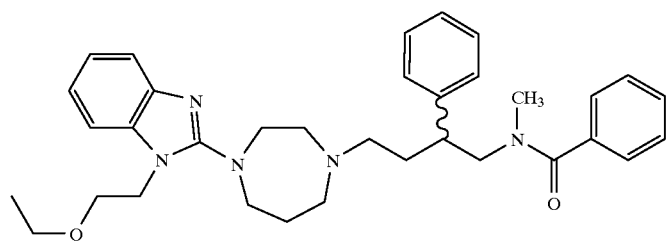

5.1 Synthesis of 2-phenyl-4-(t-butyldimethylsilyloxy)butyronitrile

Prepare by the method of Example 1.1.1 using phenylacetonitrile and 1-(t-butyldimethylsilyloxy)-2-bromoethane to give of the title compound.

5.2 Synthesis of 2-phenyl-4-(t-butyldimethylsilyloxy)butylamine

Prepare by the method of Example 1.2 using 2-phenyl-4-(t-butyldimethylsilyloxy)butyronitrile to give the title compound.

5.3 Synthesis of N-(2-phenyl-4-(t-butyldimethylsilyloxy)butyl)benzamide

Prepare by the method of Example 1.3 using 2-phenyl-4-(t-butyldimethylsilyloxy)butylamine and benzoyl chloride to give the title compound.

5.4 Synthesis of N-methyl-N-(2-phenyl-4-(t-butyldimethylsilyloxy)butyl)benzamide Prepare by the method of Example 1.4 using N-(2-phenyl-4-(t-butyldimethylsilyloxy)butyl)benzamide to give the title compound.

5.5 Synthesis of N-methyl-N-(2-phenyl-4-hydroxybutyl)benzamide

Prepare by the method of Example 1.5 using N-methyl-N-(2-phenyl-4-(t-butyldimethylsilyloxy)butyl)benzamide to give the title compound.

5.6 Synthesis of N-methyl-N-(2-phenyl-4-methanesulfonylbutyl)benzamide

Prepare by the method of Example 1.6 using N-methyl-N-(2-phenyl-4-hydroxybutyl)benzamide and methanesulfonyl chloride to give the title compound.

5.7 Synthesis of N-methyl-N-(4-(4-(1-(2-ethoxyethyl)-1H-benzimidazol-2-yl)[1,4]diazepan-1-yl)-2-phenylbutyl)benzamide Prepare by the method of Example 1.7 using N-methyl-N-(2-phenyl-4-methanesulfonylbutyl)benzamide and 4-(1-(2-ethoxyethyl)-1H-benzimidazol-2-yl)[1,4]diazepane hydriodic acid salt to give the title compound.

EXAMPLE 6

N-Methyl-N-(4-(4-(1-(2-ethoxyethyl)-1H-benzimidazol-2-yl)[1,4]diazepan-1-yl)-2-(3,4-dimethoxyphenyl)butyl)benzamide Prepare by the method of Example 1.4 using N-(2-(3,4-dimethoxyphenyl)-4-(t-butyldimethylsilyloxy)butyl)benzamide to give the title compound.

6.5 Synthesis of N-methyl-N-(2-(3,4-dimethoxyphenyl)-4-hydroxybutyl)benzamide Prepare by the method of Example 1.5 using N-methyl-N-(2-(3,4-dimethoxyphenyl)-4-(t-butyldimethylsilyloxy)butyl)benzamide to give the title compound.

6.6 Synthesis of N-methyl-N-(2-(3,4-dimethoxyohenyl)-4-methanesulfonylbutyl)benzamide Prepare by the method of Example 1.6 using N-methyl-N-(2-(3,4-dimethoxyphenyl)-4-hydroxybutyl)benzamide and methanesulfonyl chloride to give the title compound.

6.7 Synthesis of N-methyl-N-(4-(4-(1-(2-ethoxyethyl)-1H-benzimidazol-2-yl)[1,4]diazepan-1-yl)-2-(3,4-dimethoxyphenyl)butyl)benzamide Prepare by the method of Example 1.7 using N-methyl-N-(2-(3,4-dimethoxyphenyl)-4-methanesulfonylbutyl)benzamide and 4-(1-(2-ethoxyethyl)-1H-benzimidazol-2-yl)[1,4]diazepane hydriodic acid salt to give the title compound.

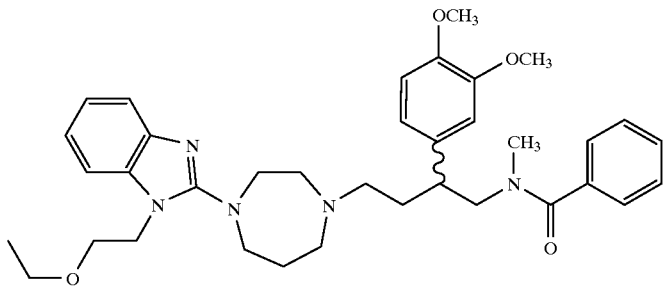

6.1 Synthesis of 2-(3,4-dimethoxyphenyl)-4-(t-butyldimethylsilyloxy)butyronitrile Prepare by the method of Example 1.1.1 using 3,4-dimethoxyphenylacetonitrile and 1-(t-butyldimethylsilyloxy)-2-bromoethane to give of the title compound.

6.2 Synthesis of 2-(3,4-dimethoxyphenyl)-4-(t-butyldimethylsilyloxy)butylamine Prepare by the method of Example 1.2 using 2-(3,4-dimethoxyphenyl)-4-(t-butyldimethylsilyloxy)butyronitrile to give the title compound.

6.3 Synthesis of N-(2-(3,4-dimethoxyphenyl)-4-(t-butyldimethylsilyloxy)butyl)benzamide Prepare by the method of Example 1.3 using 2-(3,4-dimethoxyphenyl)-4-(t-butyldimethylsilyloxy)butylamine and benzoyl chloride to give the title compound.

6.4 Synthesis of N-methyl-N-(2-(3,4-dimethoxyphenyl)-4-(t-butyldimethylsilyloxy)butyl)benzamide

EXAMPLE 7

N-Methyl-N-(4-(4-(1-(2-ethoxyethyl)-1H-benzimidazol-2-yl)[1,4 diazepan-1-yl)-2-(benzor[1,3]dioxol-5-yl)butyl)benzamide

7.1 Synthesis of 2-(benzo[1,3]dioxol-5-yl)-4-(t-butyldimethylsilyloxy)butyronitrile Prepare by the method of Example 1.1.1 using benzo[1,3]dioxol-5-ylacetonitrile and 1-(t-butyldimethylsilyloxy)-2-bromoethane to give of the title compound.

7.2 Synthesis of 2-(benzo[1,3]dioxol-5-yl)-4-(t-butyldimethylsilyloxy)butylamine Prepare by the method of Example 1.2 using 2-(benzo[1,3]dioxol-5-yl)-4-(t-butyldimethylsilyloxy)butyronitrile to give the title compound.

7.3 Synthesis of N-(2-(benzo[1,3]dioxol-5-yl)-4-(t-butyldimethylsilyloxy)butyl)benzamide Prepare by the method of Example 1.3 using 2-(benzo[1,3]dioxol-5-yl)-4-(t-butyldimethylsilyloxy)butylamine and benzoyl chloride to give the title compound.

7.4 Synthesis of N-methyl-N-(2-(benzo[1,3]dioxol-5-yl)-4-(t-butyldimethylsilyloxy)butyl)benzamide Prepare by the method of Example 1.4 using N-(2-(benzo[1,3]dioxol-5-yl)-4-(t-butyldimethylsilyloxy)butyl)benzamide to give the title compound.

7.5 Synthesis of N-methyl-N-(2-(benzo[1,3]dioxol-5-yl)-4-hydroxybutyl)benzamide

Prepare by the method of Example 1.5 using N-methyl-N-(2-(benzo[1,3]dioxol-5-yl)-4-(t-butyldimethylsilyloxy)butyl)benzamide to give the title compound.

7.6 Synthesis of N-methyl-N-(2-(benzo[1,3]dioxol-5-yl)-4-methanesulfonylbutyl)benzamide Prepare by the method of Example 1.6 using N-methyl-N-(2-(benzo[1,3]dioxol-5-yl)-4-hydroxybutyl)benzamide and methanesulfonyl chloride to give the title compound.

7.7 Synthesis of N-methyl-N-(4-(4-(1-(2-ethoxyethyl)-1H-benzimidazol-2-yl)[1,4]diazepan-1-yl)-2-(benzo[1,3]dioxol-5-yl)butyl)benzamide Prepare by the method of Example 1.7 using N-methyl-N-(2-(benzo[1,3]dioxol-5-yl)-4-methanesulfonylbutyl)benzamide and 4-(1-(2-ethoxyethyl)-1H-benzimidazol-2-yl)[1,4]diazepane hydriodic acid salt to give the title compound.

PREPARATION 7

Synthesis of 4-(1H-benzimidazol-2-yl)[1,4]diazepane hydriodic acid salt

Combine [1,4]diazepane (33.9 g, 340 mmol) and water (250 mL). Add methyl orange and adjust the pH using 3 M aqueous hydrochloric acid solution until the indicator turns red. Add dropwise, ethyl chloroformate (38 mL, 400 mmol) over about 2.5 hours while maintaining the pH using first aqueous sodium acetate and then aqueous sodium hydroxide solution. After the addition is complete adjust the pH to 8 using aqueous sodium hydroxide solution and extract three times with diethyl ether. Discard the organic extracts and saturate the aqueous layer with potassium carbonate. Extract three times with diethyl ether. Combine the organic layers from the second extraction, dry the over Na$_2$SO$_4$, filter, and evaporate in vacuo to give a 1-ethoxycarbonyl[1,4]diazepane. Combine 1-ethoxycarbonyl[1,4]diazepane (36.6 g, 212 mmol) and 2-chlorobenzimidazole (18.0 g, 106 mmol). Heat to 130° C. After 4 hours, cool to ambient temperature and add hot methanol to dissolve the reaction mixture. Partition the methanol solution between dichloromethane (700 mL) and a solution of sodium hydroxide (20 g) in water (500 mL). Separate the layers and extract the aqueous layer three times with dichloromethane. Combine the organic layers, extract with brine, dry over Na$_2$SO$_4$, filter, and evaporate in vacuo to give a solid. Triturate the solid with ethyl acetate (100 mL) and cool to 0° C. Collect solid by filtration and dry in vacuo to give 1-ethoxycarbonyl-4-(1H-benzimidazol-2-yl)[1,4]diazepane.

Combine 1-ethoxycarbonyl-4-(1H-benzimidazol-2-yl)[1,4]diazepane (16.7 g, 58 mmol) and aqueous 48% hydrobromic acid solution (80 mL). Heat to reflux. After 3 hours, cool to ambient temperature, add to ethanol (700 mL), and cool to 0° C. to give a solid. Combine the solid with aqueous 48% hydriodic acid (80 mL) and water (150 mL). Heat on a steam bath. After about 1 hour, cool to ambient temperature, dilute with ethanol (500 mL), and add to diethyl ether (8 L) to give a solid. Collect solid by filtration and dry in vacuo to give the title compound: mp; >290° C.

EXAMPLE 8

N-Methyl-N-(4-(4-(1H-benzimidazol-2-yl)[1,4]diazepan-1-yl)-2-(4-fluorophenyl)butyl)-3,4,5-trimethoxybenzamide

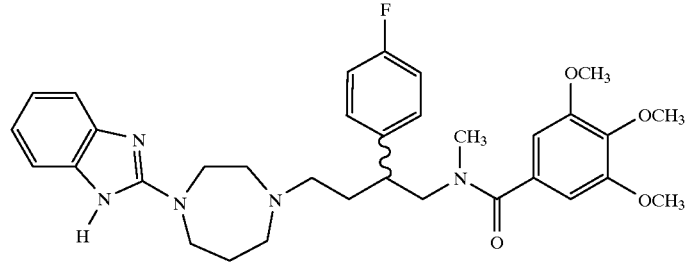

8.1 Synthesis of N-methyl-N-(4-(4-(1H-benzimidazol-2-yl)[1,4]diazepan-1-yl)-2-(4-fluorophenyl)butyl)-3,4,5-trimethoxybenzamide Prepare by the method of Example 1.7 using N-methyl-N-(2-(4-fluorophenyl)-4-methanesulfonylbutyl)-3,4,5trimethoxybenzamide and 4-(1H-benzimidazol-2-yl)[1,4]diazepane hydriodic acid salt to give the title compound.

EXAMPLE 9

N-Methyl-N-(4-(4-(1H-benzimidazol-2-yl)[1,4]diazepan-1-yl)-2-(3,4-dichlorophenyl)butyl)-3,4,5-trimethoxybenzamide

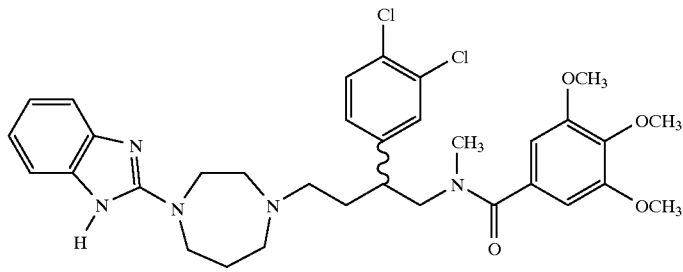

9.1 Synthesis of N-methyl-N-(4-(4-(1H-benzimidazol-2-yl)[1,4]diazepan-1-yl)-2-(3,4-dichlorophenyl)butyl)-3,4,5-trimethoxybenzamide Prepare by the method of Example 1.7 using N-methyl-N-(2-(3,4-dichlorophenyl)-4-methanesulfonylbutyl)-3,4,5-trimethoxybenzamide and 4-(1H-benzimidazol-2-yl)[1,4]diazepane hydriodic acid salt to give the title compound.

EXAMPLE 10

N-Methyl-N-(4-(4-(1H-benzimidazol-2-yl)[1,4]diazepan-1-yl)-2-(4-methoxyphenyl)butyl)-3,4,5-trimethoxybenzamide

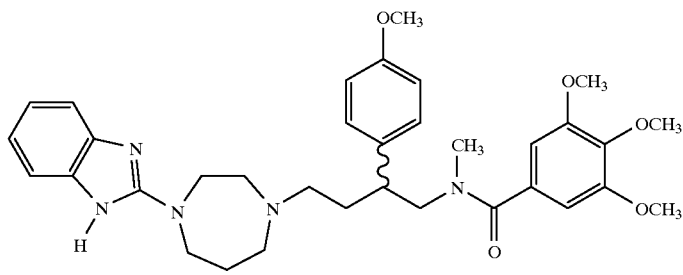

10.1 Synthesis of N-methyl-N-(4-(4-(1H-benzimidazol-2-yl)[1,4]diazepan-1-yl)-2-(4-methoxyphenyl)butyl)-3,4,5trimethoxybenzamide Prepare by the method of Example 1.7 using N-methyl-N-(2-(4-methoxyphenyl)-4-methanesulfonylbutyl)-3,4,5-trimethoxybenzamide and 4-(1H-benzimidazol-2-yl)[1,4]diazepane hydriodic acid salt to give the title compound.

EXAMPLE 11

N-Methyl-N-(4-(4-(1-(2-ethoxyethyl)-1H-benzimidazol-2-yl)[1,4]diazepan-1-yl)-2-(naphth-2-yl)butyl)benzamide

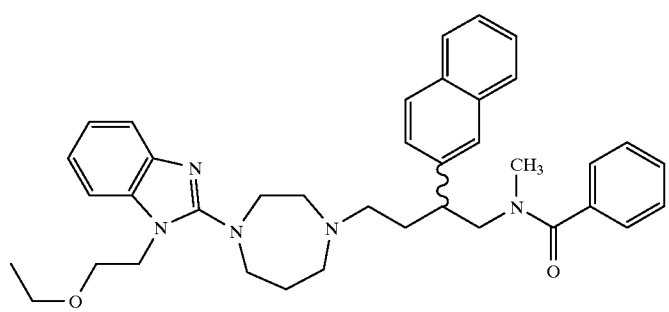

11.1 Synthesis of 2-(naphth-2-yl)-4-(t-butyldimethylsilyloxy)butyronitrile

Prepare by the method of Example 1.1.1 using naphth-2-ylacetonitrile and 1-(t-butyldimethylsilyloxy)-2-bromoethane to give of the title compound.

11.2 Synthesis of 2-(naphth-2-yl)-4-(t-butyldimethylsilyloxy)butylamine

Prepare by the method of Example 1.2 using 2-(naphth-2-yl)-4-(t-butyldimethylsilyloxy)butyronitrile to give the title compound.

11.3 Synthesis of N-(2-(naphth-2-yl)-4-(t-butyldimethylsilyloxy)butyl)benzamide

Prepare by the method of Example 1.3 using 2-(naphth-2-yl)-4-(t-butyldimethylsilyloxy)butylamine and benzoyl chloride to give the title compound.

11.4 Synthesis of N-methyl-N-(2-(naphth-2-yl)-4-(t-butyldimethylsilyloxy)butyl)benzamide Prepare by the method of Example 1.4 using N-(2-(naphth-2-yl)-4-(t-butyldimethylsilyloxy)butyl)benzamide to give the title compound.

11.5 Synthesis of N-methyl-N-(2-(naphth-2-yl)-4-hydroxybutyl)benzamide

Prepare by the method of Example 1.5 using N-methyl-N-(2-(naphth-2-yl)-4-(t-butyldimethylsilyloxy)butyl)benzamide to give the title compound.

11.6 Synthesis of N-methyl-N-(2-(naphth-2-yl)-4-methanesulfonylbutyl)benzamide

Prepare by the method of Example 1.6 using N-methyl-N-(2-(naphth-2-yl)-4-hydroxybutyl)benzamide and methanesulfonyl chloride to give the title compound.

11.7 Synthesis of N-methyl-N-(4-(4-(1-(2-ethoxyethyl)-1H-benzimidazol-2-yl)[1,4]diazepan-1-yl)-2-(naphth-2-yl)butyl)benzamide Prepare by the method of Example 1.7 using N-methyl-N-(2-(naphth-2-yl)-4-methanesulfonylbutyl)benzamide and 4-(1-(2-ethoxyethyl)-1H-benzimidazol-2-yl)[1,4]diazepane to give the title compound.

EXAMPLE 12

N-Methyl-N-(4-(4-(1-(2-ethoxyethyl)-1H-benzimidazol-2-yl)[1,4diazepan-1-yl)-2-(3,4-dichlorophenyl)butyl)-3,5-bis(trifluoromethyl) benzamide

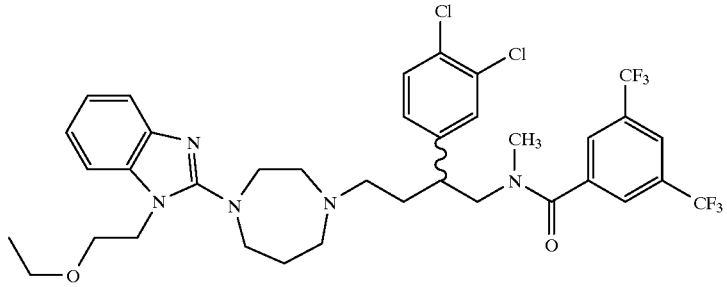

12.1 Synthesis of N-(2-(3,4-dichlorophenyl)-4-(t-butyldimethylsilyloxy)butyl)-3,5-bis(trifluoromethyl)benzamide Prepare by the method of Example 1.3 using 2-(3,4-dichlorophenyl)-4-(t-butyldimethylsilyloxy)butylamine and 3,5-bis(trifluoromethyl)benzoyl chloride to give the title compound.

12.2 Synthesis of N-methyl-N-(2-(3,4-dichlorophenyl)-4-(t-butyldimethylsilYloxy)butyl)-3,5-bis(trifluoromethyl)-benzamide Prepare by the method of Example 1.4 using N-(2-(3,4-dichlorophenyl)-4-(t-butyldimethylsilyloxy)butyl)-3,5-bis(trifluoromethyl)benzamide to give the title compound.

12.3 Synthesis of N-methyl-N-(2-(3,4-dichlorophenyl)-4-hydroxybutyl)-3,5-bis(trifluoromethyl)benzamide Prepare by the method of Example 1.5 using N-methyl-N-(2-(3,4-dichlorophenyl)-4-(t-butyldimethylsilyloxy)butyl)-3,5-bis(trifluoromethyl)benzamide to give the title compound.

12.4 Synthesis of N-methyl-N-(2-(3,4-dichlorophenyl)-4-methanesulfonylbutyl)-3,5-bis(trifluoromethyl)benzamide Prepare by the method of Example 1.6 using N-methyl-N-(2-(3,4-dichlorophenyl)-4-hydroxybutyl)-3,5-bis(trifluoromethyl)benzamide and methanesulfonyl chloride to give the title compound.

12.5 Synthesis of N-methyl-N-(4-(4-(1-(2-ethoxyethyl)-1H-benzimidazol-2-yl)[1,4]diazepan-1-yl)-2-(3,4-dichlorophenyl)butyl)3,5-bis(trifluoromethyl)benzamide Prepare by the method of Example 1.7 using N-methyl-N-(2-(3,4-dichlorophenyl)-4-methanesulfonylbutyl)-3,5-bis(trifluoromethyl)benzamide and 4-(1-(2-ethoxyethyl)-1H-benzimidazol-2-yl)[1,4]diazepane to give the title compound.

EXAMPLE 13

N-Methyl-N-(4-(4-(1-(2-ethoxyethyl)-1H-benzimidazol-2-yl)[1,4]diazepan-1-yl)-2-(3-trifluoromethylphenyl)butyl)-3,4,5-trimethoxybenzamide

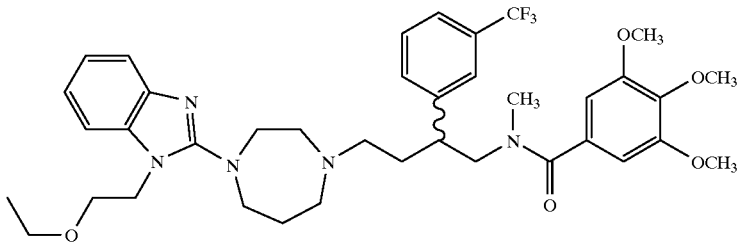

13.1 Synthesis of 2-(3-trifluoromethylphenyl)-4-(t-butyldimethylsilyloxy)butyronitrile Prepare by the method of Example 1.1.1 using 3-trifluoromethylphenylacetonitrile and 1-(t-butyldimethylsilyloxy)-2-bromoethane to give the title compound.

13.2 Synthesis of 2-(3-trifluoromethylphenyl)-4-(t-butyldimethylsilyloxy)butylamine Prepare by the method of Example 1.2 using 2-(3-trifluoromethylphenyl)-4-(t-butyldimethylsilyloxy)butyronitrile to give the title compound.

13.3 Synthesis of N-(2-(3-trifluoromethylphenyl)-4-(t-butyldimethylsilyloxy)butyl)-3,4,5-trimethoxybenzamide Prepare by the method of Example 1.3 using 2-(3-trifluoromethylphenyl)-4-(t-butyldimethylsilyloxy) butylamine and 3,4,5-trimethoxybenzoyl chloride to give the title compound.

13.4 Synthesis of N-methyl-N-(2-(3-trifluoromethylphenyl)-4-(t-butyldimethylsilyloxy)butyl)-3,4,5-trimethoxybenzamide Prepare by the method of Example 1.4 using N-(2-(3-trifluoromethylphenyl)-4-(t-butyldimethylsilyloxy)butyl)-3,4,5-trimethoxybenzamide to give the title compound.

13.5 Synthesis of N-methyl-N-(2-(3-trifluoromethylphenyl)-4-hydroxybutyl)-3,4,5-trimethoxybenzamide Prepare by the method of Example 1.5 using N-methyl-N-(2-(3-trifluoromethylphenyl)-4-(t-butyldimethylsilyloxy)butyl)-3,4,5-trimethoxybenzamide to give the title compound.

13.6 Synthesis of N-methyl-N-(2-(3-trifluoromethylphenyl)-4-methanesulfonylbutyl)-3,4,5-trimethoxybenzamide Prepare by the method of Example 1.6 using N-methyl-N-(2-(3-trifluoromethylphenyl)-4-hydroxybutyl)-3,4,5-trimethoxybenzamide to give the title compound.

13.7 Synthesis of N-methyl-N-(4-(4-(1-(2-ethoxyethyl)-1H-benzimidazol-2-yl)[1,4]diazepan-1-yl)-2-(3-trifluoromethylphenyl)butyl)-3,4,5-trimethoxybenzamide Prepare by the method of Example 1.7 using N-methyl-N-(2-(3-trifluoromethylphenyl)-4-methanesulfonylbutyl)-3,4,5-trimethoxybenzamide and 4-(1-(2-ethoxyethyl)-1H-benzimidazol-2-yl)[1,4]diazepane to give the title compound.

EXAMPLE 14

N-Methyl-N-(4-(4-(1-(2-ethoxyethyl)-1H-benzimidazol-2-yl) [4]diazepan-1-yl)-2-(thien-2-yl)butyl)-3,4,5-trimethoxybenzamide

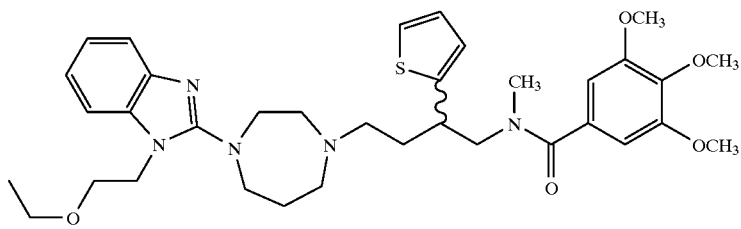

14.1 Synthesis of 2-(thien-2-yl)-4-(t-butyldimethylsilyloxy)butyronitrile

Prepare by the method of Example 1.1.1 using thien-2-ylacetonitrile and 1-(t-butyldimethylsilyloxy)-2-bromoethane to give of the title compound.

14.2 Synthesis of 2-(thien-2-yl)-4-(t-butyldimethylsilyloxy)-butylamine

Combine 2-(thien-2-yl)-4-(t-butyldimethylsilyloxy)-butyronitrile (3.24 mmol) and cobalt(II)chloride hexahydrate (1.54 g, 6.48 mmol) in methanol (50 mL). While maintaining the temperature at or below 20° C. with an ice-bath, add portionwise sodium borohydride (2.17 g, 57 mmol). After the addition is complete, allow the reaction mixture to stand at ambient temperature for 18 hours. Evaporate the reaction mixture in vacuo to obtain a residue. Partition the residue between dichloromethane and a saturated aqueous solution of ammonium chloride. Adjust the pH of the aqueous layer to about 8 using a 1 M aqueous solution of hydrochloric acid. Separate the layers and extract the aqueous layer several times with dichloromethane, combine the organic layers, dry over $Na_2SO_4$, filter, and concentrate in vacuo to give the title compound.

14.3 Synthesis of N-(2-(thien-2-yl)-4-(t-butyldimethylsilyloxy)butyl)-3,4,5-trimethoxybenzamide Prepare by the method of Example 1.3 using 2-(thien-2-yl)-4-(t-butyldimethylsilyloxy)butylamine and 3,4,5-trimethoxybenzoyl chloride to give the title compound.

14.4 Synthesis of N-methyl-N-(2-(thien-2-yl)-4-(t-butyldimethylsilyloxy)butyl)-3,4,5-trimethoxybenzamide Prepare by the method of Example 1.4 using N-(2-(thien-2-yl)-4-(t-butyldimethylsilyloxy)butyl)-3,4,5-trimethoxybenzamide to give the title compound.

14.5 Synthesis of N-methyl-N-(2-(thien-2-yl)-4-hydroxybutyl)-3,4,5-trimethoxybenzamide Prepare by the method of Example 1.5 using N-methyl-N-(2-(thien-2-yl)-4-(t-butyldimethylsilyloxy)butyl)-3,4,5-trimethoxybenzamide to give the title compound.

14.6 Synthesis of N-methyl-N-(2-(thien-2-yl)-4-methanesulfonylbutyl)-3,4,5-trimethoxybenzamide Prepare by the method of Example 1.6 using N-methyl-N-(2-(thien-2-yl)-4-hydroxybutyl)-3,4,5-trimethoxybenzamide and methanesulfonyl chloride to give the title compound.

14.7 Synthesis of N-methyl-N-(4-(4-(1-(2-ethoxyethyl)-1H-benzimidazol-2-yl) [1,4]diazepan-1-yl)-2-(thien-2-yl) butyl)-3,4,5-trimethoxybenzamide Prepare by the method of Example 1.7 using N-methyl-N-(2-(thien-2-yl)-4-methanesulfonylbutyl)-3,4,5-trimethoxybenzamide and 4-(1-(2-ethoxyethyl)-1H-benzimidazol-2-yl)[1,4]diazepane to give the title compound.

EXAMPLE 15

N-Methyl-N-(4-(4-(1-(2-ethoxyethyl)-1H-benzimidazol-2-yl) [1,4]diazepan-1-yl)-2-(pyrid-3-yl)butyl)-3,4,5-trimethoxybenzamide 15.2 Synthesis of 2-(pyrid-3-yl)-4-(t-butyldimethylsilyloxy)-butylamine Prepare by the method of Example 14.2 using 2-(pyrid-3-yl)-4-(t-butyldimethylsilyloxy)butyronitrile to give the title compound.

15.3 Synthesis of N-(2-(pyrid-3-yl)-4-(t-butyldimethylsilyloxy)butyl)-3,4,5-trimethoxybenzamide Prepare by the method of Example 1.3 using 2-(pyrid-3-yl)-4-(t-butyldimethylsilyloxy)butylamine and 3,4,5-trimethoxybenzoyl chloride to give the title compound.

15.4 Synthesis of N-methyl-N-(2-(pyrid-3-yl)-4-(t-butyldimethylsilyloxy)butyl)-3,4,5-trimethoxybenzamide Prepare by the method of Example 1.4 using N-(2-(pyrid-3-yl)-4-(t-butyldimethylsilyloxy)butyl)-3,4,5-trimethoxybenzamide to give the title compound.

15.5 Synthesis of N-methyl-N-(2-(pyrid-3-yl)-4-hydroxybutyl)-3,4,5-trimethoxybenzamide Prepare by the method of Example 1.5 using N-methyl-N-(2-(pyrid-3-yl)-4-(t-butyldimethylsilyloxy)butyl)-3,4,5-trimethoxybenzamide to give the title compound.

15.6 Synthesis of N-methyl-N-(2-(pyrid-3-yl)-4-methanesulfonylbutyl)-3,4,5-trimethoxybenzamide Prepare by the method of Example 1.6 using N-methyl-N-(2-(pyrid-3-yl)-4-hydroxybutyl)-3,4,5-trimethoxybenzamide and methanesulfonyl chloride. Isolate by extraction using a saturated solution of sodium bicarbonate to give the title compound.

15.7 Synthesis of N-methyl-N-(4-(4-(1-(2-ethoxyethyl)-1H-benzimidazol-2-yl) [1,4]diazepan-1-yl)-2-(pyrid-3-yl)butyl)-3,4,5-trimethoxybenzamide Prepare by the method of Example 1.7 using N-methyl-N-(2-(pyrid-3-yl)-4-methanesulfonylbutyl)-3,4,5-trimethoxybenzamide and 4-(1-(2-ethoxyethyl)-1H-benzimidazol-2-yl) [1,4]diazepane to give the title compound.

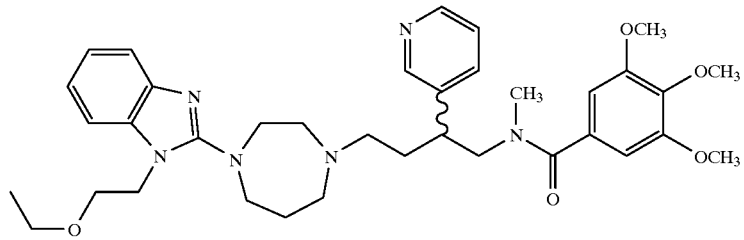

15.1 Synthesis of 2-(pyrid-3-yl)-4-(t-butyldimethylsilyloxy)-butyronitrile

Prepare by the method of Example 1.1.2 using pyrid-3-ylacetonitrile and 1-(t-butyldimethylsilyloxy)-2-bromoethane to give of the title compound.

EXAMPLE 16

N-Methyl-N-(4-(4-(1-(2-ethoxyethyl)-1H-benzimidazol-2-yl)[1,4]diazepan-1-yl)-2-(3,4-dichlorophenyl)butyl)-3,4,5-trimethoxybenzamide

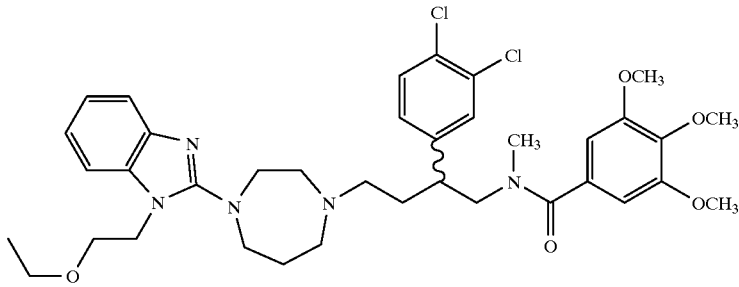

16.1 Synthesis of N-(2-(3,4-dichlorophenyl)-4-(t-butyldimethylsilyloxy)butyl)-3,4,5-trimethoxybenzamide Prepare by the method of Example 1.3 using 2-(3,4-dichlorophenyl)-4-(t-butyldimethylsilyloxy)butylamine and 3,4,5-trimethoxybenzoyl chloride to give the title compound.

16.2 Synthesis of N-methyl-N-(2-(3,4-dichlorophenyl)-4-(t-butyldimethylsilyloxy)butyl)-3,4,5-trimethoxybenzamide Prepare by the method of Example 1.4 using N-(2-(3,4-dichlorophenyl)-4-(t-butyldimethylsilyloxy)butyl)-3,4,5-trimethoxybenzamide to give the title compound.

16.3 Synthesis of N-methyl-N-(2-(3,4-dichlorophenyl)-4-hydroxybutyl)-3,4,5-trimethoxybenzamide Prepare by the method of Example 1.5 using N-methyl-N-(2-(3,4-dichlorophenyl)-4-(t-butyldimethylsilyloxy)butyl)-3,4,5-trimethoxybenzamide to give the title compound.

16.4 Synthesis of N-methyl-N-(2-(3,4-dichlorophenyl)-4-methanesulfonylbutyl)-3,4,5-trimethoxybenzamide Prepare by the method of Example 1.6 using N-methyl-N-(2-(3,4-dichlorophenyl)-4-hydroxybutyl)-3,4,5-trimethoxybenzamide and methanesulfonyl chloride to give the title compound.

16.5 Synthesis of N-methyl-N-(4-(4-(1-(2-ethoxyethyl)-1H-benzimidazol-2-yl)[1,4]diazepan-1-yl)-2-(3,4-dichlorophenyl)butyl)-3,4,5-trimethoxybenzamide Prepare by the method of Example 1.7 using N-methyl-N-(2-(3,4-dichlorophenyl)-4-methanesulfonylbutyl)-3,4,5-trimethoxybenzamide and 4-(1-(2-ethoxyethyl)-1H-benzimidazol-2-yl)[1,4]diazepane to give the title compound.

EXAMPLE 17

N-Methyl-N-(4-(4-(1H-benzimidazol-2-yl)[1,4]diazepan-1-yl)-2-phenylbutyl)-3,4,5-trimethoxybenzamide

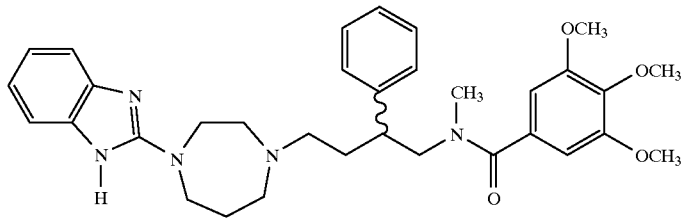

17.1 Synthesis of N-(2-phenyl-4-(t-butyldimethylsilyloxy)butyl)-3,4,5-trimethoxybenzamide Prepare by the method of Example 1.3 using 2-phenyl-4-(t-butyldimethylsilyloxy)butylamine and 3,4,5-trimethoxybenzoyl chloride to give the title compound.

17.2 Synthesis of N-methyl-N-(2-phenyl-4-(t-butyldimethylsilyloxy)butyl)-3,4,5-trimethoxybenzamide Prepare by the method of Example 1.4 using N-(2-phenyl-4-(t-butyldimethylsilyloxy)butyl)-3,4,5-trimethoxybenzamide to give the title compound.

17.3 Synthesis of N-methyl-N-(2-phenyl-4-hydroxybutyl)-3,4,5-trimethoxybenzamide Prepare by the method of Example 1.5 using N-methyl-N-(2-phenyl-4-(t-butyldimethylsilyloxy)butyl)-3,4,5-trimethoxybenzamide to give the title compound.

17.4 Synthesis of N-methyl-N-(2-phenyl-4-methanesulfonylbutyl)-3,4,5-trimethoxybenzamide Prepare by the method of Example 1.6 using N-methyl-N-(2-phenyl-4-hydroxybutyl)-3,4,5-trimethoxybenzamide and methanesulfonyl chloride to give the title compound.

17.5 Synthesis of N-methyl-N-(4-(1H-benzimidazol-2-yl)[1,4]diazepan-1-yl)-2-phenylbutyl)-3,4,5-trimethoxybenzamide Prepare by the method of Example 1.7 using N-methyl-N-(2-phenyl-4-methanesulfonylbutyl)-3,4,5-trimethoxybenzamide and 4-(1H-benzimidazol-2-yl)[1,4]diazepane to give the title compound.

PREPARATION 8

Synthesis of 2-methylsulfonylethyl mesylate

Combine 2-methylsulfonylethanol (7.7 g, 62 mmol) and dichloromethane (50 mL). Cool in an ice bath. Add methanesulfonyl chloride (7.81 g, 68.2 mmol). Add diisopropylethylamine (8.0 g, 62 mmol). After the addition of diisopropylethylamine, warm to ambient temperature. After 12 hours, add water and separate the layers. Extract the organic layer with a saturated aqueous sodium bicarbonate solution. Dry the organic layer over $Na_2SO_4$, filter and evaporate in vacuo to give the title compound: mp; 55–57° C.

EXAMPLE 18

N-Methyl-N-(4-(4-(1-(2-methylsulfonylethyl)-1H-benzimidazol-2-yl)[1,4]diazepan-1-yl)-2-phenylbutyl)-3,4,5-trimethoxybenzamide

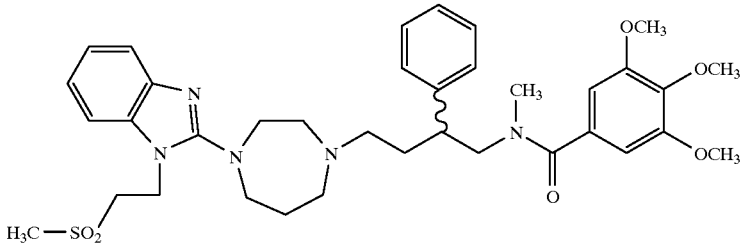

18.1 Synthesis of N-Methyl-N-(4-(4-(1-(2-methylsulfonylethyl)-1H-benzimidazol-2-yl)[1,4]diazepan-1-yl)-2-phenylbutyl)-3,4,5-trimethoxybenzamide Combine N-Methyl-N-(4-(4-(1H-benzimidazol-2-yl)[1,4]diazepan-1-yl)-2-phenylbutyl)-3,4,5-trimethoxybenzamide (0.09 mmol) and tetrahydrofuran (5 mL). Cool to –78° C. using a dry-ice/acetone bath. Add dropwise a solution of sec-butyllithium (0.15 mL, 1.3 M, 0.18 mmol). When the addition of sec-butyllithium is complete, add a solution 2-methylsulfonylethyl mesylate (0.02 g, 0.10 mmol) in tetrahydrofuran (2 mL). Heat the reaction mixture to reflux. After 12 hours, cool, add sec-butyllithium (0.10 mL) and 2-methylsulfonylethyl mesylate (0.02 g, 0.10 mmol) and again heat the reaction mixture to reflux. After 12 hours, cool, add water, separate the layers and extract the aqueous layer twice with ethyl acetate. Combine the organic layers, dry over $Na_2SO_4$, filter, and evaporate in vacuo to give the title compound.

EXAMPLE 18A

N-Methyl-N-(4-(4-(1-(2-ethylsulfonylethyl)-1H-benzimidazol-2-yl)[1,4]diazepan-1-yl)-2-phenylbutyl)-3,4,5-trimethoxybenzamide

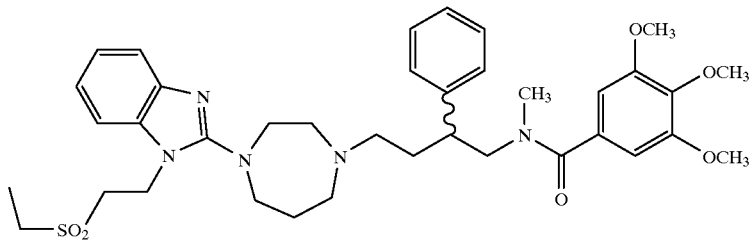

18A.1 Synthesis of N-Methyl-N-(4-(4-(1-(2-ethylsulfonylethyl)-1H-benzimidazol-2-yl)[1,4]diazepan-1-yl)-2-phenylbutyl)-3,4,5-trimethoxybenzamide Combine N-Methyl-N-(4-(4-(1H-benzimidazol-2-yl)[1,4]diazepan-1-yl)-2-phenylbutyl)-3,4,5-trimethoxybenzamide (1.0 mmol) and tetrahydrofuran (10 mL). Cool to −78° C. using a dry-ice/acetone bath. Add dropwise a solution of sec-butyllithium (1.26 mL, 1.3 M, 1.64 mmol). When the addition of sec-butyllithium is complete, add a solution ethyl vinyl sulfone (0.37 g, 3.08 mmol) in tetrahydrofuran (2 mL). Heat the reaction mixture to reflux and seal with a rubber septum. After 18 hours, cool, add ethyl vinyl sulfone (0.37 g, 3.08 mmol) and again heat the reaction mixture to reflux. After 6 hours, cool, add water, separate the layers and extract the aqueous layer twice with ethyl acetate. Combine the organic layers, dry over $Na_2SO_4$, filter, and evaporate in vacuo to give the title compound.

EXAMPLE 19

N-Methyl-N-(4-(4-(1-(2-phenylsulfonylethyl)-1H-benzimidazol-2-yl)[1,4]diazepan-1-yl)-2-phenylbutyl)-3,4,5-trimethoxybenzamide

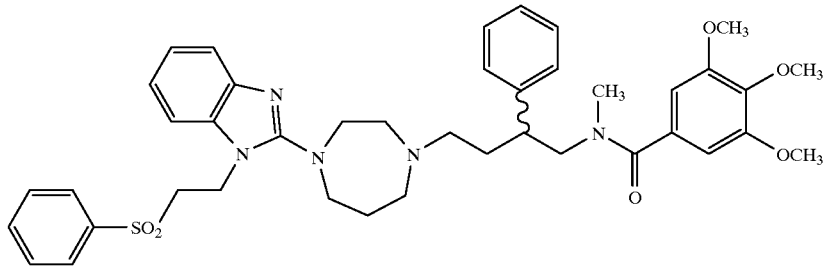

19.1 Synthesis of N-methyl-N-(4-(4-(1-(2-phenylsulfonylethyl)-1H-benzimidazol-2-yl)[[1,4]diazepan-1-yl)-2-phenylbutyl)-3,4,5-trimethoxybenzamide Combine N-Methyl-N-(4-(4-(1H-benzimidazol-2-yl)[1,4]diazepan-1-yl)-2-phenylbutyl)-3,4,5-trimethoxybenzamide (1.07 mmol) and tetrahydrofuran (10 mL). Cool to −78° C. using a dry-ice/acetone bath. Add dropwise a solution of sec-butyllithium (1.23 mL, 1.3 M, 1.61 mmol). When the addition of sec-butyllithium is complete, add a solution phenyl vinyl sulfone (0.36 g, 2.14 mmol). Heat the reaction mixture to reflux. After 12 hours, cool, add phenyl vinyl sulfone (0.36 g, 2.14 mmol) and again heat the reaction mixture to reflux. After 3 hours, cool, add phenyl vinyl sulfone (0.36 g, 2.14 mmol) and again heat the reaction mixture to reflux. After 2.5 hours, cool, add water, separate the layers and extract the aqueous layer twice with ethyl acetate. Combine the organic layers, dry over $Na_2SO_4$, filter, and evaporate in vacuo to give the title compound.

EXAMPLE 20

N-Methyl-N-(4-(4-(1-(2-cyanoethyl)-1H-benzimidazol-2-yl)[1,4]diazepan-1-yl)-2-phenylbutyl)-3,4,5-trimethoxybenzamide

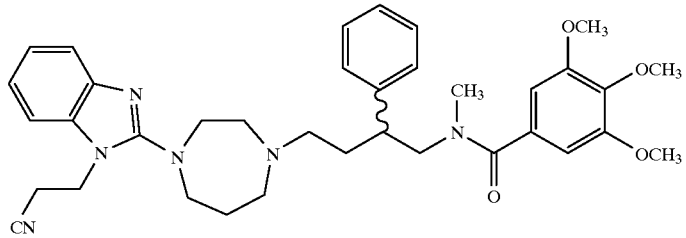

20.1 Synthesis of N-methyl-N-(4-(4-(1-(2-cyanoethyl)-1H-benzimidazol-2-yl)[1,4]diazepan-1-yl)-2-phenylbutyl)-3,4,5-trimethoxybenzamide Combine N-Methyl-N-(4-(4-(1H-benzimidazol-2-yl)[1,4]diazepan-1-yl)-2-phenylbutyl)-3,4,5-trimethoxybenzamide (0.09 mmol) and tetrahydrofuran (4 mL). Cool to −78° C. using a dry-ice/acetone bath. Add dropwise a solution of sec-butyllithium (0.08 mL, 1.3 M, 0.10 mmol). When the addition of sec-butyllithium is complete, warm the reaction mixture to ambient temperature. Add acrylonitrile (0.005 g, 0.10 mmol) and heat the reaction mixture to reflux. After 12 hours, cool, add acrylonitrile (0.01 g, 0.20 mmol), and heat the reaction mixture to reflux. After 12 hours, cool, add water, separate the layers and extract the aqueous layer twice with ethyl acetate. Combine the organic layers, dry over Na$_2$SO$_4$, filter, and evaporate in vacuo to give the title compound.

EXAMPLE 21

N-Methyl-N-(4-(4-(1-(pyrid-2-ylmethyl)-1H-benzimidazol-2-yl)[1,4]diazepan-1-yl)-2-phenylbutyl)-3,4,5-trimethoxybenzamide

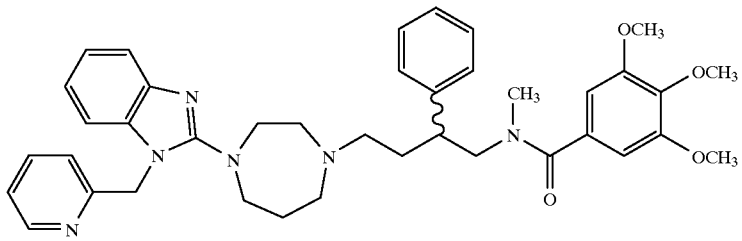

21.1 Synthesis of N-methyl-N-(4-(4-(1-(pyrid-2-ylmethYl)-1H-benzimidazol-2-yl)[1,4]diazepan-1-yl)-2-phenylbutyl)-3,4,5-trimethoxybenzamide Combine N-Methyl-N-(4-(4-(1H-benzimidazol-2-yl)[1,4]diazepan-1-yl)-2-phenylbutyl)-3,4,5-trimethoxybenzamide (1.37 mmol) and tetrahydrofuran (50 mL). Cool to 0° C. using ice-bath. Add potassium hydride (82.5 mg, 2.06 mmol). After 1 hour, add 2-picolyl chloride (175 mg, 1.37 mmol) (obtained from 2-picolyl chloride hydrochloride by treatment with excess sodium bicarbonate in dichloromethane, filtration, and evaporation in vacuo). Allow to warm to ambient temperature. After 18 hours, add potassium hydride (82.5 mg, 2.06 mmol) and 2-picolyl chloride (87 mg, 0.68 mmol). After 18 hours, cool to −78° C. and quench with methanol (5 mL) and morpholine (0.1 mL) followed by water (15 mL). Warm to ambient temperature and evaporate in vacuo to remove most of the methanol. Extract twice with dichloromethane. Combine the organic layers, dry over Na$_2$SO$_4$, filter, and evaporate in vacuo to give the title compound.

EXAMPLE 22

N-Methyl-N-(4-(4-(1-(thien-2-ylmethyl)-1H-benzimidazol-2-yl)[1,4]diazepan-1-yl)-2-phenylbutyl)-3,4,5-trimethoxybenzamide

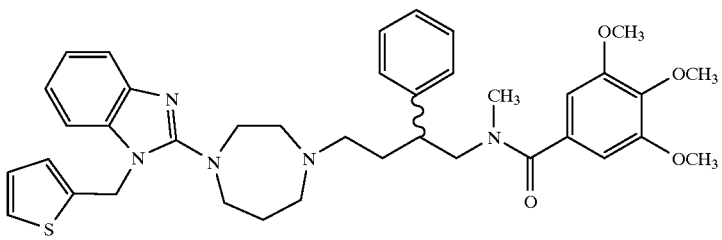

22.1 Synthesis of N-methyl-N-(4-(4-(1-(thien-2-ylmethyl)-1H-benzimidazol-2-yl)[1,4]diazepan-1-yl)-2-phenylbutyl)-3,4,5-trimethoxybenzamide Prepare by the method of Example 21.1 using N-Methyl-N-(4-(4-(1H-benzimidazol-2-yl)[1,4]diazepan-1-yl)-2-phenylbutyl)-3,4,5-trimethoxybenzamide and 2-(bromomethyl)thiophene (J. Am. Chem. Soc., 71 1201–1204 (1949)) to give the title compound.

PREPARATION 9.1

Synthesis of 1-(t-butoxycarbonyl)-4-(1H-benzimidazol-2-yl)[1,4]diazepane

Combine 4-(1H-benzimidazol-2-yl)[1,4]diazepane hydriodic acid salt in tetrahydrofuran (130 mL) and water (40 mL). Add sodium bicarbonate (4.26 g, 50.7 mmol) and cool the reaction mixture to about 5° C. using an ice-bath. Add a solution of di-t-butyl dicarbonate (5.54 g, 25.4 mmol) in tetrahydrofuran (20 mL). After the addition is complete warm the reaction mixture to ambient temperature. After 18 hours, concentrate the reaction mixture in vacuo to remove most to the tetrahydrofuran and extract with dichloromethane. Extract the organic layer with water and then brine. Dry the organic layers over Na$_2$SO$_4$, filter, and evaporate in vacuo to give, after drying, the title compound: mp; 225–226° C.

PREPARATION 9.2

Synthesis of 1-t-butoxycarbonyl-4-(1H-benzimidazol-2-yl)[1,4]diazepane

Combine 4-(1H-benzimidazol-2-yl)[1,4]diazepane hydrobromic acid salt (5.2 g, 13.8 mmol) and sodium bicarbonate (3.47 g, 41.3 mmol) in tetrahydrofuran/water (100 mL, 4/1). After 2 hours, evaporate the reaction mixture to remove most of the tetrahydrofuran, dilute with dichloromethane containing 5% methanol and extract with water. Dry the organic layer over Na$_2$SO$_4$, filter, and evaporate in vacuo to give the title compound: mp; 225–226° C. R$_f$=0.28 (silica gel, 5% methanol/dichloromethane/0.1% saturated aqueous ammonia).

PREPARATION 10

Synthesis of 4-(1-(4-cyanobutyl)-1H-benzimidazol-2-yl)[1,4]diazepane hydriodic acid salt Combine 1-(t-butoxycarbonyl)-4-1H-benzimidazol-2-yl)[1,4]diazepane (0.1 g, 0.32 mmol) and dimethylformamide (2 mL). Add sodium hydride (0.05 g, 0.32 mmol) and stir. After the gas evolution ceases, add 1-bromo-4-cyanobutane (0.05 g, 0.32 mmol). After 12 hours, dilute the reaction mixture with water and extract with dichloromethane. Separate the layers and extract the aqueous layer with dichloromethane. Combine the organic layer and extract five times with water and then brine. Dry the organic layers over Na$_2$SO$_4$, filter, and evaporate in vacuo to give a residue. Chromatograph the residue on silica gel eluting with 0.5% concentrated aqueous ammonia/3% methanol/dichloromethane to give 1-(t-butoxycarbonyl)-4-(1-(4-cyanobutyl)-1H-benzimidazol-2-yl)[1,4]diazepane: R$_f$=0.74 (silica gel, 0.5% concentrated aqueous ammonia/5% methanol/dichloromethane).

Combine 1-(t-butoxycarbonyl)-4-(1-(4-cyanobutyl)-1H-benzimidazol-2-yl)[1,4]diazepane (0.3 mmol) and dichloromethane (5 mL). Add aqueous 48% hydriodic acid solution (0.6 mmol). Heat to 40° C. After 6 hours, cool to ambient temperature dilute with diethyl ether (20 mL), and collect the solid to give the title compound.

EXAMPLE 22A

N-Methyl-N-(4-(4-(1-(4-cyanobutyl)-1H-benzimidazol-2-yl)[1,4]diazepan-1-yl)-2-(4-methoxyphenyl)butyl)-3,4,5-trimethoxybenzamide

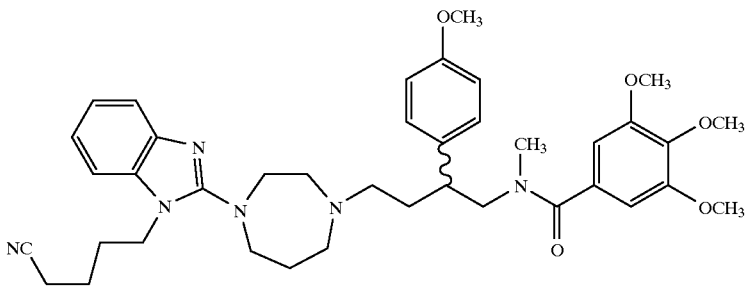

22A.1 Synthesis of N-methyl-N-(4-(4-(1-(4-cyanobutyl)-1H-benzimidazol-2-yl)[1,4]diazepan1-yl)-2-(4-methoxyphenyl)butyl)-3,4,5-trimethoxybenzamide Prepare by the method of Example 1.7 using N-methyl-N-(2-(4-methoxyphenyl)-4-methanesulfonylbutyl)-3,4,5-trimethoxybenzamide and 4-(1-(4-cyanobutyl)-1H-benzimidazol-2-yl)[1,4]diazepane hydriodic acid salt to give the title compound.

PREPARATION 11

Synthesis of 4-(1-(N-methylacetamido)-1H-benzimidazol-2-yl)[1,4]diazepane hydriodic acid salt Combine 1-(t-butoxycarbonyl)-4-1H-benzimidazol-2-yl)[1,4]diazepane (0.10 g, 0.32 mmol) and dimethylformamide (2 mL). Add sodium hydride (0.015 g, 0.62 mmol) and stir. After the gas evolution ceases, add N-methyl chloroacetamide (0.034 g, 0.32 mmol). After 12 hours, dilute the reaction mixture with water and extract with dichloromethane. Separate the layers and extract the aqueous layer with dichloromethane. Combine the organic layer and extract five times with water and then brine. Dry the organic layers over Na$_2$SO$_4$, filter, and evaporate in vacuo to give a residue. Chromatograph the residue on silica gel eluting with 0.5% concentrated aqueous ammonia/1.5% methanol/dichloromethane to give 1-(t-butoxycarbonyl)-4-(1-(N-methylacetamido)-1H-benzimidazol-2-yl)[1,4]diazepane: R$_f$=0.34 ( silica gel, 0.5% concentrated aqueous ammonia/5% methanol/dichloromethane). Combine 1-(t-butoxycarbonyl)-4-(1-(N-methylacetamido)-1H-benzimidazol-2-yl)[1,4]diazepane (0.6 mmol) and dichloromethane (10 mL). Add aqueous 48% hydriodic acid solution (1.2 mmol). Heat to 40° C. After 6 hours, cool to ambient temperature dilute with diethyl ether (40 mL), and collect the solid to give the title compound.

EXAMPLE 23

N-Methyl-N-(4-(4-(1-(N-methylacetamido)-1H-benzimidazol-2-yl) [1,4]diazepan-1-yl)-2-(4-methoxyphenyl)butyl)-3,4,5-trimethoxybenzamide

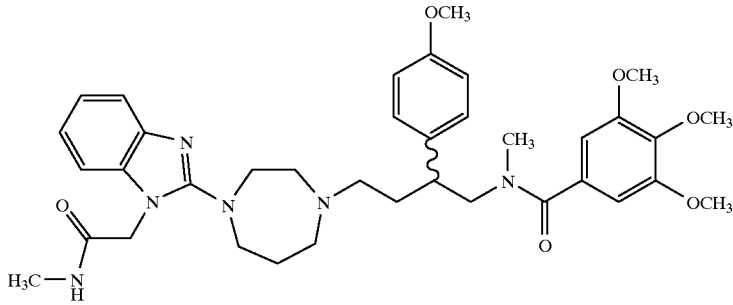

23.1 Synthesis of N-methyl-N-(4-(4-(1-(N-methylacetamido)-1H-benzimidazol-2-yl) [1,4]diazepan-1-yl)-2-(4-methoxyphenyl)butyl)-3,4,5-trimethoxybenzamide Prepare by the method of Example 1.7 using N-methyl-N-(2-(4-methoxyphenyl)-4-methanesulfonylbutyl)-3,4,5-trimethoxybenzamide and 4-(1-(N-methylacetamido)-1H-benzimidazol-2-yl)[1,4]diazepane hydriodic acid salt to give the title compound.

PREPARATION 12

Synthesis of 4-(1-(2-hydroxyethyl)-1H-benzimidazol-2-yl)[1,4]diazepane

Combine 4-(1-(2-ethoxyethyl)-1H-benzimidazol-2-yl)[1,4]diazepane (5.10 g, 9.4 mmol) and 48% hydrobromic acid (25 mL). Heat to reflux. After 18 hours, dilute with water and adjust the pH to 12 using aqueous 5 M sodium hydroxide solution. Extract three times with dichloromethane. Dry the combined organic layers over $Na_2SO_4$, filter, and evaporate in vacuo to give a residue. Combine the residue and methanol (50 mL). Add a solution of hydrochloric acid (5.0 mL, 4 M, 20 mmol) in dioxane. Evaporate in vacuo to give a residue. Combine the give residue and dichloromethane. Extract with a saturated aqueous solution of sodium bicarbonate. Dry the organic layers over $Na_2SO_4$, filter, and evaporate in vacuo to give the title compound.

PREPARATION 12A

Synthesis of 4-(1-(2-hydroxyethyl)-1H-benzimidazol-2-yl)[1,4]diazepane hydriodic acid salt Combine 2-(t-butyldimethylsilyloxy)ethyl bromide (116.2 g, 486 mmol), and sodium iodide (100 g, 663 mol) in acetone (350 mL) and dimethylformamide (25 mL). Heat to reflux. After 4 hours, cool, filter, and evaporate in vacuo to give a residue. Distill the residue to give 2-(t-butyldimethylsilyloxy)ethyl iodide: bp; 60° C. at 0.5 mm Hg. Combine 1-(t-butoxycarbonyl)-4-(1H-benzimidazol-2-yl)[1,4]diazepane (3.06 g, 9.67 mmol) and sodium hydride (0.43 g, 60% in oil, 10.64 mmol) in tetrahydrofuran (60 mL) and dimethylformamide (6 mL). After 2 hours, add 2-(t-butyldimethylsilyloxy)ethyl iodide (2.78 g, 9.67 mmol). After 20 hours, heat to reflux. After 4 hours, cool to ambient temperature and add ice to quench. Evaporate in vacuo to remove most of the tetrahydrofuran. Partition the evaporated reaction mixture between ethyl acetate (250 mL) and water (200 mL). Separate the layers and extract the organic layer with water. Dry the organic layer over $MgSO_4$, filter, and evaporate in vacuo to give a residue. Chromatograph the residue on silica gel eluting with ethyl acetate to give 1-(t-butoxycarbonyl)-4-(1-(2-(t-butyldimethylsilyloxy)ethyl)-1H-benzimidazol-2-yl)[1,4]diazepane: $R_f$=0.58 (silica gel, ethyl acetate).

Alternately, combine 1-(t-butoxycarbonyl)-4-(1H-benzimidazol-2-yl)[1,4]diazepane (1.72 g, 5.43 mmol) and sodium hydride (0.36 g, 60% in oil, 8.15 mmol) in dimethylformamide (40 mL). After 4 hours, add 2-(t-butyldimethylsilyloxy)ethyl iodide (1.56 g, 5.43 mmol). After 72 hours, heat to 80° C. After 3 hours, cool to ambient temperature and add ice to quench. Partition the reaction mixture between ethyl acetate (250 mL) and a saturated aqueous solution of sodium bicarbonate (200 mL). Separate the layers and extract the organic layer with water. Dry the organic layer over $MgSO_4$, filter, and evaporate in vacuo to give a residue. Chromatograph the residue on silica gel eluting with 40% ethyl acetate/dichloromethane to give 1-(t-butoxycarbonyl)-4-(1-(2-(t-butyldimethylsilyloxy)ethyl)-1H-benzimidazol-2-yl)[1,4]diazepane.

Combine 1-(t-butoxycarbonyl)-4-(1-(2-(t-butyldimethylsilyloxy)ethyl)-1H-benzimidazol-2-yl)[1,4]diazepane (4.22 g, 8.88 mmol), and methanol (60 mL). Add ammonium fluoride (1.97 g, 53.3 mmol). Heat to reflux. After 2 hours, cool the reaction mixture and partition between dichloromethane (300 mL) and a saturated aqueous solution of sodium bicarbonate (200 mL). Separate the layers and extract the organic layer three times with water and then brine. Dry the organic layer over $MgSO_4$, filter, and evaporate in vacuo to give a residue. Chromatograph the residue on silica gel eluting with ethyl acetate to give 1-(t-butoxycarbonyl)-4-(1-(2-hydroxyethyl)-1H-benzimidazol-2-yl)[1,4]diazepane: $R_f$=0.32 (silica gel, ethyl acetate).

Combine 1-(t-butoxycarbonyl)-4-(1-(2-hydroethyl)-1H-benzimidazol-2-yl)[1,4]diazepane (0.4 g, 1.11 mmol) and methanol (10 mL). Add hydriodic acid (5 mL, 57%) and heat to reflux. After 2 hours, cool to ambient temperature. Add diethyl ether (250 mL) to give a solid. Collect the solid by filtration to give the title compound.

EXAMPLE 24

N-Methyl-N-(4-(4-(1-(2-hydroxyethyl)-1H-benzimidazol-2-yl)[1,4]diazepan-1-yl)-2-phenylbutyl)-3,4,5-trimethoxybenzamide

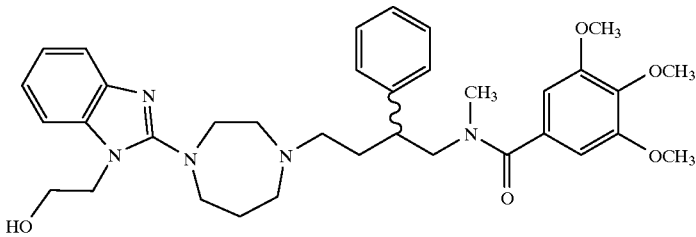

24.1.1 Synthesis of N-methyl-N-(4-(4-(2-hydroxyethyl)-1H-benzimidazol-2-yl)[1,4]diazepan-1-yl)-2-phenylbutyl)-3,4,5-trimethoxybenzamide Prepare by the method of Example 2.7 using N-methyl-N-(2-phenyl-4-methanesulfonylbutyl)-3,4,5-trimethoxybenzamide and 4-(1-(2-hydroxyethyl)-1H-benzimidazol-2-yl)[1,4]diazepane to give the title compound.

24.1.2 Synthesis of N-methyl-N-(4-(4-(2-hydroxyethyl)-1H-benzimidazol-2-yl)[1,4]diazepan-1-yl)-2-phenylbutyl)-3,4,5-trimethoxybenzamide Prepare by the method of Example 1.7 using N-methyl-N-(2-phenyl-4-methanesulfonylbutyl)-3,4,5-trimethoxybenzamide and 4-(1-(2-hydroxyethyl)-1H-benzimidazol-2-yl)[1,4]diazepane hydriodic acid salt to give the title compound.

EXAMPLE 25

N-Methyl-N-(4-(4-(1-(2-ethoxyethyl)-1H-benzimidazol-2-yl)[1,4]diazepan-1-yl)-2-(3-chlorophenyl)butyl)-3,4,5-trimethoxybenzamide

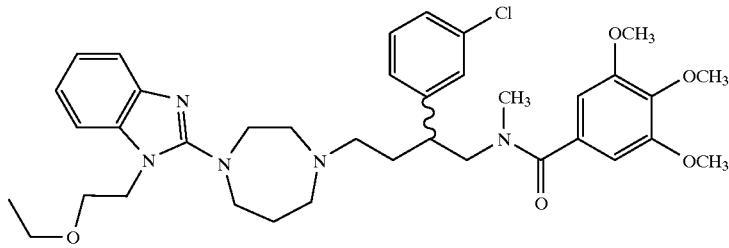

25.1 Synthesis of 2-(3-chlorophenyl)-4-(t-butyldimethylsilyloxy)butyronitrile

Prepare by the method of Example 1.1.1 using 3-chlorophenylacetonitrile and 1-(t-butyldimethylsilyloxy)-2-bromoethane to give the title compound.

25.2 Synthesis of 2-(3-chlorophenyl)-4-(t-butyldimethylsilyloxy)butylamine

Prepare by the method of Example 1.2 using 2-(3-chlorophenyl)-4-(t-butyldimethylsilyloxy)butyronitrile to give the title compound.

25.3 Synthesis of N-(2-(3-chlorophenyl)-4-(t-butyldimethylsilyloxy)butyl)-3,4,5-trimethoxybenzamide Prepare by the method of Example 1.3 using 2-(3-chlorophenyl)-4-(t-butyldimethylsilyloxy)butylamine and 3,4,5-trimethoxybenzoyl chloride to give the title compound.

25.4 Synthesis of N-methyl-N-(2-(3-chlorophenyl)-4-(t-butyldimethylsilyloxy)butyl)-3,4,5-trimethoxybenzamide Prepare by the method of Example 1.4 using N-(2-(3-chlorophenyl)-4-(t-butyldimethylsilyloxy)butyl)-3,4,5-trimethoxybenzamide to give the title compound.

25.5 Synthesis of N-methyl-N-(2-(3-chlorophenyl)-4-hydroxybutyl)-3,4,5-trimethoxybenzamide Prepare by the method of Example 1.5 using N-methyl-N-(2-(3-chlorophenyl)-4-(t-butyldimethylsilyloxy)butyl)-3,4,5-trimethoxybenzamide to give the title compound.

25.6 Synthesis of N-methyl-N-(2-(3-chlorophenyl)-4-methanesulfonylbutyl)-3,4,5-trimethoxybenzamide Prepare by the method of Example 1.6 using N-methyl-N-(2-(3-chlorophenyl)-4-hydroxybutyl)-3,4,5-trimethoxybenzamide to give the title compound.

25.7 Synthesis of N-methyl-N-(4-(4-(1-(2-ethoxyethyl)-1H-benzimidazol-2-yl)[1,4]diazepan-1-yl)-2-(3-chlorophenyl)butyl)-3,4,5-trimethoxybenzamide Prepare by the method of Example 1.7 using N-methyl-N-(2-(3-chlorophenyl)-4-methanesulfonylbutyl)-3,4,5-trimethoxybenzamide and 4-(1-(2-ethoxyethyl)-1H-benzimidazol-2-yl)[1,4]diazepane hydriodic acid salt to give the title compound.

EXAMPLE 26

N-Methyl-N-(4-(4-(1-(2-ethoxyethyl)-1H-benzimidazol-2-yl)[1,4]diazepan-1-yl)-2-(4-chlorophenyl)butyl)-3,4,5-trimethoxybenzamide

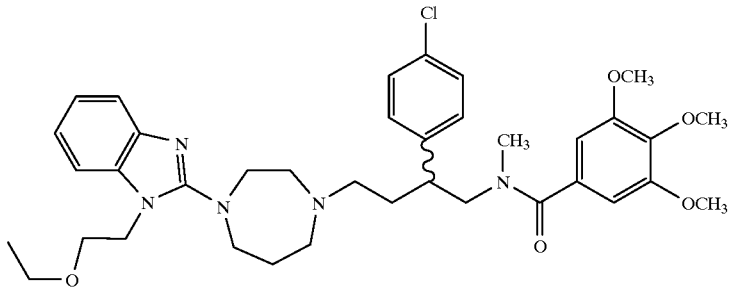

26.1 Synthesis of 2-(4-chlorophenyl)-4-(t-butyldimethylsilyloxy)butyronitrile

Prepare by the method of Example 1.1.1 using 4-chlorophenylacetonitrile and 1-(t-butyldimethylsilyloxy)-2-bromoethane to give the title compound.

26.2 Synthesis of 2-(4-chlorophenyl)-4-(t-butyldimethylsilyloxy)butylamine

Prepare by the method of Example 1.2 using 2-(4-chlorophenyl)-4-(t-butyldimethylsilyloxy)butyronitrile to give the title compound.

26.3 Synthesis of N-(2-(4-chlorophenyl)-4-(t-butyldimethylsilyloxy)butyl)-3,4,5-trimethoxybenzamide Prepare by the method of Example 1.3 using 2-(4-chlorophenyl)-4-(t-butyldimethylsilyloxy)butylamine and 3,4,5-trimethoxybenzoyl chloride to give the title compound.

26.4 Synthesis of N-methyl-N-(2-(4-chlorophenyl)-4-(t-butyldimethylsilyloxy)butyl)-3,4,5-trimethoxybenzamide Prepare by the method of Example 1.4 using N-(2-(4-chlorophenyl)-4-(t-butyldimethylsilyloxy)butyl)-3,4,5-trimethoxybenzamide to give the title compound.

26.5 Synthesis of N-methyl-N-(2-(4-chlorophenyl)-4-hydroxybutyl)-3,4,5-trimethoxybenzamide Prepare by the method of Example 1.5 using N-methyl-N-(2-(4-chlorophenyl)-4-(t-butyldimethylsilyloxy)butyl)-3,4,5-trimethoxybenzamide to give the title compound.

26.6 Synthesis of N-methyl-N-(2-(4-chlorophenyl)-4-methanesulfonylbutyl)-3,4,5-trimethoxybenzamide Prepare by the method of Example 1.6 using N-methyl-N-(2-(4-chlorophenyl)-4-hydroxybutyl)-3,4,5-trimethoxybenzamide to give the title compound.

26.7 Synthesis of N-methyl-N-(4-(4-(1-(2-ethoxyethyl)-1H-benzimidazol-2-yl)[1,4]diazepan-1-yl)-2-(4-chlorophenyl)butyl)-3,4,5-trimethoxybenzamide Prepare by the method of Example 1.7 using N-methyl-N-(2-(4-chlorophenyl)-4-methanesulfonylbutyl)-3,4,5-trimethoxybenzamide and 4-(1-(2-ethoxyethyl)-1H-benzoimidazol-2-yl)[1,4]diazepane hydriodic acid salt to give the title compound.

EXAMPLE 27

N-Methyl-N-(4-(4-(1-(2-ethoxyethyl)-1H-benzimidazol-2-yl)[1,4]diazepan-1-yl)-2-(3,4-dimethylphenyl)butyl)-3,4,5-trimethoxybenzamide

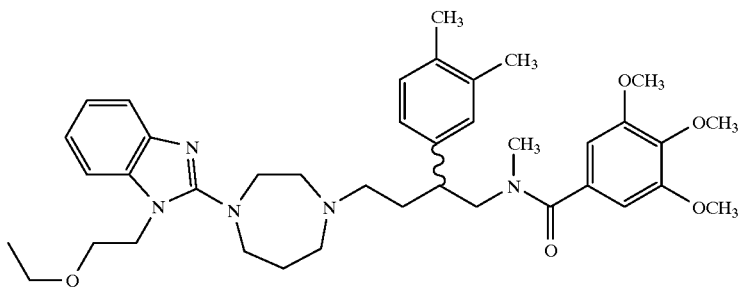

27.1 Synthesis of 2-(3,4-dimethylphenyl)-4-(t-butyldimethylsilyloxy)butyronitrile Prepare by the method of Example 1.1.1 using 3,4-dimethylphenylacetonitrile and 1-(t-butyldimethylsilyloxy)-2-bromoethane to give the title compound.

27.2 Synthesis of 2-(3,4-dimethylphenyl)-4-(t-butyldimethylsilyloxy)butylamine

Prepare by the method of Example 1.2 using 2-(3,4-dimethylphenyl)-4-(t-butyldimethylsilyloxy)butyronitrile to give the title compound.

27.3 Synthesis of N-(2-(3,4-dimethylphenyl)-4-(t-butyldimethylsilyloxy)butyl)-3,4,5-trimethoxybenzamide Prepare by the method of Example 1.3 using 2-(3,4-dimethylphenyl)-4-(t-butyldimethylsilyloxy)butylamine and 3,4,5-trimethoxybenzoyl chloride to give the title compound.

27.4 Synthesis of N-methyl-N-(2-(3,4-dimethylphenyl)-4-(t-butyldimethylsilyloxy)butyl)-3,4,5-trimethoxybenzamide Prepare by the method of Example 1.4 using N-(2-(3,4-dimethylphenyl)-4-(t-butyldimethylsilyloxy)butyl)-3,4,5-trimethoxybenzamide to give the title compound.

27.5 Synthesis of N-methyl-N-(2-(3,4-dimethylphenyl)-4-hydroxybutyl)-3,4,5-trimethoxybenzamide Prepare by the method of Example 1.5 using N-methyl-N-(2-(3,4-dimethylphenyl)-4-(t-butyldimethylsilyloxy)butyl)-3,4,5-trimethoxybenzamide to give the title compound.

27,6 Synthesis of N-methyl-N-(2-(3,4-dimethylphenyl)-4-methanesulfonylbutyl)-3,4,5-trimethoxybenzamide Prepare by the method of Example 1.6 using N-methyl-N-(2-(3,4-dimethylphenyl)-4-hydroxybutyl)-3,4,5-trimethoxybenzamide to give the title compound.

27.7 Synthesis of N-methyl-N-(4-(4-(1-(2-ethoxyethyl)-1H-benzimidazol-2-yl)[1,4]diazepan-1-yl)-2-(3,4-dimethylphenyl)butyl)-3,4,5-trimethoxybenzamide Prepare by the method of Example 1.7 using N-methyl-N-(2-(3,4-dimethylphenyl)-4-methanesulfonylbutyl)-3,4,5-trimethoxybenzamide and 4-(1-(2-ethoxyethyl)-1H-benzimidazol-2-yl)[1,4]diazepane hydriodic acid salt to give the title compound.

EXAMPLE 28

N-Methyl-N-(4-(4-(1-(imidazol-2-ylmethyl)-1H-benzimidazol-2-yl)[1,4]diazepan-1-yl)-2-phenylbutyl)benzamide

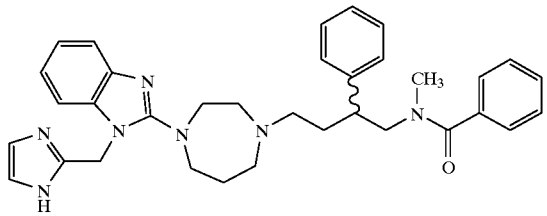

28.1 Synthesis of N-methyl-N-(4-(4-(1-(1-benzylimidazol-2-ylmethyl)-1H-benzimidazol-2-yl)[1,4]diazepan-1-yl)-2-phenylbutyl)benzamide Prepare by the method of Example 21.1 using N-methyl-N-(4-(4-(1H-benzimidazol-2-yl)[1,4]diazepan-1-yl)-2-phenylbutyl)benzamide and 1H-benzyl-imidazol-2-ylmethylchloride hydrochloride to give the title compound.

28.2 Synthesis of N-methyl-N-(4-(4-(1-(imidazol-2-ylmethyl)-1H-benzimidazol-2-yl)[1,4]diazepan-1-yl)-2-phenylbutyl)benzamide Combine N-methyl-N-(4-(4-(1-(1-benzylimidazol-2-ylmethyl)-1H-benzimidazol-2-yl)[1,4]diazepan-1-yl)-2-phenylbutyl)benzamide (5 mmol) and 10% palladium-on-carbon (1.5 g) in methanol (50 mL). Add anhydrous ammonium formate (25 mmol). Heat to reflux. After 18 hours, filter, rinse with dichloromethane, and evaporate the filtrate in vacuo to give the title compound.

EXAMPLE 29

N-Methyl-N-(4-(4-(1H-benzimidazol-2-yl)[1,4]diazepan-1-yl)-2-(3-chlorophenyl)butyl)-3,4,5-trimethoxybenzamide

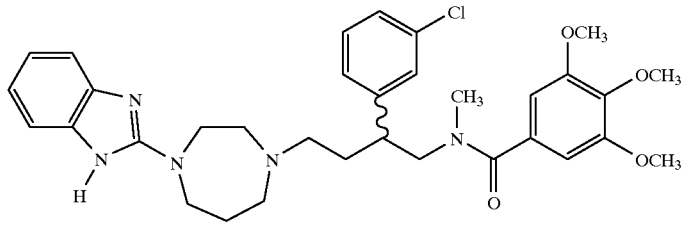

29.1 Synthesis of N-methyl-N-(4-(4-(1H-benzimidazol-2-yl)[1,4]diazepan-1-yl)-2-(3-chlorophenyl)butyl)-3,4,5-trimethoxybenzamide Prepare by the method of Example 1.7 using N-methyl-N-(2-(3-chlorophenyl)-4-methanesulfonylbutyl)-3,4,5-trimethoxybenzamide and 4-(1H-benzimidazol-2-yl)[1,4]diazepane to give the title compound.

PREPARATION 13

Synthesis of 4-(1-(2-(fur-2-ylmethoxy)ethyl)-1H-benzimidazol-2 -yl)[1,4]diazepane Combine furfuryl alcohol (1 mL, 11.6 mmol) and tetrahydrofuran (20 mL). Add portionwise sodium hydride (0.57 g, 60% in oil, 14 mmol). After gas evolution ceases, add ethyl bromoacetate (1.3 mL, 11.7 mmol). Heat to reflux. After 2.5 hours cool to ambient temperature. After 18 hours, partition the reaction mixture between ethyl acetate and water. Separate the aqueous layer and extract twice with ethyl acetate. Combine the organic layers and extract with saturated aqueous sodium chloride solution, dry over $Na_2SO_4$, filter, and concentrate in vacuo to give a residue.

Chromatograph the residue on silica gel eluting with 1% ethyl acetate/dichloromethane to give ethyl fur-2-ylmethoxyacetate: $R_f$=0.62 (silica gel, 5% ethyl acetate/dichloromethane).

Combine ethyl 2-fur-2-ylmethoxyaceate (1.2 g, 6.5 mmol) and tetrahydrofuran (10 mL). Cool in an ice-bath. Add dropwise a solution of lithium aluminum hydride (8.0 mL, 1.0 M in THF, 8.0 mmol). After 2 hours, add water (0.3 mL), add 15% sodium hydroxide solution (0.3 mL), and add water (0.9 mL). Stir vigorously. After 15 minutes, filter the reaction mixture and dry the filtrate over $Na_2SO_4$, filter, and concentrate in vacuo to give a residue. Chromatograph the residue on silica gel eluting with 2% ethyl acetate/dichloromethane to give fur-2-ylmethyl 2-hydroxyethyl ether: $R_f$=0.22 (silica gel, 5% acetone/dichloromethane).

Combine fur-2-ylmethyl 2-hydroxyethyl ether (10 mmol), and N,N-diisopropylethylamine (4.0 mL, 23 mmol), and dichloromethane (20 mL). Cool in an ice-bath. Add dropwise, methanesulfonyl chloride (1.0 mL, 13 mmol). After 1.5 hours, extract the reaction mixture with 1 M aqueous hydrochloric acid solution, saturated aqueous sodium bicarbonate solution, and saturated aqueous sodium chloride solution. Dry the organic layer over $Na_2SO_4$, filter, and evaporate in vacuo to obtain fur-2-ylmethyl 2-methanesulfonylethyl ether.

Combine 1-ethoxycarbonyl-4-(1H-benzimidazol-2-yl)[1,4]diazepane (1.6 mmol) and tetrahydrofuran (10 mL). Cool to −78° C. Add dropwise, a solution of potassium bis(trimethylsilyl)amide (3.6 mL, 0.5 M in toluene, 1.8 mmol). After 30 minutes, add fur-2-ylmethyl 2-methanesulfonylethyl ether (1.8 mmol). Warm to ambient temperature and heat to reflux. After 18 hours, cool to ambient temperature and add water. Separate the organic layer and extract the aqueous layer with dichloromethane. Dry the combined organic layers over Na$_2$SO$_4$, filter, and evaporate in vacuo to give 1-ethoxycarbonyl-4-(1-(2-(fur-2-ylmethoxy)ethyl)-1H-benzimidazol-2-yl)[1,4]diazepane.

Combine 1-ethoxycarbonyl-4-(1-(2-(fur-2-ylmethoxy)ethyl)-1H-benzimidazol-2-yl)[1,4]diazepane (1 mmol), potassium hydroxide (1.2 mmol), and isopropanol (20 mL). Heat to reflux. After 18 hours, evaporate in vacuo to give a residue. Combine the residue and water. Extract with dichloromethane. Dry the organic layer over MgSO$_4$, filter, and evaporate in vacuo to give the title compound.

EXAMPLE 30

N-Methyl-N-(4-(4-(1-(2-(fur-2-ylmethoxy)ethyl)-1H-benzimidazol-2-yl)[1,4]diazepan-1-yl)-2-(4-fluorophenyl)butyl)-3,4,5-trimethoxybenzamide

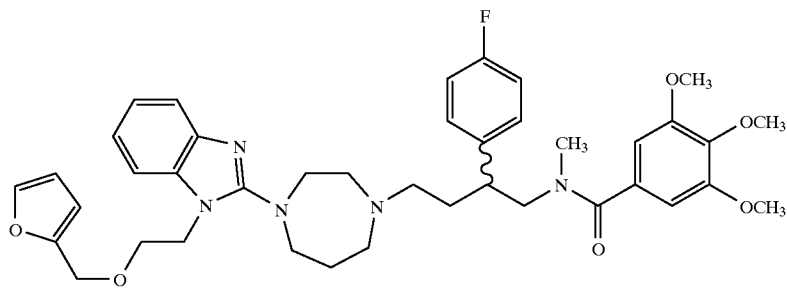

Prepare by the method of Example 1.7 using N-methyl-N-(2-(3,4-dichlorophenyl)-4-methanesulfonylbutyl)benzamide and 4-(1-(2-(fur-2-ylmethoxy)ethyl)-1H-benzimidazol-2-yl)[1,4]diazepane to give the title compound.

PREPARATION 14

Synthesis of 1-ethoxycarbonyl-4-(1H-benzimidazol-2-yl)[1,4]diazerane

Combine 1-ethoxycarbonyl[1,4]diazepane (18.0 g, 104 mmol) and 2-chlorobenzimidazole (7.93 g, 52 mmol). Heat to 130° C. After 4 hours, cool to ambient temperature and add hot methanol to dissolve the reaction mixture. Add a saturated aqueous solution of sodium bicarbonate (150 mL) and concentrate in vacuo to remove most of the methanol. Combine the aqueous reaction mixture and 95/5 diethyl ether/ethyl acetate. Separate the aqueous layer and extract three times with dichloromethane. Combine the dichloromethane layers, dry over Na$_2$SO$_4$, filter, and evaporate in vacuo to give a residue. Triturate the residue with ethyl acetate (100 mL) to give a solid. Chromatograph on silica gel eluting with 10% methanol/dichloromethane/ 0.1% concentrated aqueous ammonia to give a residue. Triturate that residue with 9/1 diethyl ether/ethyl acetate to give a solid. Collect solid by filtration and dry in vacuo to give the title compound: mp; 161–162° C.

PREPARATION 15

Synthesis of 4-(1-(N-methylacetamido)-1H-benzimidazol-2-yl)[1,4]diazepane hydriodic acid salt Combine 1-(t-butoxycarbonyl)-4-(1H-benzimidazol-2-yl)[1,4]diazepane (0.5 g, 1.6 mmol) and dimethylformamide (20 mL). Add sodium hydride (0.08 g, 3.2 mmol). After 12 hours, add N-methyl-1-chloroacetamide (0.34 g, 3.14 mmol). After 12 hours, add N-methyl-1-chloroacetamide (0.17 g, 1.6 mmol). After 12 hours, heat to 70° C. After 4 hours, cool to ambient temperature and partition the reaction mixture between water (10 mL) and dichloromethane (100 mL). Separate the layers, dry the organic layer over Na$_2$SO$_4$, filter, and evaporate in vacuo to give a residue. Chromatograph the residue on silica gel eluting with 1.2% methanol/dichloromethane/0.5% saturated aqueous ammonia solution to give 1-(t-butoxycarbonyl)-4-(1-(N-methylacetamido)-1H-benzimidazol-2-yl)[1,4]diazepane: R$_f$=0.24 (silica gel, 1.8% methanol/dichloromethane/0.5% saturated aqueous ammonia solution).

Combine 1-(t-butoxycarbonyl)-4-(1-(N-methylacetamido)-1H-benzimidazol-2-yl)[1,4]diazepane (0.18 g, 0.48 mmol) and dichloromethane (10 mL). Add hydriodic acid (0.17 mL, 57%, 0.95 mmol) and warm to 40° C. After 3 hours, cool to ambient temperature and evaporate in vacuo to give a residue. Combine the residue and diethyl ether with stirring to give a solid. Collect the solid by filtration to give, after drying, the title compound.

EXAMPLE 31

N-Methyl-N-(4-(4-(1-(N-methylacetamido)-1H-benzimidazol-2-yl)[1,4]diazepan-1-yl)-2-(4-fluorophenyl)butyl)-3,4,5-trimethoxybenzamide

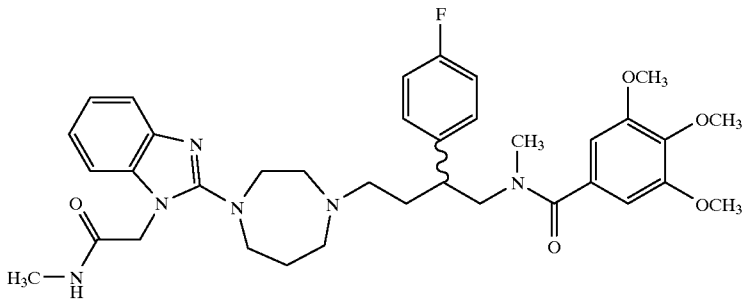

31.1 Synthesis of N-methyl-N-(4-(4-(1-(N-methylacetamido)-1H-benzimidazol-2-yl)[1,4]diazepan-1-yl)-2-(4-fluorophenyl)butyl)-3,4,5-trimethoxybenzamide Prepare by the method of Example 1.7 using 4-(1-(N-methylacetamido)-1H-benzimidazol-2-yl)[1,4]diazepane hydriodic acid salt and N-methyl-N-(2-(4-fluorophenyl)-4-methanesulfonylbutyl)-3,4,5-trimethoxybenzamide to give the title compound.

PREPARATION 16

Synthesis of 4-(1-(2-cyanomethyloxyethyl)-1H-benzimidazol-2-yl)[1,4]diazepane hydriodic acid salt Combine 4-(1-(2-ethoxyethyl)-1H-benzimidazol-2-yl)[1,4]diazepane (5.95 g, 20.6 mmol) and 48% hydrobromic acid (50 mL). Heat to reflux. After 3.5 hours, cool the reaction mixture and dilute with a solution of sodium hydroxide (23 g, 0.57 mmol) in water (250 mL). Extract three times with dichloromethane. Combine the aqueous layer, dichloromethane (200 mL), and sodium chloride (50 g) and stir. After 18 hours, separate the layers and combine all the organic layers, dry over $Na_2SO_4$, filter, and evaporate in vacuo to give 4-(1-(2-hydroxyethyl)-1H-benzimidazol-2-yl)[1,4]diazepane.

Combine 4-(1-(2-hydroxyethyl)-1H-benzimidazol-2-yl)[1,4]diazepane (1.30 g, 5.0 mmol), tetrahydrofuran (40 mL), and water (10 mL). Add dropwise a solution of di-t-butyl dicarbonate (1.09 g, 5.0 mmol) in tetrahydrofuran (15 mL). After 18 hours, concentrate the reaction mixture in vacuo to remove most of the tetrahydrofuran and combine the concentrated reaction mixture with dichloromethane. Separate the layers, dry over $Na_2SO_4$, filter, and evaporate in vacuo to give a residue. Chromatograph the residue on silica gel eluting with ethyl acetate to give 1-(t-butoxycarbonyl)-4-(1-(2-hydroxyethyl)-1H-benzimidazol-2-yl)[1,4]diazepane: $R_f$=0.25 (silica gel, ethyl acetate).

Alternately, combine 4-(1-(2-hydroxyethyl)-1H-benzimidazol-2-yl)[1,4]diazepane (4.9 g, 18.8 mmol) and dichloromethane (120 mL). Add dropwise a solution of di-t-butyl dicarbonate (4.31 g, 19.7 mmol) in dichloromethane (20 -mL). After 72 hours, concentrate the reaction mixture in vacuo to give a residue. Chromatograph the residue on silica gel eluting with ethyl acetate to give upon standing 1-(t-butoxycarbonyl)-4-(1-(2-hydroxyethyl)-1H-benzimidazol-2-yl)[1,4]diazepane: mp: 108–112° C. $R_f$=0.25 (silica gel, ethyl acetate).

Combine 1-(t-butoxycarbonyl)-4-(1-(2-hydroxyethyl)-1H-benzimidazol-2-yl)[1,4]diazepane (1.7 g, 4.7 mmol), tetrahydrofuran (70 mL), and dimethylformamide (8 mL). Cool in an ice bath. Add with stirring, sodium hydride (0.28 g, 60% in oil, 7.0 mmol). After 3 hours, warm to ambient temperature. After 30 minutes, again cool in an ice bath and add bromoacetonitrile (1.12 g, 9.36 mmol). Warm to ambient temperature. After 18 hours, again cool in an ice bath and add a saturated aqueous solution of ammonium chloride (5 mL) and then water (5 mL). Concentrate the reaction mixture in vacuo to remove most to the tetrahydrofuran and dilute with dichloromethane (150 mL). Extract three times with water, dry the organic layer over $Na_2SO_4$, filter, and evaporate in vacuo to give a residue. Chromatograph the residue on silica gel eluting with ethyl acetate to give 1-(t-butoxycarbonyl)-4-(1-(2-cyanomethyloxyethyl)-1H-benzimidazol-2-yl)[1,4]diazepane: $R_f$=0.38 (silica gel, ethyl acetate).

Combine 1-(t-butoxycarbonyl)-4-(1-(2-cyanomethyloxyethyl)-1H-benzimidazol-2-yl)[1,4]diazepane (0.36 g, 0.91 mmol), dichloromethane (15 mL), and methanol (5 mL). Cool in an ice bath and add hydriodic acid (0.25 mL, 57%, 1.86 mmol). Warm to ambient temperature. After 5 hours, concentrate the reaction mixture in vacuo to give a residue. Combine the residue and diethyl ether (40 mL) and stir. After 18 hours, decant the solvent, add diethyl ether, and stir to give a solid. Collect the solid by filtration and dry to give the title compound.

EXAMPLE 32

N-Methyl-N-(4-(4-(1-(2-cyanomethyloxyethyl)-1H-benzimidazol-2-yl)[1,4]diazepan-1-yl)-2-(4-fluorophenyl)butyl)-3,4,5-trimethoxybenzamide

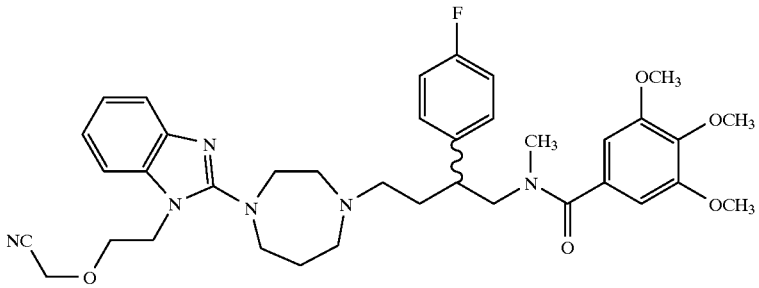

32.1 Synthesis of N-methyl-N-(4-(4-(1-(2-cyanomethyloxyethyl)-1H-benzimidazol-2-yl)[1,4]diazepan-1-yl)-2-(4-fluorophenyl)butyl)-3,4,5-trimethoxybenzamide Prepare by the method of Example 1.7 using 4-(1-(2-cyanomethyloxyethyl)-1H-benzimidazol-2-yl)[1,4]diazepane hydriodic acid salt and N-methyl-N-(2-(4-fluorophenyl)-4-methanesulfonylbutyl)-3,4,5-trimethoxybenzamide to give the title compound.

PREPARATION 17

Synthesis of 2-methoxy-5-(1H-tetrazol-1-yl)benzoyl chloride

Combine 2-hydroxy-5-nitrobenzoic acid (21.5 g, 117 mmol), potassium carbonate (162.3 g, 1.174 mol), and methyl iodide (136.8 g, 96.4 mmol) in acetone (500 mL). Heat to reflux. After 18 hours, cool the reaction mixture to ambient temperature and add methyl iodide (136.8 g, 96.4 mmol). Again, heat to reflux. After 56 hours, cool the reaction mixture to ambient temperature and filter, rinse with acetone, and evaporate the filtrate in vacuo to give a residue. Recrystallize the residue from ethanol to give a second residue. Combine the second residue and chloroform (about 100 mL), filter, and evaporate the filtrate in vacuo to give methyl 2-methoxy-5-nitrobenzoate. $R_f$=0.38 (silica gel, ethyl acetate/hexane 1/1).

Combine methyl 2-methoxy-5-nitrobenzoate (13.3 g, 63 mmol) and methanol. Add 5% palladium-on-carbon (0.66 g). Hydrogenate on a pressure apparatus at 50 psi. After 17 hours, filter through celite to remove the catalyst and evaporate the filtrate in vacuo to give a residue. Combine the residue and dichloromethane and extract with water. Dry the organic layer over $Na_2SO_4$, filter, and evaporate in vacuo to give methyl 2-methoxy-5-aminobenzoate. $R_f$=0.18 (silica gel, ethyl acetate/methanol 1/1). Elemental Analysis calculated for $C_9H_{11}NO_3$: C, 59.66; H, 6.12; N, 7.73. Found: C, 59.44; H, 6.04; N, 7.62.

Combine methyl 2-methoxy-5-aminobenzoate (3.94 g, 21.7 mmol) and triethyl orthoformate (12.8 g, 86.7 mmol) in glacial acetic acid (20 mL). After 20 hours, concentrate the reaction mixture in vacuo to remove ethanol. Add glacial acetic acid (20 mL) and sodium azide (5.64 g, 86.7 mmol). Heat to 70° C. After 1 hour, add glacial acetic acid (10 mL) and continue to heat to 70° C. After an additional hour, cool the reaction mixture to ambient temperature, dilute with water (500 mL). Collect the solid by filtration, rinse with water, and dry to give methyl 2-methoxy-5-(1H-tetrazol-1-yl)benzoate.

Combine methyl 2-methoxy-5-(1H-tetrazol-1-yl)benzoate (2.86 g, 12.2 mmol) and a 1 M aqueous solution of sodium hydroxide (13.43 mL, 13.43 mmol) in methanol/water (100 mL, 5:1 vol./vol.). Heat to reflux. After 4 hours, concentrate in vacuo to remove most of the methanol, add water (50 mL), and adjust the pH to about 4 using a 1 M aqueous hydrochloric acid solution. Evaporate in vacuo to give a solid, slurry the solid with water, filter, and dry to give 2-methoxy-5-(1H-tetrazol-1-yl)benzoic acid.

Alternately, combine methyl 2-methoxy-5-(1H-tetrazol-1-yl)benzoate (13.3 g, 56.8 mmol) and methanol (150 mL). Add 1 M aqueous solution of sodium hydroxide (62.5 mL, 62.5 mmol). Heat to reflux. After 30 minutes, add methanol (50 mL) and water (50 mL) and continue the heat at reflux. After 1 hour, concentrate in vacuo to remove most of the solvent. Adjust the pH to about 1 to 2 using a 1 M aqueous hydrochloric acid solution to give a solid. Collect the solid by filtration, rinse with water, and dry to give 2-methoxy-5-(1H-tetrazol-1-yl)benzoic acid.

Combine 2-methoxy-5-(1H-tetrazol-1-yl)benzoic acid (1.2 g, 5.5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

EXAMPLE 33

N-Methyl-N-(4-(4-(1-(2-ethoxyethyl)-1H-benzimidazol-2-yl)[1,4]diazepan-1-yl)-2-(4-fluorophenyl)butyl)-2-methoxy-5-(1H-tetrazol-1-yl)benzamide

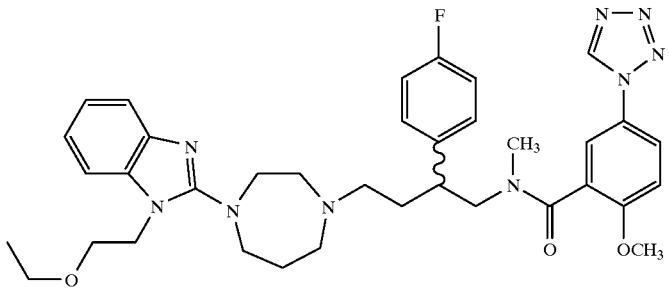

33.1 Synthesis of N-(2-(4-fluorophenyl)-4-(t-butyldimethylsilyloxy)butyl)-2-methoxy-5-(1H-tetrazol-1-yl)benzamide Combine 2-(4-fluorophenyl)-4-(t-butyldimethylsilyloxy)butylamine (5.0 g, 16.8 mmol) and sodium bicarbonate (7.0 g, 83 mmol) in acetone (50 mL) and water (50 mL). Add 2-methoxy-5-(1H-tetrazol-1-yl)benzoyl chloride (3.3 g, 14.55 mmol). After 18 hours, dilute the reaction mixture with ethyl acetate, separate the layers, and extract the organic layer with a saturated aqueous solution of sodium bicarbonate, water, and then with brine. Dry the organic layer over MgSO$_4$, filter, and concentrate in vacuo to obtain a residue. Chromatograph the residue on silica gel eluting sequentially with 50% ethyl acetate/hexane and then 75% ethyl acetate/hexane to give, after drying, the title compound: R$_f$=0.58 (silica gel, ethyl acetate).

33.2 Synthesis of N-methyl-N-(2-(4-fluorophenyl)-4-(t-butyldimethylsilyloxy)butyl)-2-methoxy-5-(1H-tetrazol-1-yl)benzamide Combine N-(2-(4-fluorophenyl)-4-(t-butyldimethylsilyloxy)butyl)-2-methoxy-5-(1H-tetrazol-1-yl)benzamide (3.57 g, 7.13 mmol) in tetrahydrofuran (20 mL). Cool in a dry-ice/acetone bath. Add a solution of sec-butyllithium (7.2 mL, 1.3 M in cyclohexane, 9.5 mmol). After 30 minutes, add iodomethane (2.0 mL, 32.1 mmol). Warm to ambient temperature and then heat to reflux. After 18 hours, cool, dilute the reaction mixture with ethyl acetate, and extract with a saturated aqueous solution of sodium bicarbonate and then brine. Dry the organic layer over Na$_2$SO$_4$, filter, and concentrate in vacuo to give a residue. Chromatograph the residue on silica gel eluting with 3/7 ethyl acetate/hexane to give, after drying, the title compound: R$_f$=0.63 (silica gel, ethyl acetate).

33.3 Synthesis of N-methyl-N-(2-(4-fluorophenyl)-4-hydroxybutyl)-2-methoxy-5-(1H-tetrazol-1-yl)benzamide Prepare by the method of Example 1.5 using N-methyl-N-(2-(4-fluorophenyl)-4-(t-butyldimethylsilyloxy)butyl)-2-methoxy-5-(1H-tetrazol-1-yl)benzamide to give the title compound: R$_f$=0.18 (silica gel, ethyl acetate).

33.4 Synthesis of N-methyl-N-(2-(4-fluorophenyl)-4-methanesulfonylbutyl)-2-methoxy-5-(1H-tetrazol-1-yl)benzamide Prepare by the method of Example 1.6 using N-methyl-N-(2-(4-fluorophenyl)-4-hydroxybutyl)-2-methoxy-5-(1H-tetrazol-1-yl)benzamide to give the title compound.

33.5 Synthesis of N-methyl-N-(4-(4-(1-(2-ethoxyethyl)-1H-benzimidazol-2-yl)[1,4]diazepan-1-yl)-2-(4-fluorophenyl)butyl)-2-methoxy-5-(1H-tetrazol-1-yl)benzamide Prepare by the method of Example 1.7 using N-methyl-N-(2-(4-fluorophenyl)-4-methanesulfonylbutyl)-2-methoxy-5-(1H-tetrazol-1-yl)benzamide and 4-(2-ethoxyethyl)-1H-benzimidazol-2-yl)[1,4]diazepane hydriodic acid salt to give the title compound.

EXAMPLE 34

N-Methyl-N-(4-(4-(1-(2-ethoxyethyl)-1H-benzimidazol-2-yl)[1,4]diazepan-1-yl)-2-(3,4-dichlorophenyl)butyl)-2-methoxy-5-(1H-tetrazol-1-yl)benzamide

34.1 Synthesis of N-(2-(3,4-dichlorophenyl)-4-(t-butyldimethylsilyloxy)butyl)-2-methoxy-5-(1H-tetrazol-1-yl)benzamide Prepare by the method of Example 33.1 using 2-(3,4-dichlorophenyl)-4-(t-butyldimethylsilyloxy)butylamine to give the title compound.

34.2 Synthesis of N-methyl-N-(2-(3,4-dichlorophenyl)-4-(t-butyldimethylsilyloxy)butyl)-2-methoxy-5-(1H-tetrazol-1-yl)benzamide Prepare by the method of Example 1.4 using N-(2-(3,4-dichlorophenyl)-4-(t-butyldimethylsilyloxy)butyl)-2-methoxy-5-(1H-tetrazol-1-yl)benzamide to give the title compound.

34.3 Synthesis of N-methyl-N-(2-(3,4-dichlorophenyl)-4-hydroxybutyl)-2-methoxy-5-(1H-tetrazol-1-yl)benzamide Prepare by the method of Example 1.5 using N-methyl-N-(2-(3,4-dichlorophenyl)-4-(t-butyldimethylsilyloxy)butyl)-2-methoxy-5-(1H-tetrazol-1-yl)benzamide to give the title compound.

34.4 Synthesis of N-methyl-N-(2-(3,4-dichlorophenyl)-4-methanesulfonylbutyl)-2-methoxy-5-(1H-tetrazol-1-yl)benzamide Prepare by the method of Example 1.6 using N-methyl-N-(2-(3,4-dichlorophenyl)-4-hydroxybutyl)-2-methoxy-5-(1H-tetrazol-1-yl)benzamide to give the title compound.

34.5 Synthesis of N-methyl-N-(4-(4-(1-(2-ethoxyethyl)-1H-benzimidazol-2-yl)[1,4]diazepan-1-yl)-2-(3,4-dichlorophenyl)butyl)-2-methoxy-5-(1H-tetrazol-1-yl)benzamide Prepare by the method of Example 1.7 using N-methyl-N-(2-(3,4-dichlorophenyl)-4-methanesulfonylbutyl)-2-methoxy-5-(1H-tetrazol-1-yl)benzamide and 4-(2-ethoxyethyl)-1H-benzimidazol-2-yl)[1,4]diazepane hydriodic acid salt to give the title compound.

PREPARATION 19

Synthesis of 2,2,2-trifluoroethyl trifluoromethanesulfonate

Combine 2,2,2-trifluoroethanol (12.4 mL g, 170 mmol), pyridine (13.6 mL, 170 mmol), and dichloromethane (40 mL). Cool in an ice bath. Add trifluoromethanesulfonic anhydride (50 g, 196 mmol) over about 45 minutes. After 15 minutes, add water, separate the layers and extract the organic layer with water. Dry the organic layer over MgSO$_4$, filter, and concentrate through a short path distillation apparatus to give the title compound: bp 89–91° C.

EXAMPLE 35

N-Methyl-N-(4-(4-(1-(2,2,2-trifluoroethyl)-1H-benzimidazol-2-yl)[1,4]diazepan-1-yl)-2-phenylbutyl)-3,4,5-trimethoxybenzamide

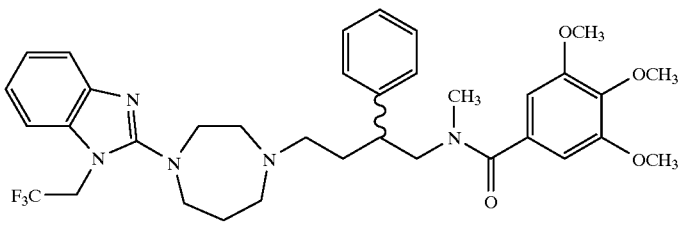

35.1 Synthesis of N-methyl-N-(4-(4-(1-(2,2,2-trifluoroethyl)-1H-benzimidazol-2-yl)[1,4]diazepan-1-yl)-2-phenylbutyl)-3,4,5-trimethoxybenzamide Prepare by the method of Example 21.1 using 2,2,2-trifluoroethyl trifluoromethanesulfonate to give the title compound.

PREPARATION 20

Synthesis of 4-(1-(allyl)-1H-benzimidazol-2-yl)[1,4]diazepane hydriodic acid salt Combine 1-t-butoxycarbonyl-4-(1H-benzimidazol-2-yl)[1,4]diazepane (0.8 g, 2.5 mmol) in dimethylformamide (10 mL). Add sodium hydride (0.13 g, 60% in oil, 3.25 mmol). After about 30 minutes, when the gas evolution ceases, add allyl bromide (0.35 mL 4.0 mmol). Heat to 75° C. After 4 hours, dilute with ethyl acetate and extract with a saturated aqueous sodium bicarbonate solution and then brine. Dry the organic layer over MgSO$_4$, filter, and evaporate in vacuo to give 1-t-butoxycarbonyl-4-(1-(allyl)-1H-benzimidazol-2-yl)[1,4]diazepane: R$_f$=0.83 (silica gel, 10% methanol/dichloromethane/0.1% concentrated aqueous ammonia).

Combine 1-t-butoxycarbonyl-4-(1-(allyl)-1H-benzimidazol-2-yl)[1,4]diazepane (0.9 g, 2.5 mmol) and ethanol (10 mL). Add aqueous hydriodic acid (10 mL, 57%). Heat to reflux. After 1 hour, cool to ambient temperature and dilute with diethyl ether (250 mL) and stir to give a solid. Collect the solid by filtration, rinse with diethyl ether, and dry to give the title compound.

EXAMPLE 36

N-Methyl-N-(4-(4-(1-(allyl)-1H-benzimidazol-2-yl)[1,4]diazepan-1-yl)-2-(3,4-dichlorophenyl)butyl)-2-methoxy-5-(1H-tetrazol-1-yl)benzamide

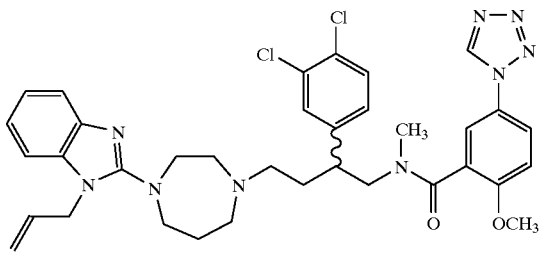

36.1 Synthesis N-methyl-N-(4-(4-(1-(allyl)-1H-benzimidazol-2-yl)[1,4]diazepan-1-yl)-2-(3,4-dichlorophenyl)butyl)-2-methoxy-5-(1H-tetrazol-1-yl)benzamide Prepare by the method of Example 1.7 using N-methyl-N-(2-(3,4-dichlorophenyl)-4-methanesulfonylbutyl)-2-methoxy-5-(1H-tetrazol-1-yl)benzamide and 4-(1-(allyl)-1H-benzimidazol-2-yl)[1,4]diazepane to give the title compound.

PREPARATION 21

Synthesis of 2-methoxy-5-(4H-triazol-4-yl)benzoyl chloride

According to the method of J. Chem. Soc. (C), 1664 (1967), combine methyl 2-methoxy-5-aminobenzoate (2.0 g, 11 mmol), N,N-dimethylformamide azine (1.56 g, 11 mmol), p-toluenesulfonic acid (190 mg) in toluene (25 mL). Fit the reaction vessel with a gas inlet such that the head space of the vessel is swept with argon and scrub the effluent through dilute aqueous hydrochloric acid solution. Heat to reflux. After 20 hours, concentrate the reaction mixture in vacuo to give a residue. Partition the residue between dichloromethane and a saturated aqueous sodium bicarbonate solution. Extract the aqueous layer twice with dichloromethane. Combine the organic layers, dry over MgSO$_4$, filter, and evaporate in vacuo to give a residue. Chromatograph the residue on silica gel eluting sequentially with 70% ethyl acetate/dichloromethane and then 5% methanol/dichloromethane to give a residue. Recrystallize the residue form ethyl acetate/hexane to give methyl 2-methoxy-5-(4H-triazol-4-yl)benzoate: mp; 191–195.5° C. Alternately, according to the method of *J. Med. Chem.*, 21, 1100 (1978), combine methyl 2-methoxy-5-aminobenzoate (1.8 g, 10 mmol), diformyl hydrazine (0.97 g, 11 mmol), and phosphorous pentoxide (1.84 g, 13 mmol). Heat to 160° C. After 1.5 hours, cool the reaction mixture and add a saturated aqueous solution of sodium bicarbonate. Extract three times with dichloromethane. Dry the combined organic layers over MgSO$_4$, filter, and evaporate in vacuo to give a residue. Chromatograph the residue on silica gel eluting sequentially with 40% ethyl acetate/dichloromethane and then 5% methanol/dichloromethane to give methyl 2-methoxy-5-(4H-triazol-4-yl)benzoate: mp; 179–182° C.

Combine methyl 2-methoxy-5-(4H-triazol-4-yl)benzoate (56 mmol) and methanol (200 mL) and water (50 mL). Add 1 M aqueous solution of sodium hydroxide (62.5 mL, 62.5 mmol). Heat to reflux. After 8 hour, concentrate in vacuo to remove most of the solvent. Adjust the pH to about 1 to 2 using a 1 M aqueous hydrochloric acid solution, extract with dichloromethane. Dry the organic layer over MgSO$_4$, filter, and evaporate in vacuo to give 2-methoxy-5-(4H-triazol-4-yl)benzoic acid.

Combine 2-methoxy-5-(4H-triazol-4-yl)benzoic acid (5 mmol) and dichloromethane (40 mL). Add dropwise oxalyl chloride (0.72 mL, 8.25 mmol) followed by dimethylformamide (3 drops). After 4 hours, evaporate in vacuo and dry to give the title compound.

EXAMPLE 37

N-Methyl-N-(4-(4-(1-(2-ethoxyethyl)-1H-benzimidazol-2-yl)[1,4]diazepan-1-yl)-2-(4-fluorophenyl)butyl)-2-methoxy-5-(4H-triazol-4-yl) benzamide 37.2 Synthesis of N-methyl-N-(2-(4-fluorophenyl)-4-(t-butyldimethylsilyloxy)butyl)-2-methoxy-5-(4H-triazol-4-yl)benzamide Prepare by the method of Example 1.4 using N-(2-(4-fluorophenyl)-4-(t-butyldimethylsilyloxy)butyl)-2-methoxy-5-(4H-triazol-4-yl)benzamide to give the title compound.

37.3 Synthesis of N-methyl-N-(2-(4-fluorophenyl)-4-hydroxybutyl)-2-methoxy-5-(4H-triazol-4-yl)benzamide Prepare by the method of Example 1.5 using N-methyl-N-(2-(4-fluorophenyl)-4-(t-butyldimethylsilyloxy)butyl)-2-methoxy-5-(4H-triazol-4-yl)benzamide to give the title compound.

37.4 Synthesis of N-methyl-N-(2-(4-fluorophenyl)-4-methanesulfonylbutyl)-2-methoxy-5-(4H-triazol-4-yl) benzamide Prepare by the method of Example 1.6 using N-methyl-N-(2-(4-fluorophenyl)-4-hydroxybutyl)-2-methoxy-5-(4H-triazol-4-yl)benzamide to give the title compound.

37.5 Synthesis of N-methyl-N-(4-(4-(1-(2-ethoxyethyl)-1H-benzimidazol-2-yl)[1,4]diazepan-1-yl)-2-(4-fluorophenyl)butyl)-2-methoxy-5-(4H-triazol-4-yl)benzamide Prepare by the method of Example 1.7 using N-methyl-N-(2-(4-fluorophenyl)-4-methanesulfonylbutyl)-2-methoxy-5-(4H-triazol-4-yl)benzamide and 4-(1-(2-ethoxyethyl)-1H-benzimidazol-2-yl)[1,4]diazepane hydriodic acid salt to give the title compound.

PREPARATION 21A

Synthesis of 2-methoxy-5-trifluoromethoxybenzoyl chloride

Combine 2-methoxy-5-trifluoromethoxybenzene (1.0 g, 5.2 mmol) and trifluoroacetic acid (200 mL). Add slowly portionwise hexamethylenetetraamine (26 g, 185.7 mmol). Heat at 60° C. After 24 hours, cool to ambient temperature and pour the reaction mixture into a 2 M aqueous solution of sulfuric acid (500 mL). Cool and extract ten times with diethyl ether. Dry the combined organic layers over Na$_2$SO$_4$, filter, and evaporate in vacuo to give a residue. Chromatograph the residue on silica gel eluting with 1/4 ethyl acetate/hexane to give 2-methoxy-5-trifluoromethoxybenzaldehyde.

According to the method of *Heterocycles*, 16, 2091 (1981), combine 2-methoxy-5-trifluoromethoxybenzaldehyde (0.58 g, 2.65 mmol) and

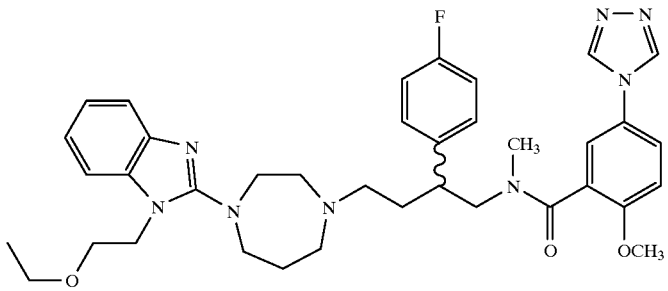

37.1 Synthesis of N-(2-(4-fluorophenyl)-4-(t-butyldimethylsilyloxy)butyl)-2-methoxy-5-(4H-triazol-4-yl)benzamide Prepare by the method of Example 33.1 using 2-(4-fluorophenyl)-4-(t-butyldimethylsilyloxy)butylamine and 2-methoxy-5-(4H-triazol-4-yl)benzoyl chloride to give the title compound.

2-methylbut-2-ene (37 mL) in t-butanol (16 mL). Add dropwise a solution of sodium dihydrogen phosphate hydrate (0.92 g) and sodium chlorite (0.42 g, 4.7 mmol) in water (10 mL). After 4 hours, adjust the pH of the reaction mixture to about 8 to 9 using a 1 M aqueous sodium hydroxide solution. Evaporate the reaction mixture in vacuo at about ambient temperature to remove most of the t-butanol. Add water (40 mL) and extract three times with hexane (10 mL). Adjust the pH of the aqueous layer to about 1 using a 1 M aqueous hydrochloric acid solution and extract five times with diethyl ether. Combine the organic layers, dry over $Na_2SO_4$, filter, and evaporate in vacuo to give a residue. Chromatograph the residue on silica gel eluting with 1/1 ethyl acetate/hexane containing 0.5% acetic acid to give 2-methoxy-5-trifluoromethoxybenzoic acid: $R_f$=0.34 (silica gel, 1/1 ethyl acetate/hexane containing 0.5% acetic acid).

Combine 2-methoxy-5-trifluoromethoxybenzoic acid (0.6 g, 2.53 mmol) and dichloromethane (10 mL). Cool in an ice bath. Add dropwise oxalyl chloride (0.64 mL, 5.0 mmol) followed by dimethylformamide (1 drop). Warm to ambient temperature. After 3 hours, evaporate in vacuo and dry to give the title compound.

EXAMPLE 38

N-Methyl-N-(4-(4-(1-(2-ethoxyethyl)-1H-benzimidazol-2-yl)[1,4]diazepan-1-yl)-2-(3,4-dichlorophenyl)butyl)-2-methoxy-5-trifluoromethoxybenzamide Prepare by the method of Example 1.6 using N-methyl-N-(2-(3,4-dichlorophenyl)-4-hydroxybutyl)-2-methoxy-5-trifluoromethoxybenzamide to give the title compound.

38.5 Synthesis of N-methyl-N-(4-(4-(1-(2-ethoxyethyl)-1H-benzimidazol-2-yl)[1,4]diazepan-1-yl)-2-(3,4-dichlorophenyl)butyl)-2-methoxy-5-trifluoromethoxybenzamide Prepare by the method of Example 1.7 using N-methyl-N-(2-(3,4-dichlorophenyl)-4-methanesulfonylbutyl)-2-methoxy-5-trifluoromethoxybenzamide and 4-(1-(2-ethoxyethyl)-1H-benzimidazol-2-yl)[1,4]diazepane hydriodic acid salt to give the title compound.

PREPARATION 22

Synthesis of 4-(1-(2-(2,2,2-trifluoroethoxy)ethyl)-1H-benzimidazol-2-yl)[1,4]diazepane hydriodic acid salt According to the procedure of Tet. Let. 35, 5997–6000 (1994), combine 4-(1-(2-hydroxyethyl)-1H-benzimidazol-

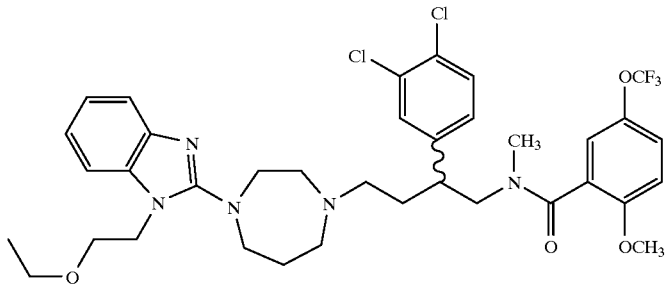

38.1 Synthesis of N-(2-(3,4-dichlorophenyl)-4-(t-butyldimethylsilyloxy)butyl)-2-methoxy-5-trifluoromethoxybenzamide Prepare by the method of Example 33.1 using 2-(3,4-dichlorophenyl)-4-(t-butyldimethylsilyloxy)butylamine (5.0 g, 16.8 mmol) and 2-methoxy-5-trifluoromethoxybenzoyl chloride to give the title compound.

38.2 Synthesis of N-methyl-N-(2-(3,4-dichlorophenyl)-4-(t-butyldimethylsilyloxy)butyl)-2-methoxy-5-trifluoromethoxybenzamide Prepare by the method of Example 1.4 using N-(2-(3,4-dichlorophenyl)-4-(t-butyldimethylsilyloxy)butyl)-2-methoxy-5-trifluoromethoxybenzamide to give the title compound.

38.3 Synthesis of N-methyl-N-(2-(3,4-dichlorophenyl)-4-hydroxybutyl)-2-methoxy-5-trifluoromethoxybenzamide Prepare by the method of Example 1.5 using N-methyl-N-(2-(3,4-dichlorophenyl)-4-(t-butyldimethylsilyloxy)butyl)-2-methoxy-5-trifluoromethoxybenzamide to give the title compound.

38.4 Synthesis of N-methyl-N-(2-(3,4-dichlorophenyl)-4-methanesulfonylbutyl)-2-methoxy-5-trifluoromethoxybenzamide 2-yl)[1,4]diazepane (10 mmol) and di-t-butyl dicarbonate (10 mmol) in tetrahydrofuran (100 mmol). After 18 hours, evaporate in vacuo to give 1-t-butoxycarbonyl-4-(1-(2-hydroxyethyl)-1H-benzimidazol-2-yl)[1,4]diazepane. Combine 1-t-butoxycarbonyl-4-(1-(2-hydroxyethyl)-1H-benzimidazol-2-yl)[1,4]diazepane (0.66 g, 1.84 mmol) and 1,1'-(azodicarbonyl)dipiperidine (0.50 g, 2 mmol) in toluene (20 mL). Add tributylphosphine (0.5 mL, 2 mmol). After 10 minutes, add 2,2,2-trifluoroethanol (0.7 mL, 10 mmol). Heat to 55° C. After 6 hours, cool to ambient temperature. After 18 hours, concentrate the reaction mixture to give a residue. Chromatograph the residue on silica gel eluting sequentially with hexane and then 30% ethyl acetate/hexane to give 1-t-butoxycarbonyl-4-(1-(2-(2,2,2-trifluoroethoxy)ethyl)-1H-benzimidazol-2-yl)[1,4]diazepane.

Combine 1-t-butoxycarbonyl-4-(1-(2-(2,2,2-trifluoroethoxy)ethyl)-1H-benzimidazol-2-yl)[1,4]diazepane (0.47 g, 1.1 mmol) and aqueous hydriodic acid (0.70 mL, 9,42 mmol) in methanol (10 mL). After 4 hours, evaporate to remove most of the methanol to give a residue. Combine the residue and diethyl ether (50 mL) and stir to give a solid. Collect the solid by filtration to give, after drying, the title compound: $R_f$=0.39 (silica gel, 10% methanol/dichloromethane/5% acetic acid).

EXAMPLE 38A

N-Methyl-N-(4-(4-(1-(2,2,2-trifluoroethoxy)ethyl)-1H-benzimidazol-2-yl)[1,4]diazepan-1-yl)-2-(4-fluorophenyl)butyl)-2-methoxy-5-(1H-tetrazol-1-yl)benzamide

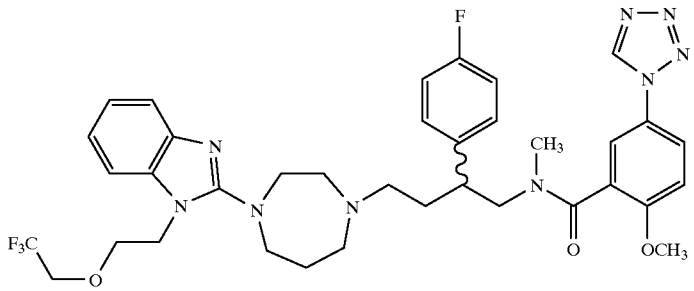

38A.1 Synthesis of N-methyl-N-(4-(4-(1-(2-(2,2,2-trifluoroethoxy)ethyl)-1H-benzimidazol-2-yl)[1,4]diazepan-1-yl)-2-(4-fluorophenyl)butyl)-2-methoxy-5-(1H-tetrazol-1-yl)benzamide Prepare by the method of Example 1.7 using N-methyl-N-(2-(4-fluorophenyl)-4-methanesulfonylbutyl)-2-methoxy-5-(1H-tetrazol-1-yl)benzamide and 4-(1-(2-(2,2,2-trifluoroethoxy)ethyl)-1H-benzimidazol-2-yl)[1,4]diazepane to give the title compound.

PREPARATION 23

Synthesis of 2-(chloromethyl)furan

Combine furfuryl alcohol (3.52 mL, 4.0 g, 40.8 mmol) and triethylamine (11.4 mL 81.5 mmol) in dichloromethane (70 mL). Cool in an ice bath. Add dropwise, methanesulfonyl chloride (43.73 mL, 61.2 mmol). After 3 hours, dilute the reaction mixture with dichloromethane (about 100 mL) and extract with water and then a saturated solution of sodium bicarbonate. Dry the organic layer over $Na_2SO_4$, filter and carefully evaporate in vacuo at 20° C. to remove the solvent to give a residue. Distill the residue at 25° C. at 0.2 mm Hg, collecting the distillate in a trap cooled in dry ice to give the title compound which is used immediately.

PREPARATION 24

Synthesis of 4-(1-(fur-2-ylmethyl)-1H-benzimidazol-2-yl)[1,4]diazepane hydriodic acid salt Combine 1-t-butoxycarbonyl-4-(1H-benzimidazol-2-yl)[1,4]diazepane (1.70 g, 5.4 mmol) in tetrahydrofuran (45 mL) and dimethylformamide (5 mL). Cool in an ice bath. Add sodium hydride (0.32 g, 60% in oil, 8.1 mmol) portionwise. After 15 minutes, warm to ambient temperature. After about 30 minutes, when the gas evolution ceases, add 2-(chloromethyl)furan (0.94 g, 8.1 mmol). After 18 hours, cool in an ice bath, add ice and then a saturated aqueous solution of ammonium chloride. Evaporate the reaction mixture to remove most of the tetrahydrofuran, dilute with ethyl acetate and extract with a saturate aqueous solution of sodium bicarbonate and then brine. Dry the organic layer over $Na_2SO_4$, filter, and evaporate in vacuo to give a residue. Chromatograph the residue on silica gel eluting with 50% ethyl acetate/hexane to give 1-t-butoxycarbonyl-4-(1-(fur-2-ylmethyl)-1H-benzimidazol-2-yl)[1,4]diazepane: $R_f=0.47$ (silica gel, ethyl acetate).

Combine 1-t-butoxycarbonyl-4-(1-(fur-2-ylmethyl)-1H-benzimidazol-2-yl)[1,4]diazepane (0.6 g, 1.5 mmol) and dioxane (10 mL). Add a solution of hydrochloric acid in dioxane (6.0 mL, 4 M, 24 mmol). After 40 minutes, add diethyl ether (50 mL) to give a solid. Collect the solid by filtration to give, after drying, 4-(1-(fur-2-ylmethyl)-1H-benzimidazol-2-yl)[1,4]diazepane hydrochloric acid salt: mp; 219–221° C.

Combine 4-(1-(fur-2-ylmethyl)-1H-benzimidazol-2-yl)[1,4]diazepane hydrochloric acid salt (0.57 g, 1.53 mmol) and dichloromethane (150 mL). Extract with a saturated aqueous solution of sodium bicarbonate, dry over $Na_2SO_4$, filter, and evaporate in vacuo to give a residue. Combine the residue and methanol (50 mL). Cool in an ice bath. Add aqueous hydriodic acid (0.194 g, 57%, 1.52 mmol). After 30 minutes, evaporate to remove most of the methanol and triturate with diethyl ether (150 mL) to give a solid. Decant the solvent, add diethyl ether (150 mL) and collect the solid by filtration to give, after drying, the title compound.

EXAMPLE 39

N-Methyl-N-(4-(4-(1-(2-(fur-2-ylmethyl)-1H-benzimidazol-2-yl)[1,4]diazepan-1-yl)-2-(4-fluorophenyl)butyl)-3,4,5-trimethoxybenzamide

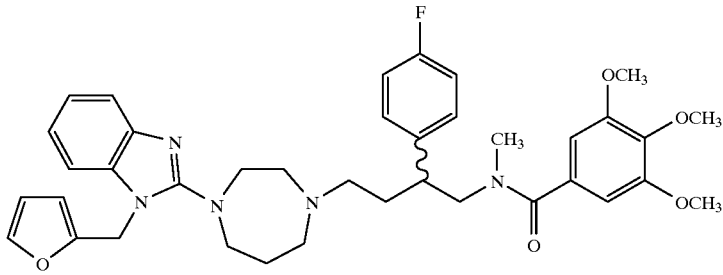

39.1 Synthesis of N-methyl-N-(4-(4-(1-(2-(fur-2-ylmethyl)-1H-benzimidazol-2-yl)[1,4]diazepan-1-yl)-2-(4-fluorophenyl)butyl)-3,4,5-trimethoxybenzamide Prepare by the method of Example 1.7 using N-methyl-N-(2-(4-fluorophenyl)-4-methanesulfonylbutyl)-3,4,5-trimethoxybenzamide and 4-(1-(2-(fur-2-ylmethyl)-1H-benzimidazol-2-yl)[1,4]diazepane hydriodic acid salt to give the title compound.

PREPARATION 25

Synthesis of 4-(1-(4,4,4-trifluorobutyl)-1H-benzimidazol-2-yl)[1,4]diazepane hydriodic acid salt Combine 1-t-butoxycarbonyl-4-(1H-benzimidazol-2-yl)[1,4]diazepane (1.5 g, 4.74 mmol) in tetrahydrofuran (45 mL) and dimethylformamide (5 mL). Cool in an ice bath. Add sodium hydride (0.23 g, 60% in oil, 5.7 mmol). Warm to ambient temperature. After about 90 minutes, when the gas evolution ceases, add 1-iodo-4,4,4-trifluorobutane (1.35 g, 5.7 mmol). After 18 hours, add ice and then a saturated aqueous solution of ammonium chloride. Evaporate the reaction mixture to remove most of the tetrahydrofuran, dilute with ethyl acetate and extract with water and then brine. Dry the organic layer over MgSO$_4$, filter, and evaporate in vacuo to give a residue. Chromatograph the residue on silica gel eluting with 60% ethyl acetate/hexane to give 1-t-butoxycarbonyl-4-(1-(4,4,4-trifluorobutyl)-1H-benzimidazol-2-yl)[1,4]diazepane: R$_f$=0.40 (silica gel, ethyl acetate).

Combine 1-t-butoxycarbonyl-4-(1-(4,4,4-trifluorobutyl)-1H-benzimidazol-2-yl)[1,4]diazepane (1.80 g, 4.22 mmol) and methanol (15 mL). Cool in an ice bath. Add aqueous hydriodic acid (3.8 g, 2.23 mL, 57%, 16.9 mmol) and warm to ambient temperature. After 30 minutes, add aqueous hydriodic acid (1.12 mL) and heat to 50° C. After 2 hours, cool to ambient temperature and evaporate to remove most of the methanol to give a residue. Combine the residue and methanol (10 mL). Add diethyl ether (200 mL) and stir to give a solid. Decant the solvent, add diethyl ether (200 mL) and stir, collect the solid by filtration to give, after drying, the title compound: mp; 206–208° C.

EXAMPLE 40

N-Methyl-N-(4-(4-(1-(4,4,4-trifluorobutyl)-1H-benzimidazol-2-yl)[1,4]diazepan-1-yl)-2-(4-fluorophenyl)butyl)-2-methoxy-5-(1H-tetrazol-1-yl)benzamide

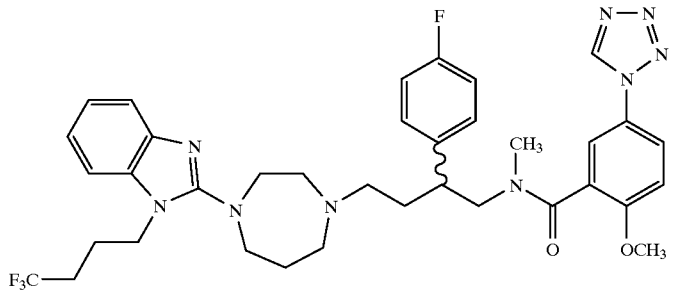

40.1 Synthesis of N-methyl-N-(4-(4-(1-(4,4,4-trifluorobutyl)-1H-benzimidazol-2-yl)[1,4]diazepan-1-yl)-2-(4-fluorophenyl)butyl)-2-methoxy-5-(1H-tetrazol-1-yl)benzamide Prepare by the method of Example 1.7 using N-methyl-N-(2-(4-fluorophenyl)-4-methanesulfonylbutyl)-2-methoxy-5-(1H-tetrazol-1-yl)benzamide and 4-(1-(4,4,4-trifluorobutyl)-1H-benzimidazol-2-yl)[1,4]diazepane hydriodic acid salt to give the title compound.

PREPARATION 26

Synthesis of 4-(1-pentyl-1H-benzimidazol-2-yl)[1,4]diazepane hydriodic acid salt Combine 1-t-butoxycarbonyl-4-(1H-benzimidazol-2-yl)[1,4]diazepane (0.8 g, 2.5 mmol) in dimethylformamide (10 mL). Add sodium hydride (0.13 g, 60% in oil, 3.25 mmol) portionwise. After about 30 minutes, when the gas evolution ceases, add pentyl bromide (0.34 mL, 2.74 mmol). Heat to 80° C. After 18 hours, cool the reaction mixture and dilute with dichloromethane (150 mL) and extract with brine. Dry the organic layer over MgSO$_4$, filter, and evaporate in vacuo to give 1-t-butoxycarbonyl-4-(1-pentyl-1H-benzimidazol-2-yl)[1,4]diazepane: R$_f$=0.87 (silica gel, 5% methanol/dichloromethane/0.05% concentrated aqueous ammonia). Combine 1-t-butoxycarbonyl-4-(1-pentyl-1H-benzimidazol-2-yl)[1,4]diazepane (0.7 g, 1.8 mmol) and ethanol (5 mL). Add aqueous hydriodic acid (5 mL, 57%). Heat to reflux. After 1 hour, cool to ambient temperature and dilute with diethyl ether (250 mL) and stir to give a solid. Collect the solid by filtration, rinse with diethyl ether, and dry to give the title compound.

EXAMPLE 41

N-Methyl-N-(4-(4-(1-pentyl-1H-benzimidazol-2-yl)[1,4]diazepan-1-yl)-2-(4-fluorophenyl)butyl)-2-methoxy-5-(1H-tetrazol-1-yl)benzamide

PREPARATION 27

Synthesis of 4-(1-(4-fluorobenzyl)-1H-benzimidazol-2-yl)[1,4]diazepane hydriodic acid salt Combine 1-t-butoxycarbonyl-4-(1H-benzimidazol-2-yl)[1,4]diazepane (0.82 g, 2.6 mmol) in dimethylformamide (20 mL). Add sodium hydride (0.15 g, 60% in oil, 3.75 mmol). After about 15 minutes, when the gas evolution ceases, add 4-fluorobenzyl bromide (0.35 mL, 2.81 mmol). Heat to 80° C. After 18 hours, cool the reaction mixture and dilute with ethyl acetate (100 mL) and extract five times with brine. Dry the organic layer over MgSO$_4$, filter, and evaporate in vacuo to give 1-t-butoxycarbonyl-4-(1-(4-fluorobenzyl)-1H-benzimidazol-2-yl)[1,4]diazepane: R$_f$=0.42 (silica gel, 50% ethyl acetate/hexane).

Combine 1-t-butoxycarbonyl-4-(1-(4-fluorobenzyl)-1H-benzimidazol-2-yl)[1,4]diazepane (1.12 g, 2.64 mmol) and ethanol (15 mL). Add aqueous hydriodic acid (5 mL, 57%). Heat to reflux. After 1 hour, cool to ambient temperature and dilute with diethyl ether (250 mL) and stir to give a solid. Collect the solid by filtration, rinse with diethyl ether, and dry to give the title compound: R$_f$=0.16 (silica gel, 10% methanol/dichloromethane/0.01% concentrated aqueous ammonia.

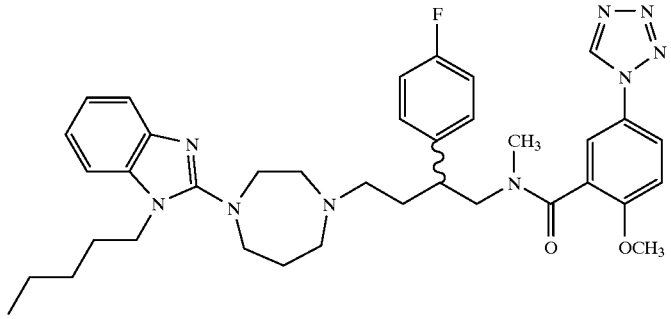

41.1 Synthesis of N-methyl-N-(4-(4-(1-pentyl-1H-benzimidazol-2-yl)[1,4]diazepan-1-yl)-2-(4-fluorophenyl)butyl)-2-methoxy-5-(1H-tetrazol-1-yl)benzamide Prepare by the method of Example 1.7 using N-methyl-N-(2-(4-fluorophenyl)-4-methanesulfonylbutyl)-2-methoxy-5-(1H-tetrazol-1-yl)benzamide and 4-(1-pentyl-1H-benzimidazol-2-yl)[1,4]diazepane hydriodic acid salt to give the title compound.

EXAMPLE 42

N-Methyl-N-(4-(4-(1-(4-fluorobenzyl)-1H-benzimidazol-2-yl)[1,4]diazepan-1-yl)-2-(4-fluorophenyl)butyl)-2-methoxy-5-(1H-tetrazol-1-yl)benzamide

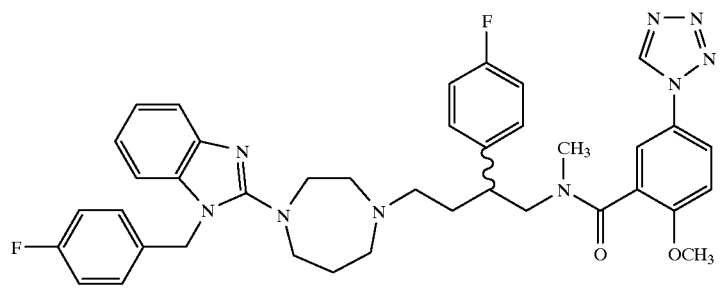

42.1 Synthesis of N-methyl-N-(4-(4-(1-(4-fluorobenzyl)-1H-benzimidazol-2-yl)[1,4]diazeian-1-yl)-2-(4-fluorophenyl)butyl)-2-methoxy-5-(1H-tetrazol-1-yl)benzamide Prepare by the method of Example 1.7 using N-methyl-N-(2-(4-fluorophenyl)-4-methanesulfonylbutyl)-2-methoxy-5-(1H-tetrazol-1-yl)benzamide and 4-(1-(4-fluorobenzyl)-1H-benzimidazol-2-yl)[1,4]diazepane hydriodic acid salt to give the title compound.

PREPARATION 28

Synthesis of (S)-N-methyl-N-(2-(4-fluorophenyl)-4-oxobutyl)-2-methoxy-5-(1H-tetrazol-1-yl)benzamide Combine (S)-4-benzyl-2-oxazolidinone (22.9 g, 129 mmol) and tetrahydrofuran (120 mL). Cool in a dry-ice acetone bath. Add dropwise a solution of n-butyl lithium (52 mL, 2.5 M, 130 mmol). After 15 minutes, slowly add a solution of 4-fluorophenylacetyl chloride (22.3 g, 129 mmol) in tetrahydrofuran (50 mL). Warm to ambient temperature. After 2 hours, quench the reaction mixture by the addition of a saturated aqueous sodium bicarbonate solution. Separate the layers and extract the aqueous layer with diethyl ether. Combine the organic layers, dry over $Na_2SO_4$, filter, and evaporate in vacuo to give a residue. Chromatograph the residue on silica gel eluting wit 15% ethyl acetate/hexane. Combine the product containing fractions, evaporate, and recrytallize from diethyl ether/hexane to give (S)-4-benzyl-3-(4-fluorophenyl)acetyl-2-oxazolidinone.

Alternately, combined (S)-benzyl-2-oxazolidinone(55.4 g, 313 mmol) and tetrahydrofuran (550 ml). Cool in a dry-ice acetone bath. Add n-butyl lithium (125 ml, 1 M in hexane, 312 mmol). After 30 minutes, add dropwise 4-fluorophenylacetyl chloride (56.7 g, 328 mmol). After 30 minutes, warm to ambient temperature, add a saturated aqueous sodium bicarbonate solution, and stir. After 45 minutes, separate the layers and extract the aqueous layer three times with ethyl acetate, combine the organic layers, extract with brine, dry over $MgSO_4$, filter, and evaporate in vacuo to give a viscous oil. Stir the viscous oil under vacuum to remove residual solvent and triturate with isopropanol to give a solid. Collect the solid by the filtration and rinse with isopropanol to give, after drying, (S)-4-benzyl-3-(4-fluorophenyl)acetyl-2-oxazolidinone.

Combine (S)-4-benzyl-3-(4-fluorophenyl)acetyl-2-oxazolidinone (14.28 g, 45.6 mmol) and tetrahydrofuran (150 mL). Cool in a dry-ice/acetone bath. Add dropwise a solution of sodium hexamethyldisilazide (50 mL, 1.0 M in tetrahydrofuran, 50 mmol). After 25 minutes, add allyl iodide (13 mL, 142.2 mmol) and then replace the bath with a dry-ice/carbon tetrachloride bath. After 1 hour, quench the reaction by the addition of a saturated aqueous ammonium chloride solution, extract with diethyl ether, and separate the layers. Dry the organic layer over $Na_2SO_4$, filter, and evaporate in vacuo to give a residue. Chromatograph the residue on silica gel eluting with 1/6 ethyl acetate/hexane. Combine the product containing fractions, evaporate, and recrytallize from chloroform/hexane to give (S)-4-benzyl-3-(2-(4-fluorophenyl)pent-4-enoyl)-2-oxazolidinone: mp; 103–104° C. $R_f$=0.57 (silica gel, 20% ethyl acetate/hexane).

Alternately, combine (S)-4-benzyl-3-(4-fluorophenyl)acetyl-2-oxazolidinone (43.08 g, 426 mmol) and tetrahydrofuran (450 ml). Cool in a dry-ice acetone bath. Add dropwise a solution of sodium hexamethyldisilazide (153.0 ml, 1 M in tetrahydrofuran, 137.5 mmol). After 40 minutes, add a solution of allyl iodide (39.0 ml, 426 mmol) and replace the bath with a dry-ice/carbon tetrachloride bath. After 1.5 hours, quench the reaction by the addition of a saturated aqueous solution of ammonium chloride, add diethyl ether (200 ml), and stir. After about 30 minutes, separate the layers and extract the aqueous layer twice with diethyl ether. Dry the combined organic layers over $MgSO_4$, filter, and evaporate in vacuo to give a residue. Dry the residue in a vacuum, dissolve in ethyl acetate (about 400 ml), and extract with a saturated aqueous sodium thiosulfate solution. Dry the organic layer over $MgSO_4$, filter, and evaporate in vacuo to give a residue. Chromatograph the residue on silica gel eluting with 13% ethyl acetate/hexane to give (S)-4-benzyl-3-(2-(4-fluorophenyl)pent-4-enoyl)-2-oxazolidinone.

Combine (S)-4-benzyl-3-(2-(4-fluorophenyl)pent-4-enoyl)-2-oxazolidinone (9.66 g, 27.34 mol), tetrahydrofuran (160 mL), and water (40 mL). Cool in an ice bath. Add lithium hydroxide hydrate (2.52 g, 60 mmol) and an aqueous solution of hydrogen peroxide (10 mL, 30% 116 mmol). After 3 hours, dilute the reaction mixture with an aqueous 1 M sodium hydroxide solution and extract twice with diethyl ether. Cool the aqueous layer in an ice bath, acidify with an aqueous concentrated hydrochloric acid solution (about 15 mL), and extract twice with dichloromethane. Extract the combined organic layers with a saturated aqueous sodium thiosulfate solution, dry over $MgSO_4$, filter, and evaporate in vacuo to give (S)-2-(4-fluorophenyl)pent-4-enoic acid.

Combine (S)-2-(4-fluorophenyl)pent-4-enoic acid (3.61 g, 18.6 mmol), dichloromethane (20 mL), and dimethylformamide (2 drops). Add oxalyl chloride (1.94 mL, 22.3 mmol). After 2 hours, evaporate in vacuo to give (S)-2-(4-fluorophenyl)pent-4-enoyl chloride. Combine with toluene (10 mL) and slowly add, with vigorous stirring, to a cooled (ice bath) aqueous solution of methylamine (4 mL, 40%). After 1 hour, partition the reaction mixture between water and dichloromethane. Separate the layers, extract the organic layer with a saturated aqueous sodium bicarbonate solution. Dry the organic over $MgSO_4$, filter, and evaporate in vacuo to give a residue. Triturate the residue with hexane to give a solid. Collect the solid by filtration and dry to give (S)-2-(4-fluorophenyl)pent-4-enoic acid, N-methyl amide: mp; 104–105° C. $R_f$=0.42 (silica gel, 50% ethyl acetate/hexane).

Combine (S)-2-(4-fluorophenyl)pent-4-enoic acid, N-methyl amide (3.1 g, 14.96 mmol) and tetrahydrofuran (35 mL). Cool in an ice bath, add a solution of lithium aluminum hydride (35 mL, 1.0 M in tetrahydrofuran, 35 mmol). After the addition is complete, heat the reaction mixture to reflux. After 2.5 hours, cool in an ice bath and carefully quench with water (1.3 mL), an aqueous 15% sodium hydroxide solution (1.3 mL), and then water (4 mL). Dilute the quenched reaction mixture with diethyl ether (75 mL), add $MgSO_4$, and stir. After 1 hour, filter through celite and rinse the solids with dichloromethane. Evaporate the filtrate in vacuo to give (S)-N-methyl-(2-(4-fluorophenyl)pent-4-enyl)amine: $R_f$=0.47 (silica gel, 18.5/1.5/0.2 dichloromethane/methanol/concentrated aqueous ammonia).

Combine (S)-N-methyl-2-(4-fluorophenyl)pent-4-enyl)amine (2.13 g, 11.0 mmol), acetone (100 mL, water (25 mL), and sodium bicarbonate (2.98 g, 35.5 mmol). Cool in an ice bath with vigorous stirring. Add portionwise, 2-methoxy-5-(1H-tetrazol-1-yl)benzoyl chloride (2.82 g, 11.7 mmol). After the addition is complete, warm to ambient temperature. After 1.5 hours, evaporate in vacuo to remove most of the acetone. Extract the evaporate reaction mixture with ethyl acetate. Extract the organic layer with a saturated aqueous sodium bicarbonate solution and then brine. Dry the organic layer over MgSO₄, filter, and evaporate in vacuo to give a residue. Chromatograph the residue on silica gel eluting with ethyl acetate to give (S)-N-methyl-N-(2-(4-fluorophenyl)pent-4-enyl)-2-methoxy-5-(1H-tetrazol-1-yl)benzamide: R$_f$=0.50 (silica gel, ethyl acetate).

Alternately, combine (S)-N-methyl-2-(4-fluorophenyl)pent-4-enyl)amine (2.25 g, 11 mmol), tetrahydrofuran (20 mL), water (5 mL), and sodium bicarbonate (1.23 g, 11.6 mmol). Add portionwise, 2-methoxy-5-(1H-tetrazol-1-yl) benzoyl chloride (2.78 g, 11.6 mmol). After 4 hours, evaporate in vacuo to remove most of the tetrahydrofuran. Separate the layers, extract the aqueous layer four times with dichloromethane. Combine the organic layers and extract with a saturated aqueous sodium bicarbonate solution. Dry the organic layer over Na₂SO₄, filter, and evaporate in vacuo to give a residue. Chromatograph the residue on silica gel eluting with ethyl acetate to give (S)-N-methyl-N-(2-(4-fluorophenyl)pent-4-enyl)-2-methoxy-5-(1H-tetrazol-1-yl)benzamide.

Combine (S)-N-methyl-N-(2-(4-fluorophenyl)pent-4-enyl)-2-methoxy-5-(1H-tetrazol-1-yl)benzamide (4.46 g, 11.3 mmol), acetone/t-butanol/water (2/1/1, 64 mL), and a solution of N-methylmorpholine N-oxide (3.0 mL, 50% in water, 14.5 mmol). Add a solution of osmium tetraoxide (3.0 mL, 4% in water, 0.5 mmol). After 3 hours, evaporate in vacuo to remove most of the acetone and partition the evaporated reaction mixture between dichloromethane and an aqueous 10% solution of sodium thiosulfate. Separate the layer, dry the organic layer over MgSO₄, filter, and evaporate in vacuo to give a residue. Combine the residue, tetrahydrofuran (80 mL), and water (20 mL). Add sodium meta-periodate (3.63 g). After 1.5 hours, filter the reaction mixture, rinse the solids with dichloromethane, and evaporate the filtrate to obtain a residue. Chromatograph the residue on silica gel eluting with ethyl acetate to give the title compound: R$_f$=0.22 (silica gel, ethyl acetate).

EXAMPLE 43

(S)-N-Methyl-N-(4-(4-(1-(4-fluorobenzyl)-1H-benzimidazol-2-yl)[1,4]diazepan-1-yl)-2-(4-fluorophenyl)butyl)-2-methoxy-5-(1H-tetrazol-1-yl)benzamide After 18 hours, cool in an ice bath and add a solution of sodium cyanoborohydride (3 ml, 1 M in tetrahydrofuran, 3.0 mmol). After the addition is complete warm to ambient temperature. After 2 hours, filter the reaction mixture and evaporate the filtrate in vacuo to give a residue. Partition the residue between dichloromethane and a saturated aqueous ammonium chloride solution. Separate the layers, dry the organic layer over MgSO₄, filter, and evaporate in vacuo to give a residue. Chromatograph the residue on silica gel eluting with 7.5% methanol/dichloromethane/1.0% concentrated ammonium hydroxide to give the title compound: R$_f$=0.33 (silica gel, 1.5/18.5/0.2 methanol/ dichloromethane/ concentrated ammonium hydroxide).

43.2 Synthesis of (S)-N-methyl-N-(4-(4-(1-(4-fluorobenzyl)-1H-benzimidazol-2-yl) [1,4]diazepan-1-yl)-2-(4-fluorophenyl)butyl)-2-methoxy-5-(1H-tetrazol-1-yl)benzamide hydrochloric acid salt Combine (S)-N-methyl-N-(4-(4-(1-(4-fluorobenzyl)-1H-benzimidazol-2-yl) [1,4]diazepan-1-yl)-2-(4-fluorophenyl)butyl)-2-methoxy-5-(1H-tetrazol-1-yl) benzamide (0.4 g, 0.57 mmol) in dichloromethane (4 mL). Add a solution of hydrochloric acid (0.3 mL, 4 M, 1.2 mmol) in dioxane. After 1.5 hours, evaporate the reaction mixture to give a residue. Triturate the residue with diethyl ether (100 mL) to give, after stirring, a solid. Collect the solid by filtration to give, after drying, the title compound.

PREPARATION 29

Synthesis of (S)-N-methyl-N-(2-phenyl-4-oxobutyl)-2-methoxy-5-(1H-tetrazol-1-yl) benzamide Combine (S)-4-benzyl-2-oxazolidinone (22.9 g, 129 mmol) and tetrahydrofuran (120 mL). Cool in a dry-ice acetone bath. Add dropwise a solution of n-butyl lithium (52 mL, 2.5 M, 130 mmol). After 15 minutes, slowly add a solution of phenylacetyl chloride (20 g, 129.4 mmol) in tetrahydrofuran (50 mL). After 20 minutes, warm to ambient temperature. After 2 hours, quench the reaction mixture by the addition of a saturated aqueous sodium bicarbonate solution. Separate the layers and extract the aqueous layer with diethyl ether. Combine the organic layers, dry over Na₂SO₄, filter, and evaporate in vacuo to give a residue.

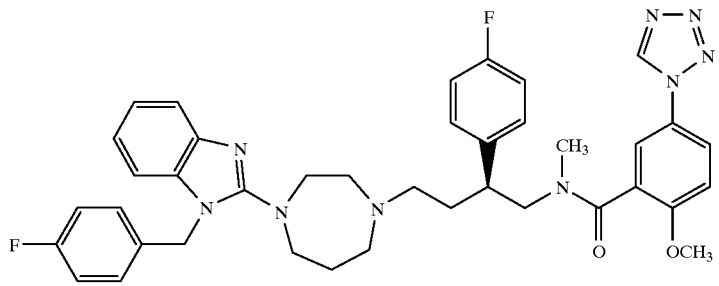

43.1 Synthesis of (S)-N-methyl-N-(4-(4-(1-(4-fluorobenzyl)-1H-benzimidazol-2-yl)[1,4]diazepan-1-yl)-2-(4-fluorophenyl)butyl)-2-methoxy-5-(1H-tetrazol-1-yl)benzamide Combine (S)-N-methyl-N-(2-(4-fluorophenyl)-4-oxobutyl)-2-methoxy-5-(1H-tetrazol-1-yl)benzamide (0.397 g, 1.0 mmol) and 4-(1-(4-fluorobenzyl)-1H-benzimidazol-2-yl)[1,4]diazepane hydriodic acid salt (0.58 g, 1.0 mmol) and 3A molecular sieves (about 0.5 g) in methanol (10 mL).

Chromatograph the residue on silica gel eluting with 15% ethyl acetate/hexane. Combine the product containing fractions, evaporate, and recrytallize from diethyl ether/ hexane to give (S)-4-benzyl-3-phenylacetyl-2-oxazolidinone.

Combine (S)-4-benzyl-3-phenylacetyl-2-oxazolidinone (14.13 g, 47.9 mmol) and tetrahydrofuran (150 mL). Cool in a dry-ice/acetone bath. Add dropwise a solution of sodium hexamethyldisilazide (52.6 mL, 1.0 M in tetrahydrofuran, 52.6 mmol). After 25 minutes, add allyl iodide (13.12 mL, 143.5 mmol) and then replace the bath with a dry-ice/carbon tetrachloride bath. After 1 hour, quench the reaction by the addition of a saturated aqueous ammonium chloride solution, extract with diethyl ether, and separate the layers. Dry the organic layer over $Na_2SO_4$, filter, and evaporate in vacuo to give a residue. Chromatograph the residue on silica gel eluting with 15% ethyl acetate/hexane. Combine the product containing fractions, evaporate, and recrytallize from chloroform/hexane to give (S)-4-benzyl-3-(2-phenylpent-4-enoyl)-2-oxazolidinone: $R_f$=0.40 (silica gel, 15% ethyl acetate/hexane).

Alternately, combine (S)-4-benzyl-3-phenylacetyl-2-oxazolidinone (8.0 g, 27 mmol) and tetrahydrofuran (50 mL). cool in a dry-ice/acetone bath. Add dropwise a solution of sodium hexamethyldisilazide (30 mL, 1.0 M in tetrahydrofuran, 30 mmol). After 30 minutes, add allyl iodide (9.1 g, 54 mmol) and then replace the bath with a dry-ice/carbon tetrachloride bath. After 1.5 hours, quench the reaction by the addition of a saturated aqueous sodium chloride solution, extract with diethyl ether, and separate the layers. Extract the aqueous layer three times with diethyl ether. Combine the organic layers, extract with an aqueous 1 M hydrochloric acid solution, a saturated aqueous sodium bicarbonate solution, dry the organic layer over $Na_2SO_4$, filter, and evaporate in vacuo to give a residue. Dissolve in ethyl acetate, extract with a saturated aqueous sodium thiosulfate solution, dry the over $Na_2SO_4$, filter, and evaporate in vacuo to give a residue. Chromatograph the residue on silica gel eluting with 10% ethyl acetate/hexane. Combine the product containing fractions, evaporate, and recrytallize from chloroform/hexane to give (S)-4-benzyl-3-(2-phenylpent-4-enoyl)-2-oxazolidinone.

Combine (S)-4-benzyl-3-(2-phenylpent-4-enoyl)-2-oxazolidinone (3.35 g, 10 mol), tetrahydrofuran (80 mL), and water (20 mL). Cool in an ice bath. Add lithium hydroxide hydrate (0.84 g, 20 mmol) and an aqueous solution of hydrogen peroxide (4 mL, 30%, 46.4 mmol). After 3 hours, concentrate the reaction mixture to about half volume, dilute the concentrated reaction mixture with an aqueous 1 M sodium hydroxide solution and extract twice with diethyl ether. Cool the aqueous layer in an ice bath, acidify with an aqueous 3 M hydrochloric acid solution, and extract twice with dichloromethane. Extract the combined organic layers with a saturated aqueous sodium thiosulfate solution, dry over $MgSO_4$, filter, and evaporate in vacuo to give (S)-2-phenylpent-4-enoic acid: $R_f$=0.48 (silica gel, 5% methanol/dichloromethane).

Combine (S)-2-phenylpent-4-enoic acid (1.53 g, 8.7 mmol), dichloromethane (10 mL), and dimethylformamide (1 drop). Add oxalyl chloride (1 mL, 11.46 mmol). After 2 hours, evaporate in vacuo to give (S)-2-phenylpent-4-enoyl chloride. Combine with toluene (10 mL) and add, with vigorous stirring, to a cooled (ice bath) aqueous solution of methylamine (2 mL, 40%). After 1 hour, partition the reaction mixture between water and dichloromethane. Separate the layers, dry the organic over $MgSO_4$, filter, and evaporate in vacuo to give a residue. Triturate the residue with hexane to give a solid. Collect the solid by filtration and dry to give (S)-2-phenylpent-4-enoic acid, N-methyl amide: mp; 97–99° C. $R_f$=0.53 (silica gel, 50% ethyl acetate/hexane).

Combine (S)-2-phenylpent-4-enoic acid, N-methyl amide (1.35 g, 7.13 mmol) and tetrahydrofuran (20 mL). Cool in an ice bath, add a solution of lithium aluminum hydride (17 mL, 1.0 M in tetrahydrofuran, 17 mmol). After the addition is complete, heat the reaction mixture to reflux. After 24 hours, cool in an ice bath and carefully quench with water (0.6 mL), an aqueous 15% sodium hydroxide solution (0.6 mL) and then water (2 mL). Dilute the quenched reaction mixture with diethyl ether (50 mL), add $MgSO_4$, and stir. After 2 hours, filter through celite and rinse the solids with dichloromethane. Dry the filtrate with $MgSO_4$, and evaporate in vacuo to give (S)-N-methyl-(2-phenylpent-4-enyl) amine: $R_f$=0.51 (silica gel, 18/2/0.2 dichloromethane/methanol/concentrated aqueous ammonia).

Combine (S)-N-methyl-(2-phenylpent-4-enyl)amine (1.93 g, 11.0 mmol), acetone/water (4/1, 125 mL), and sodium bicarbonate (3.0 g, 35.5 mmol). Cool in an ice bath with vigorous stirring. Add portionwise, 2-methoxy-5-(1H-tetrazol-1-yl) benzoyl chloride (2.86 g, 11.8 mmol). After the addition is complete, warm to ambient temperature. After 1.5 hours, evaporate in vacuo to remove most of the acetone. Extract the evaporated reaction mixture with ethyl acetate. Extract the organic layer with a saturated aqueous sodium bicarbonate solution and then brine. Dry the organic layer over $MgSO_4$, filter, and evaporate in vacuo to give a residue. Chromatograph the residue on silica gel eluting with ethyl acetate to give (S)-N-methyl-N-(2-phenylpent-4-enyl)-2-methoxy-5-(1H-tetrazol-1-yl) benzamide: $R_f$=0.35 (silica gel, ethyl acetate).

Combine (S)-N-methyl-N-(2-phenylpent-4-enyl)-2-methoxy-5-(1H-tetrazol-1-yl) benzamide (3.13 g, 8.3 mmol), acetone/t-butanol/water (2/1/1, 90 mL), and a solution of N-methylmorpholine N-oxide (2.06 mL, 50% in water, 9.95 mmol). Add a solution of osmium tetraoxide (2.56 mL, 4% in water, 0.5 mmol). After 18 hours, evaporate in vacuo to remove most of the acetone and extract the evaporated reaction mixture with dichloromethane. Extract the organic layer with an aqueous 10% solution of sodium thiosulfate. Dry the organic layer over $MgSO_4$, filter, and evaporate in vacuo to give a residue: $R_f$=0.22 (silica gel, 7% methanol/dichloromethane/0.1% concentrated ammonium hydroxide). Combine the residue (3.6 g, 8.3 mmol) and tetrahydrofuran/water (90 mL, 4/1). Add sodium metaperiodate (2.13 g, 9.95 mmol). After 1 hour, filter the reaction mixture, rinse the solids with tetrahydrofuran, and evaporate the filtrate to obtain a residue. Dilute the residue with ethyl acetate (150 mL), extract with brine, dry over $MgSO_4$, filter, and evaporate in vacuo to give a residue. Chromatograph the residue on silica gel eluting with 5% methanol/dichloromethane/0.1% concentrated ammonium hydroxide to give the title compound: $R_f$=0.33 (silica gel, 7% methanol/dichloromethane/0.1% concentrated ammonium hydroxide). $[\alpha]_D^{20}$=−13.7° (c=0.59, chloroform).

PREPARATION 30

Synthesis of 4-(1-(4,4,4-trifluoroethyl)-1H-benzimidazol-2-yl)[1,4]diazepane hydriodic acid salt Prepare by the method of Preparation 25 using 1-t-butoxycarbonyl-4-(1H-benzimidazol-2-yl) [1,4]diazepane and 1-iodo-2,2,2-trifluoroethane to give the title compound: mp; >225° C. Elemental Analysis calculated for $C_{14}H_{17}F_3N_4$. 2HI: C, 30.35; H, 3.46; N, 10.11. Found: C, 30.46; H, 3.33; N, 9.79.

EXAMPLE 44

(S)-N-Methyl-N-(4-(4-(1-(2,2,2-trifluoroethyl)-1H-benzimidazol-2-yl)[1,4]diazepan-1-yl)-2-phenylbutyl)-2-methoxy-5-(1H-tetrazol-1-yl)benzamide

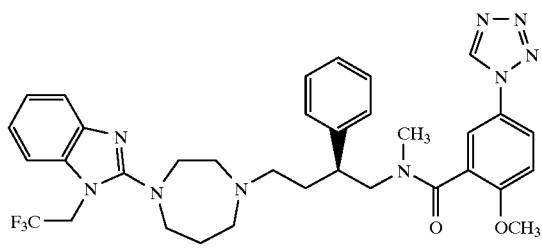

44.1 Synthesis of (S)-N-methyl-N-(4-(4-(1-(2,2,2-trifluoroethyl)-1H-benzimidazol-2-yl)[1,4]diazepan-1-yl)-2-phenylbutyl)-2-methoxy-5-(1H-tetrazol-1-yl)benzamide Prepare by the method of Example 43.1 using (S)-N-methyl-N-(2-phenyl-4-oxobutyl)-2-methoxy-5-(1H-tetrazol 1-yl)benzamide and 4-(1-(2,2,2-trifluoroethyl)-1H-benzimidazol-2-yl)[1,4]diazepane hydriodic acid salt to give the title compound.

44.2 Synthesis of (S)-N-methyl-N-(4-(4-(1-(2,2,2-trifluoroethyl)-1H-benzimidazol-2-yl)[1,4]diazepan-1-yl)-2-phenylbutyl)-2-methoxy-5-(1H-tetrazol-1-yl)benzamide hydrochloric acid salt.

Prepare by the method of Example 43.2 (S)-N-methyl-N-(4-(4-(1-(2,2,2-trifluoroethyl)-1H-benzimidazol-2-yl)]1,4]diazepan-1-yl)-2-phenylbutyl)-2-methoxy-5-(1H-tetrazol-1-yl)benzamide to give the title compound.

PREPARATION 31

Synthesis of (S)-N-methyl-N-(2-phenyl-4-oxobutyl)-2-methoxy-5-(4H-triazol-4-yl)benzamide Combine N-methyl-(2-phenylpent-4-enyl)amine (1.00 g, 5.7 mmol), acetone (50 mL), water (20 mL), and sodium bicarbonate (0.3 g, 2.85 mmol). Add portionwise, a solution of 2-methoxy-5-(4H-triazol-4-yl)benzoyl chloride (1.4 g, 6.3 mmol) in acetone (50 mL). After 10 hours, dilute the reaction mixture with a saturated aqueous sodium bicarbonate solution and evaporate in vacuo to remove most of the acetone. Extract five times with dichloromethane. Dry the combined organic layers over Na$_2$SO$_4$, filter, and evaporate in vacuo to give a residue. Chromatograph the residue on silica gel eluting with 5% methanol/dichloromethane to give (S)-N-methyl-N-(2-phenylpent-4-enyl)-2-methoxy-5-(4H-triazol-4-yl)benzamide: R$_f$=0.25 (silica gel, 5% methanol/dichloromethane).

Combine (S)-N-methyl-N-(2-phenylpent-4-enyl)-2-methoxy-5-(4H-triazol-4-yl)benzamide (1.03 g, 2.74 mmol), acetone (15 mL, t-butanol (7.5 mL), water (7.5 mL), and a solution of N-methylmorpholine N-oxide (0.74 mL, 50% in water, 3.56 mmol). Add a solution of osmium tetraoxide (1.0 mL, 4% in water). After 36 hours, evaporate in vacuo to remove most of the acetone and extract the evaporated reaction mixture with dichloromethane. Extract the organic layer with an aqueous 10% solution of sodium thiosulfate. Extract the aqueous layer five times with dichloromethane. Dry the combined organic layers over Na$_2$SO$_4$, filter, and evaporate in vacuo to give a residue. Combine the residue and tetrahydrofuran/water (20 mL, 4/1). Add sodium meta-periodate (0.7 g, 3.29 mmol). After 25 minutes, filter the reaction mixture, rinse the solids with tetrahydrofuran, and evaporate the filtrate to obtain a residue. Dilute the residue with dichloromethane (100 mL), extract with water, dry over MgSO$_4$, filter, and evaporate in vacuo to give a residue. Chromatograph the residue on silica gel eluting with 10% methanol/dichloromethane to give the title compound.

EXAMPLE 45

(S)-N-Methyl-N-(4-(4-(1-(4-fluorobenzyl)-1H-benzimidazol-2-yl)[1,4]diazepan-1-yl)-2-phenylbutyl)-2-methoxy-5-(4H-triazol-4-yl)benzamide

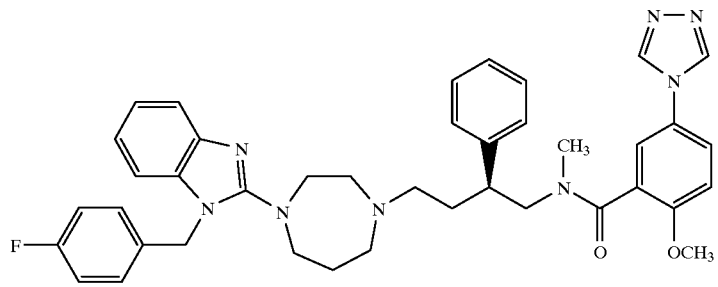

45.1 Synthesis of (S)-N-methyl-N-(4-(4-(1-(4-fluorobenzyl)-1H-benzimidazol-2-yl)[1,4]diazepan-1-yl)-2-phenylbutyl)-2-methoxy-5-(4H-triazol-4-yl)benzamide.

Prepare by the method of Example 43.1 using (S)-N-methyl-N-(2-phenyl-4-oxobutyl)-2-methoxy-5-(4H-triazol-4-yl)benzamide and 4-(1-(4-fluorobenzyl)-1H-benzimidazol-2-yl)[1,4]diazepane hydriodic acid salt to give the title compound.

45.2 Synthesis of (S)-N-methyl-N-(4-(4-(1-(4-fluorobenzyl)-1H-benzimidazol-2-yl) [1,4]diazepan-1-yl)-2-phenylbutyl)-2-methoxy-5-(4H-triazol-4-yl)benzamide hydrochloric acid salt.

Prepare by the method of Example 43.2 using (S)-N-methyl-N-(4-(4-(1-(4-fluorobenzyl)-1H-benzimidazol-2-yl) [1,4]diazepan-1-yl)-2-phenylbutyl)-2-methoxy-5-(4H-triazol-4-yl)benzamide to give the title compound.

PREPARATION 32

Synthesis of 4-(1-(2-methoxyethyl)-1H-benzimidazol-2-yl) [1,4]diazepane hydriodic acid salt Combine 1-(t-butoxycarbonyl)-4-(1H-benzimidazol-2-yl) [1,4]diazepane (2.03 g, 6.41 mmol) and dimethylformamide (50 mL). Cool in an ice-bath. Add sodium hydride (0.28 g, 60% in oil, 7.0 mmol). After 20 minutes, add 2-chloroethyl methyl ether (0.7 mL, 7.66 mmol). Heat to 85° C. After 18 hours, cool to ambient temperature and dilute with dichloromethane, and extract with water, a saturated aqueous sodium bicarbonate solution, and then brine. Dry the organic layer over MgSO₄, filter, and evaporate in vacuo to give a residue. Chromatograph the residue on silica gel eluting with dichloromethane/methanol/concentrated ammonium hydroxide 95/5/0.05 to give 1-(t-butoxycarbonyl)-4-(1-(2-methoxyethyl)-1H-benzimidazol-2-yl)[1,4]diazepane.

Combine 1-(t-butoxycarbonyl)-4-(1-(2-methoxyethyl)-1H-benzimidazol-2-yl) [1,4]diazepane (1.69 g, 5.23 mmol), aqueous hydriodic acid (10 mL, 57%), and ethanol (20 mL). Heat to reflux. After 1 hour, cool to ambient temperature and pour the reaction mixture into diethyl ether (350 mL) and stir to give a solid. After 1 hour, collect the solid and dry in vacuo to give the title compound.

EXAMPLE 46

(S)-N-Methyl-N-(4-(4-(1-(2-methoxyethyl)-1H-benzimidazol-2-yl) [1,4]diazepan-1-yl)-2-(4-fluorophenyl)butyl)-2-methoxy-5-(1H-tetrazol-1-yl) benzamide

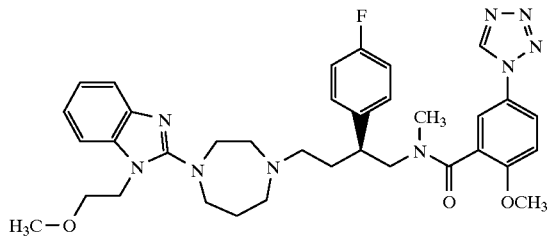

46.1 Synthesis of (S)-N-methyl-N-(4-(4-(1-(2-methoxyethyl)-1H-benzimidazol-2-yl)[1,4]diazepan-1-yl)-2-(4-fluorophenyl)butyl)-2-methoxy-5-(1H-tetrazol-1-yl) benzamide.

Prepare by the method of Example 43.1 (S)-N-methyl-N-(2-(4-fluorophenyl)-4-oxobutyl)-2-methoxy-5-(1H-tetrazol-1-yl)benzamide and 4-(1-(2-methoxyethyl)-1H-benzimidazol-2-yl)[1,4]diazepane hydriodic acid salt to give the title compound.

PREPARATION 33

Synthesis of 4-(1-(but-2-en-1-yl)-1H-benzimidazol-2-yl)[1,4]diazepane hydriodic acid salt Prepare by the method of Preparation 32 using 1-(t-butoxycarbonyl)-4-(1H-benzimidazol-2-yl)[1,4]diazepane (0.85 g, 2.69 mmol) and crotyl bromide (technical, 0.38 mL, 3.69 mmol) to give the title compound.

EXAMPLE 47

(S)-N-Methyl-N-(4-(4-(1-(but-2-en-1-yl)-1H-benzimidazol-2-yl)[14,4]diazepan-1-yl)-2-(4-fluorophenyl)butyl)-2-methoxy-5-(1H-tetrazol-1-yl) benzamide

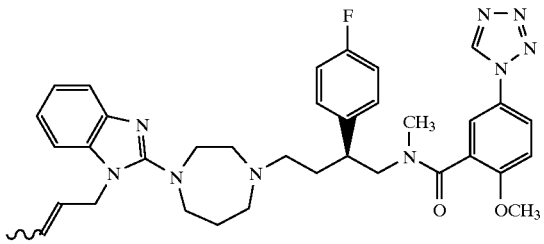

47.1 Synthesis of (S)-N-methyl-N-(4-(4-1-(but-2-en-1-yl)-1H-benzimidazol-2-yl)[1,4]diazepan-1-yl)-2-(4-fluorophenyl)butyl)-2-methoxy-5-(1H-tetrazol-1-yl) benzamide.

Prepare by the method of Example 43.1 (S)-N-methyl-N-(2-(4-fluorophenyl)-4-oxobutyl)-2-methoxy-5-(1H-tetrazol-1-yl)benzamide and 4-(1-(but-2-en-1-yl)-1H-benzimidazol-2-yl)[1,4]diazepane hydriodic acid salt to give the title compound.

PREPARATION 34

Synthesis of 4-1-(2-(isopropoxy)ethyl)-1H-benzimidazol-2-yl)[1,4]diazepane hydriodic acid salt Combine 2-isopropoxyethanol (1.0 g, 9.6 mmol), N,N-diisopropylethylamine (2.73 g, 21.12 mmol), and dichloromethane (20 mL). Cool in an ice bath. Add dropwise methanesulfonyl chloride (1.43 g, 9.6 mmol). After 2 hours, dilute the reaction mixture with dichloromethane and extract with 1M hydrochloric acid solution, a saturated solution of sodium bicarbonate, and then brine. Dry the organic layer over Na₂SO₄, filter, and evaporate in vacuo to give a residue. Distill the residue to give 2-(isopropoxy)ethyl mesylate: bp; 84° C. at 0.1 mm Hg.

Alternately, combine 2-isopropoxyethanol (5.0 g, 48 mmol) and dichloromethane (50 mL). Cool in an ice bath. Add triethylamine (10.7 g, 105 mmol). Add dropwise methanesulfonyl chloride (1.43 g, 9.6 mmol). After 2 hours, dilute the reaction mixture with dichloromethane and extract with 1 M hydrochloric acid solution, a saturated aqueous solution of sodium bicarbonate, and then brine. Dry the organic layer over Na₂SO₄, filter, and evaporate in vacuo to give a residue. Distill the residue at reduced pressure to give 2-(isopropoxy)ethyl mesylate.

Combine 1-(t-butoxycarbonyl)-4-(1H-benzimidazol-2-yl) [1,4]diazepane (0.54 g, 1.71 mmol) and sodium hydride (0.87 g, 3.48 mmol) in dimethylformamide (10 mL). After 30 minutes, add 2-(isopropoxy)ethyl mesylate (0.51 g, 5.5 mmol). Heat to 80° C. After 2 hours, cool the reaction mixture to ambient temperature and partition between dichloromethane and a saturated aqueous sodium bicarbonate solution. Separate the layers and extract the organic layer with brine. Dry the organic layer over MgSO₄, filter, and evaporate in vacuo to give 1-(t-butoxycarbonyl)-4-(1-(2-(isopropoxy)ethyl)-1H-benzimidazol-2-yl)[1,4]diazepane.

Combine 1-(t-butoxycarbonyl)-4-(1-(2-(isopropoxy)ethyl)-1H-benzimidazol-2-yl)[1,4]diazepane (0.63 g, 1.57 mmol), aqueous hydriodic acid (5 mL, 57%), and ethanol (10 mL). Heat to reflux. After 1 hour, cool to ambient temperature and pour the reaction mixture into diethyl ether (350 mL) and stir to give a solid. After 1 hour, collect the solid by filtration, rinse with diethyl ether, and dry in vacuo to give the title compound.

EXAMPLE 48

(S)-N-Methyl-N-(4-(4-1-(2-(isopropoxy)ethyl)-1H-benzimidazol-2-yl)[1,4]diazepan-1-yl)-2-(4-fluorophenyl)butyl)-2-methoxy-5-(1H-tetrazol-1-yl) benzamide

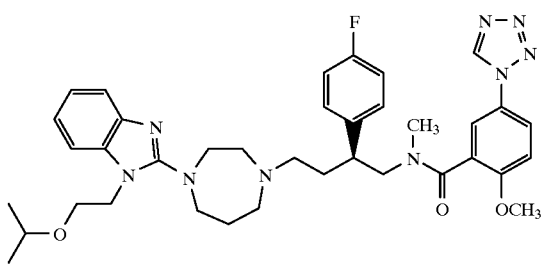

48.1 Synthesis of (S)-N-methyl-N-(4-(4-(1-(2-(isopropoxy) ethyl)-1H-benzimidazol-2-yl)[1,4]diazepan-1-yl)-2-(4-fluorophenyl)butyl)-2-methoxy-5-(1H-tetrazol-1-yl) benzamide Prepare by the method of Example 43.1 (S)-N-methyl-N-(2-(4-fluorophenyl)-4-oxobutyl)-2-methoxy-5-(1H-tetrazol-1-yl)benzamide and 4-(1-(2-(isopropoxy)ethyl)-1H-benzimidazol-2-yl)[1,4]diazepane hydriodic acid salt to give the title compound.

PREPARATION 35

Synthesis of 4-(1-(2-(t-butoxy)ethyl)-1H-benzimidazol-2-yl)[1,4]diazepan

Combine 2-t-butoxyethanol (3.37 g, 28.5 mmol), triethylamine (6 mL, 43 mmol), and dichloromethane (150 mL). Cool in an ice bath. Add dropwise methanesulfonyl chloride (2.9 mL, 37.5 mmol). After 3 days, dilute the reaction mixture with dichloromethane and extract with a saturated solution of sodium bicarbonate and then brine. Dry the organic layer over $Na_2SO_4$, filter, and evaporate in vacuo to give 2-(t-butoxy)ethyl mesylate: $R_f$=0.75 (silica gel, 50% ethyl acetate/hexane).

Combine 1-(t-butoxycarbonyl)-4-(1H-benzimidazol-2-yl) [1,4]diazepane (0.56 g, 1.77 mmol), and sodium hydride (0.088 g, 60% in oil, 2.20 mmol) in dimethylformamide (10 mL). Add 2-(t-butoxy)ethyl mesylate (0.40 g, 2.04 mmol). Heat to 80° C. After 2 hours, cool to ambient temperature and partition the reaction mixture between dichloromethane and a saturated aqueous sodium bicarbonate solution. Separate the layers and extract the organic layer with brine. Dry the organic layer over $MgSO_4$, filter, and evaporate in vacuo to give 1-(t-butoxycarbonyl)-4-(1-(2-t-butoxy)ethyl)-1H-benzimidazol-2-yl)[1,4]diazepane.

Combine 1-(t-butoxycarbonyl)-4-(1-(2-t-butoxy)ethyl)-1H-benzimidazol-2-yl)[1,4]diazepane (0.89 g, 2.14 mmol), potassium hydroxide (2.46 g, 43.84 mmol), and hydrazine hydrate (2.2. mL, 45.35 mmol) in ethylene glycol (25 mL). Heat to 140° C. After 16 hours, heat to 170° C. After 4 hours, cool to ambient temperature and partition the reaction mixture between dichloromethane and a saturated aqueous sodium bicarbonate solution. Separate the layers and extract the organic layer with brine. Dry the organic layer over $MgSO_4$, filter, and evaporate in vacuo to give the title compound.

EXAMPLE 49

(S)-N-Methyl-N-(4-(4-1-(2-(t-butoxy)ethyl)-1H-benzimidazol-2-yl)[1,4]diazepan-1-yl)-2-(4-fluorophenyl)butyl)-2-methoxy-5-(1H-tetrazol-1-yl) benzamide

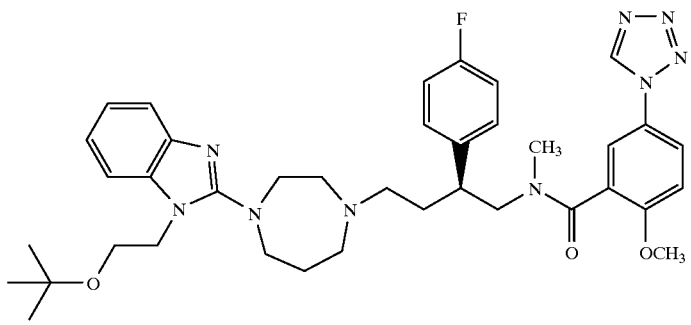

49.1 Synthesis of (S)-N-methyl-N-(4-(4-1-(2-(t-butoxy) ethyl)-1 H-benzimidazol-2-yl)[1,4]diazepan-1-yl)-2-(4-fluorophenyl)butyl)-2-methoxy-5-(1H-tetrazol-1-yl) benzamide Prepare by the method of Example 43.1 (S)-N-methyl-N-(2-(4-fluorophenyl)-4-oxobutyl)-2-methoxy-5-(1H-tetrazol-1-yl)benzamide and 4-(1-(2-(t-butoxy)ethyl)-1H-benzimidazol-2-yl)[1,4]diazepane hydriodic acid salt to give the title compound.

PREPARATION 36

Synthesis of 4-1-(2-(trifluoromethoxy)ethyl)-1H-benzimidazol-2-yl)[1,4]diaze-ane hydriodic acid salt According to the procedure of Syn. Comm., 22(17), 2459–2477 (1992), combine 2-benzyloxyethanol (15.21 g, 100 mmol) and tetrahydrofuran. Cool in an ice bath. Add sodium hydride (3.6 g, 150 mmol) and imidazole (0.68 g, 10 mmol) After 45 minutes, warm to ambient temperature and add carbon disulfide (15.64 mL, 260 mmol) After 10 minutes add methyl iodide (12.45 mL,. 200 mmol) After 20 minutes concentrate in vacuo to give a residue. Chromatograph the residue on silica gel eluting with hexane to give O-(2-benxyloxyethyl)-S-methyl dithiocarbonate.

According to the procedure of *Tet Lets.*, 33(29), 4173–4176 (1992), combine 1,3-dibromo-5,5-hydantoin (17.16 g, 60 mmol) and dichloromethane (100 mL). Cool in a dry-ice/acetone bath. Add a solution of O-(2-benxyloxyethyl)-S-methyl dithiocarbonate (4.8 g, 20 mmol) in dichloromethane (20 mL). Add pyridinium poly(hydrogen fluoride) (40 mL). After 3 hours, warm to about 0° C. After 0.5 hours, slowly pour the reaction mixture into an ice-cooled buffered solution saturated aqueous sodium bicarbonate and aqueous saturated sodium bisulfate and 1M aqueous sodium hydroxide (pH about 10). Extract three times with ethyl acetate. Combine the organic layers, dry over MgSO₄, filter, and evaporate in vacuo to give 2-(4-bromobenzyloxy)ethyl trifluoromethyl ether.

Combine 1-(t-butoxycarbonyl)-4-(1-(2-(trifluoromethoxy)ethyl)-1 H-benzimidazol-2-yl)[1,4]diazepane (0.18 g, 0.42 mmol) and methanol (5 mL). Add hydriodic acid (2 mL, 57%). After 4 hours, evaporate in vacuo to give the title compound.

EXAMPLE 50

(S)-N-Methyl-N-(4-(4-(1-(2-(trifluoromethoxy)ethyl)-1H-benzimidazol-2-yl)[1,4]diazeyan-1-yl)-2-(4-fluorophenyl)butyl)-2-methoxy-5-(1H-tetrazol-1-yl)benzamide

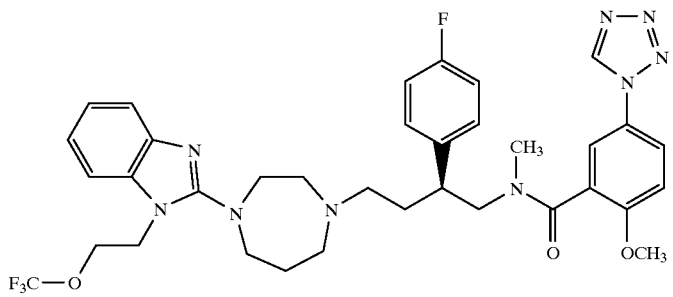

Combine 2-(4-bromobenzyloxy)ethyl trifluoromethyl ether (2.4 g, 8.1 mmol), thioanisole (28.5 mL, 243 mmol), and trifluoroacetic acid (30 mL). After 24 hours, add potassium bicarbonate to neutralize. Add MgSO₄ and chloroform (30 mL). Filter and distill through a short path distillation apparatus to give 2-(trifluoroacetoxy)ethyl trifluoromethyl ether containing chloroform which can be used without further purification.

Combine 2-(trifluoroacetoxy)ethyl trifluoromethyl ether as obtained above (containing chloroform), an aqueous solution of sodium hydroxide (405 by weight, 1 mL), and tetrahydrofuran (1 mL). After 30 minutes, filter to give a solution of 2-hydroxyethy trifluoromethyl ether. Add add molecular sieves to the filtrate. After 30 minutes, filter the above solution of 2-hydroxyethy trifluoromethyl ether to remove the molecular sieves. Cool the filtered solution in an ice-bath. Add N,N-diisopropylethylamine (1.4 mL) and methanesulfonyl chloride (0.63 mL, 8.1 mmol). After 4 hours, filter the reaction mixture and concentrate in vacuo to give a residue. Chromatograph the residue on silica gel eluting sequentially with hexane and then 20% ethyl acetate/hexane to give 2-(methanesulfonyloxy)ethyl trifluoromethoxy ether: $R_f$=0.21 (silica gel, 20% ethyl acetate/hexane).

Combine 1-(t-butoxycarbonyl)-4-(1H-benzimidazol-2-yl)[1,4]diazepane (0.31 g, 1 mmol) and dimethylformamide (8 mL). Cool in an ice-bath. Add sodium hydride (0.024 g, 1 mmol). After 2 hours, add 2-(methanesulfonyloxy)ethyl trifluoromethoxy ether (0.31 g, 1.5 mmol) and sodium iodide (0.14 g, 1 mmol). Heat to 80° C. After 6 hours, cool to ambient temperature. After 56 hours dilute the reaction mixture with ethyl acetate and extract brine. Dry the organic layer over MgSO₄, filter, and evaporate in vacuo to give a residue. Chromatograph the residue on silica gel eluting sequentially with hexane, 30% ethyl acetate/hexane and then 50% ethyl acetate/hexane to give 1-(t-butoxycarbonyl)-4-(1-(2-(trifluoromethoxy)ethyl)-1H-benzimidazol-2-yl)[1,4] diazepane; $R_f$=0.24 (silica gel, 50% ethyl acetate/hexane).

50.1 Synthesis of (S)-N-methyl-N-(4-(4-1-(2-(trifluoromethoxy)ethyl)-1H-benzimidazol-2-yl)[1,4]diazepan-1-yl)-2-(4-fluorophenyl)butyl)-2-methoxy-5-(1H-tetrazol-1-yl)benzamide Prepare by the method of Example 43.1 (S)-N-methyl-N-(2-(4-fluorophenyl)-4-oxobutyl)-2-methoxy-5-(1H-tetrazol-1-yl)benzamide and 4-(1-(2-(trifluoromethoxy)ethyl)-1H-benzimidazol-2-yl)[1,4]diazepane hydriodic acid salt to give the title compound.

PREPARATION 37

Synthesis of 2-methoxy-5-(5-trifluoromethyl-1H-tetrazol-1-yl)benzoic acid

Combine methyl 2-methoxy-5-aminobenzoate (1.8 g, 10 mmol) and pyridine (0.88 mL, 11 mmol) in tetrahydrofuran (10 mL). Cool in an ice bath. Add trifluoroacetic anhydride (1.56 mL, 11 mmol). Warm to ambient temperature. After 2 hours, add water and dilute the reaction mixture with ethyl acetate. Separate the organic layer, extract with brine, dry over MgSO₄, filter, and evaporate in vacuo to give methyl 2-methoxy-5-trifluoroacetylamidobenzoate. Combine methyl 2-methoxy-5-trifluoroacetylamidobenzoate (3.1 g, 15 mmol), triphenylphosphine (5.2 g, 20 mmol) and carbon tetrachloride (30 mL) in tetrahydrofuran (30 mL). Heat to reflux. After 18 hours, add carbon tetrachloride (100 mL) and continue to heat at reflux. After 18 hours, evaporate in vacuo to give a residue. Chromatograph the residue on a short column of silica gel eluting with 30% ethyl acetate/hexane to give methyl 2-methoxy-5-(2-trifluoromethyl-2-chloroiminobenzoate.

Combine methyl 2-methoxy-5-(2-trifluoromethyl-2-chloroiminobenzoate (3.4 g, 12 mmol) and sodium azide (3.12 g, 48 mmol) in glacial acetic acid (60 mL). Heat to 70° C. After 3 hours, cool the reaction mixture in an ice bath, add water (800 mL), and stir to give a solid. After 1 hour, collect the solid by filtration and dry to give methyl 2-methoxy-5-(5-trifluoromethyl-1H-tetrazol-1-yl)benzoate: $R_f$=0.58 (silica gel, 30% ethyl acetate/toluene).

Combine methyl 2-methoxy-5-(5-trifluoromethyl-1H-tetrazol-1-yl)benzoate (1.46 g, 5.27 mmol) and an aqueous solution of sodium hydroxide (20 mL, 2M, 40 mmol) in methanol/tetrahydrofuran (20 mL/10 mL). After 2 hours, adjust the pH of the reaction mixture to about 2 using a 1M aqueous hydrochloric acid solution. Extract the reaction mixture with ethyl acetate and then dichloromethane. Dry the combined organic layers over MgSO$_4$, filter, and evaporate in vacuo to give a the title compound: R$_f$=0.55 (silica gel, 85% chloroform/10% methanol/5% acetic acid).

EXAMPLE 51

(S)-N-Methyl-N-(4-(4-(1-(but-2-en-1-yl)-1H-benzimidazol-2-yl)[1,4]diazepan-1-yl)-2-(4-fluorophenyl)butyl)-2-methoxy-5-(5-trifluoromethyl-1H-tetrazol-1-yl)benzamide

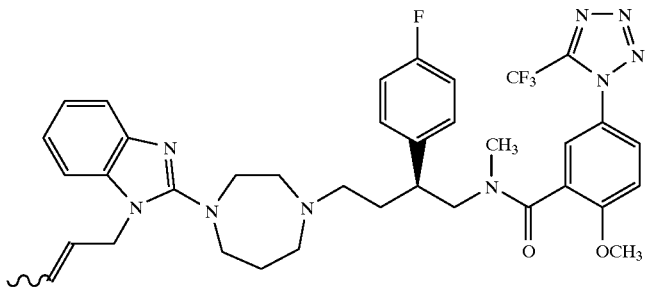

58.1 Synthesis of (S)-N-methyl-N-(2-(4-fluorophenyl)-4-oxobutyl)-2-methoxy-5-(5-trifluoromethyl-1H-tetrazol-1-yl)benzamide Combine N-methyl-2-(4-fluorophenyl)pent-4-enyl)amine (0.2 g, 1.0 mmol) and dichloromethane (10 mL). Add (5-trifluoromethyl-1H-tetrazol-1-yl)benzoic acid (1.0 mmol), 1-hydroxybenzotriazole hydrate (0.16 g, 1.2 mmol), N,N-diisopropylethylamine (0.17 mL, 1.0 mmol), and 1-ethyl-3-(3-dimethylaminopropyl)carbodiimide hydrochloride (0.23 g, 1.2 mmol). After 18 hours, dilute the reaction mixture with ethyl acetate and extract with brine. Dry the organic layer over Na$_2$SO$_4$, filter, and evaporate in vacuo to give a residue. Chromatograph the residue on silica gel to give (S)-N-methyl-N-(2-(4-fluorophenyl)pent-4-enyl)-2-methoxy-5-(5-trifluoromethyl-1H-tetrazol-1-yl) benzamide.

Combine (S)-N-methyl-N-(2-(4-fluorophenyl)pent-4-enyl)-2-methoxy-5-(5-trifluoromethyl-1H-tetrazol-1-yl) benzamide (10 mmol), acetone/t-butanol/water (2/1/1, 56 mL), and a solution of N-methylmorpholine N-oxide (2.6 mL, 50% in water, 12.7 mmol). Add a solution of osmium tetraoxide (2.6 mL, 4% in water, 0.44 mmol). After 3 hours, evaporate in vacuo to remove most of the acetone and partition the evaporated reaction mixture between dichloromethane and an aqueous 10% solution of sodium thiosulfate. Separate the layer, dry the organic layer over MgSO$_4$, filter, and evaporate in vacuo to give a residue. Combine the residue, tetrahydrofuran (70 mL), and water (17.5 mL). Add sodium meta-periodate (3.2 g). After 1.5 hours, filter the reaction mixture, rinse the solids with dichloromethane, and evaporate the filtrate give the title compound.

58.2 Synthesis of ((S)-N-methyl-N-(4-(4-1-(but-2-en-1-yl)-1H-benzimidazol-2-yl)[1,4]diazepan-1-yl)-2-(4-fluorophenyl)butyl)-2-methoxy-5-(5-trifluoromethyl-1H-tetrazol-1-yl)benzamide Prepare by the method of Example 43.1 using (S)-N-methyl-N-(2-(4-fluorophenyl)-4-oxobutyl)-2-methoxy-5-(5-trifluoromethyl-1H-tetrazol-1-yl)benzamide and 4-(1-(but-2-en-1-yl))-1H-benzimidazol-2-yl)[1,4]diazepane hydriodic acid salt to give the title compound.

The tachykinins are a class of neuropeptides which share a common C-terminus sequence, Phe-Xaa-Gly-Leu-Met-NH$_2$. The tachykinins are widely distributed in the peripheral and central nervous systems where they bind to at least three receptor types. Among the tachykinin receptors, the NK$_1$, NK$_2$, and NK$_3$ receptors are defined by the preferred binding affinity of substance P, neurokinin A (NKA), and neurokinin B (NKB), respectively.

The use of tachykinin antagonists is indicated as therapy for a variety of tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis.

It is understood that tachykinin-mediated diseases and conditions are those diseases and conditions in which the tachykinins are involved, either in whole or in part, in their clinical manifestation(s). Moreover, the tachykinins involvement is not necessarily causative of a particular tachykinin-mediated disease and condition. Tachykinin antagonists are useful in controlling or providing therapeutic relief of those tachykinin-mediated diseases and conditions.

The present invention provides new and useful tachykinin antagonists of formula (1) or stereoisomers or pharmaceutically acceptable salts thereof.

In a further embodiment, as tachykinin antagonists the present invention provides a method of treating tachykinin-mediated diseases and conditions, including: hypersensitivity reactions; adverse immunological reactions; asthma; bronchitis; allergic rhinitis, including seasonal rhinitis and sinusitis; allergies; contact dermatitis; atopic dermatitis; inflammatory bowel diseases, including Crohn's disease and ulcerative colitis; and emesis in a patient in need thereof comprising administering to said patient a therapeutically effective amount of a compound of formula (1).

Immediate hypersensitivity can occur when an IgE antibody response is directed against innocuous antigens, such as pollen. During such a response there is generally a subsequent release of pharmacological mediators, such as histamine, by IgE-sensitized mast cells resulting in an acute inflammatory reaction. The characteristics of the response are determined by the tissue in which the reaction occurs and gives rise to allergic diseases including: allergic rhinitis, including seasonal rhinitis and sinusitis; pulmonary diseases, such as asthma; allergic dermatisis, such as urticaria, angioedema, eczema, atopic dermatisis, and contact dermatitis; gastrointestinal allergies, such as those caused by food or drugs; cramping; nausea; vomiting; diarrhea; ophthalmic allergies; and uveitis.

Histamine, producing its effects via activation of the H$_1$ receptor, is an important mediator of the above responses involved in immediate hypersensitivity. In the acute phase of allergic rhinitis, histamine $H_1$ receptor antagonists have been shown to effectively inhibit the nasal itchiness, rhinorrhea, and sneezing associated with that condition. However, histamine $H_1$ receptor antagonists are less effective in relieving nasal congestion. The acute response to allergen in rhinitis is often followed by a chronic inflammatory response during which the inflamed mucosa becomes hypersensitive to both antigirritants. Histamic irritants. Histamine $H_1$ receptor antagonists are also ineffective in attenuating the symptoms of the chronic phase of the response.

The present invention provides new and useful histamine antagonists of formula (1) or stereoisomers or pharmaceutically acceptable salts thereof.

In a further embodiment, as histamine antagonists the present invention provides a method of treating allergic diseases, including: allergic rhinitis, including seasonal rhinitis and sinusitis; pulmonary diseases, such as asthma; allergic dermatosis, such as urticaria, angioedema, eczema, atopic dermatitis, and contact dermatitis; allergic conjuctivitis; gastrointestinal allergies, such as those caused by food or drugs; cramping; nausea; vomiting; diarrhea; and ophthalmic allergies and uveitis; in a patient in need thereof comprising administering to said patient a therapeutically effective amount of a compound of formula (1).

In addition to histamine, the tachykinins, particularly substance P, are also important contributors to the allergic response and produce some symptoms distinct from those produced by a histamine response. This occurs because sensory nerves of trigeminal origin, located around blood vessels and within the nasal mucosal lining, upon stimulation by irritants or inflammatory mediators, such as histamine, will release tachykinins.

Patients with allergic rhinitis have been shown to have higher nasal levels of substance P when their rhinitis symptoms are present. Mosimann et al. *J. Allergy Clin. Immunol.* 92, 95 (1993); Takeyama et al., *J. Pharm. Pharmacol.* 46, 41 (1994); and Wantanabe et al., *Ann. Otol. Rhinol. and Larynaol.*, 102, 16 (1993). In humans, topical or intravenous administration of tachykinins induces nasal obstruction, recruitment of inflammatory cells, glandular secretion, and microvascular leakage in allergic rhinitis. The nasal obstruction produced by substance P was found to be $NK_1$ receptor mediated. Braunstein et al., *Am. Rev. Respir. Dis.,* 144, 630 (1991); Devillier et al., *Eur. Respir. J.* 1, 356 (1988). Furthermore, sensory nerve-mediated effects, such as nasal irritability and hyperresponsiveness which occurs in late phase allergic reactions, also result from tachykinin release. Anggard, *Acta Otolarynaol.* 113, 394 (1993). Depletion of tachykinins from nasal sensory nerves after chronic capsaicin administration improved rhinitic symptoms in affected individuals. Lacroix et al., *Clin. and Exper. Allergy,* 21, 595 (1991).

Antagonism of the effects of histamine on the $H_1$ receptor is useful in the treatment of allergic diseases, such as rhinitis. Likewise, antagonism of the effects of the tachykinins, particularly substance P on its preferred receptor, is useful in the treatment of symptoms which are concurrent with allergic diseases. Therefore, the potential benefits of an antagonist with affinity at both the $H_1$ and $NK_1$ receptors would be to reduce or prevent clinical manifestations of allergic diseases which are mediated through both receptors.

More particularly, the present invention provides new and useful compounds of formula (1) or stereoisomers or pharmaceutically acceptable salts thereof which are both tachykinin antagonists and histamine antagonists.

In a further embodiment, as both tachykinin antagonists and histamine antagonists the present invention provides a method of treating allergic diseases, including: allergic rhinitis, including seasonal rhinitis and sinusitis; contact dermatitis; allergic conjuctivitis; gastrointestinal allergies, such as those caused by food or drugs; cramping; nausea; vomiting; diarrhea; and ophthalmic allergies and uveitis; and inflammatory bowel diseases, including Crohn's diseases and ulcerative colitis; in a patient in need thereof comprising administering to said patient a therapeutically effective amount of a compound of formula (1).

Various diseases and conditions described to be treated herein, are well known and appreciated by those skilled in the art. It is also recognized that one skilled in the art may affect the associated diseases by treating a patient presently afflicted with the diseases or by prophylactically treating a patient afflicted with the diseases with a therapeutically effective amount of the compounds of formula (1).

As used herein, the term "patients" refers to a warm blooded animal such as a mammal which is afflicted with a particular allergic disease. It is understood that guinea pigs, dogs, cats, rats, mice, horses, cattle, sheep, and humans are examples of animals within the scope of the meaning of the term.

As used herein, the term "therapeutically effective amount" of a compound of formula (1) refers to an amount which is effective in controlling the diseases described herein. The term "controlling" is intended to refer to all processes wherein there may be a slowing, interrupting, arresting, or stopping of the progression of the diseases described herein, but does not necessarily indicate a total elimination of all disease symptoms, and is intended to include prophylactic treatment of the diseases.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are able to be determined by one skilled in the art.

In effecting treatment of a patient afflicted with diseases described above, a compound of formula (1) can be administered in any form or mode which makes the compound bioavailable in an effective amount, including oral, inhalation, and parenteral routes. For example, compounds of formula (1) can be administered orally, by inhalation of an aerosol or dry powder, subcutaneously, intramuscularly, intravenously, transdermally, intranasally, rectally, occularly, topically, and the like. Oral, inhalation, topical, or occular administration is generally preferred for treatment of allergic diseases. Oral, inhalation, or occular administration is more preferred for treatment of allergic diseases. One skilled in the art of preparing formulations can readily select the proper form and mode of administration depending upon the particular characteristics of the compound selected, the disease or condition to be treated, the stage of the disease or condition, and other relevant circumstances. (Remington's Pharmaceutical Sciences, 18th Edition, Mack Publishing Co. (1990)).

The compounds o f the present invention can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, such as acid addition salts or base addition salts, for purposes of stability, convenience of crystallization, increased solubility, and the like.

In another embodiment, the present invention provides pharmaceutical compositions comprising a therapeutically effective amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by someone skilled in the art.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the compound of formula (1) present in such compositions is such that a suitable dosage will be obtained. Preferred compositions and preparations are able to be determined by one skilled in the art.

The compounds of the present invention may also be administered by inhalation, such as by aerosol or dry powder. Delivery may be by a liquefied or compressed gas or by a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The compounds of the present invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula (1) or its pharmaceutical salt from about 0.1 to about 10% w/v (weight per unit volume).

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE A

Antagonism of [$^3$H]-pyrilamine binding to histamine $H_1$ receptors by putative antagonists One skilled in the art can measure the $H_1$ receptor affinity of proposed histamine antagonists as evaluated in rat brains or Chinese hamster ovary cells transfected with the human histamine $H_1$ receptor gene (CHOpcDNA3H1R cells).

For the studies in rat brain, young male rats are sacrificed by decapitation and the brains are immediately removed. The cortici are dissected and used immediately or stored at −20° C. For the studies in Chinese hamster ovary cells, confluent cells are freshly scraped from culture flasks. The tissues or cells are homogenized with a Polytron (setting no. 6 for 15 seconds) in 20 mL of 50 mM potassium sodium phosphate (pH 7.4, at 4° C.). The homogenate is centrifuged at 48,000×g for 12 minutes at 4° C. The pellet is resuspended using a Polytron (setting no. 6 for 15 seconds) in incubation buffer (50 mM potassium sodium phosphate, pH 7.4, at ambient temperature, containing 0.1% bovine serum albumin) to a concentration of 40 mg/mL and is immediately added to tubes to start the assay. The protein content of the crude membrane suspension can be determined by the method of O. H. Lowery et al., *J. Biol. Chem.*, 193 265 (1951).

The binding assay is carried out in duplicate in 12×75 mm polypropylene tubes in 50 mM potassium sodium phosphate (pH 7.4, at ambient temperature) containing 0.1% bovine serum albumin. The radioligand, [$^3$H]-pyrilamine, is diluted in incubation buffer to a concentration of 2 nM and added to each tube (50 µL). The test compound is diluted in incubation buffer ($10^{-10}$ M to $10^{-5}$ M) and is added to the appropriate tubes (50 µL). The assay is started by the addition of 250 µL of well mixed tissue suspension. The final incubation volume is 0.5 mL. The assay is carried out at ambient temperature for 30 minutes. The incubation is terminated by the addition of 3.5 mL of 0.9% sodium chloride solution (4° C.) and filtration through GF/B filters that have been presoaked overnight in 0.1% polyethyleneimine, using a Brandel cell harvester. The filters are rapidly washed with two 3.5 mL portions of incubation buffer and transferred to scintillation vials. Ecolume (9 mL) is added the vials. The vials are shaken and allowed to set for 4 hours before being counted by liquid scintillation spectrometry. Specific binding is determined as the difference between tubes containing no test compound and the tubes containing 10 µM promethazine. Total membrane bound radioactivity is generally about 5% of that added to the tubes. Specific binding is generally 75% to 90% of total binding as determined by the method of M. D. DeBacker et al., *Biochem. and Biophys. Res. Commun.*, 197(3) 1601 (1991). The molar concentration of compound that causes 50% inhibition of ligand binding at the screening dose (10 µM) is the $IC_{50}$ value, and is expressed as the cumulative mean (±S.E.M.) for n separate experiments.

EXAMPLE B

Antagonism of iodinated tachykinin binding to $NK_1$ receptors by putative antagonists One skilled in the art can measure the $NK_1$ receptor affinity of proposed tachykinin antagonists as evaluated in guinea pig lungs (Keystone Biologicals, Cleveland, Ohio). Tissues are homogenized with a Polytron in 15 volumes of 50 mM Tris-HCl buffer (pH 7.4, 4° C.) and centrifuged. The pellet is resuspended in Tris-HCl buffer and centrifuged; the pellet is washed twice by resuspension. The final pellet is resuspended at a concentration of 40 mg/ml in incubation buffer and remains at room temperature for at least 15 min prior to use. Receptor binding is initiated by addition of 250 µl membrane preparation in duplicate to 0.1 nM of $^{125}$I-Bolton Hunter Lys-3 labeled substance P in a final volume of 500 µl of buffer containing 50 mM Tris-HCl (pH 7.4 at room temperature), 0.1% bovine serum albumin, 2 mM manganese chloride, 40 µg/ml bacitracin, 4 µg/ml leupeptin and chymostatin, 1 µM thiorphan and various doses of the putative tachykinin antagonists. Incubations are performed at room temperature for 90 min; binding is terminated by addition of 50 mM Tris-HCl buffer (pH 7.4, 4° C.) and filtration under vacuum through GF/B filters presoaked with 0.1% polyethyleneimine. Filter bound radioactivity is quantitated in a gamma counter. Nonspecific binding is defined as binding in the presence of 1 µM substance P.

Specific binding is calculated by subtracting nonspecific binding from total binding. Competition of iodinated substance P binding by test compounds or standards is expressed as a percentage of this maximum competition. $IC_{50}$ values (concentration required to inhibit 50% of receptor binding) are generated for each of the test compounds by nonlinear regression using an iterative curve fitting program (GraphPAD Inplot, San Diego, Calif.).

EXAMPLE C

Histamine ($H_1$) antagonism in guinea pig ileum

One skilled in the art can determine that the compounds of the present invention are $H_1$ receptor antagonists in vitro by evaluating the compound's ability to inhibit histamine mediated smooth muscle contraction. Male Hartley guinea pigs, weighing 200–450 grams, are sacrificed by $CO_2$ asphyxiation. A piece of ileum, about 20 cm in length, is removed and cut into 2 cm pieces. Each ileum piece is placed in an organ bath at 37° C. containing Tyrode's solution and is constantly aerated with 95% $O_2$/5% $CO_2$. Tyrode's solution has the composition: sodium chloride 136.9 mM, potassium chloride 2.68 nM, calcium chloride 1.8 mM, sodium dihydrogen phosphate 0.42 mM, sodium bicarbonate 11.9 mM, and dextrose 5.55 mM. Contractions are measured with an isometric transducer (Grass FTO3C), and are recorded on a polygraph recorder and/or a computer. The ileum strips are loaded with 1.0 grams of tension and allowed to equilibrate for a minimum of 30 minutes before starting the experiments. Tissues are preincubated with vehicle or varying concentrations of test compound followed by histamine challenge.

A competitive $H_1$ receptor antagonist produces a parallel shift of the histamine dose-response curve to the right without a depression of the maximal response. The potency of the antagonism is determined by the magnitude of the shift and is expressed as a $pA_2$ value which is the negative logarithm of the molar concentration of antagonist which produces a two-fold shift of the dose response curve to the right. The $pA_2$ value is calculated by using Schild analysis. O. Arunlakshana and H. O. Schild, *Br. J. Pharmacol Chemother.* 14, 48–58 (1958). When the slope of the lines obtained by a Schild analysis are not significantly different from one (1) the compound is acting as a competitive antagonist.

EXAMPLE D

Antagonism of tachykinin-induced phosphatidylinositol (PI) turnover in vitro by putative antagonists One skilled in the art can determine $NK_1$ receptor antagonism by measuring the substance P-induced phosphatidylinositol (PI, inositol phosphate) accumulation in UC11 cells in the presence and absence of $NK_1$ receptor antagonists. Cells are seeded onto 24-well plates at 125,000 cells/well, two or three days prior to the assay. Cells are loaded with 0.5 mL of 0.2 µM myo-[2-$^3$H(N)] inositol (American Radiolabeled Chemicals Inc., specific activity; 20 µCi/mmol) 20–24 hours prior to the assay. Cultured cells are maintained at 37° C. in 5% $CO_2$ environment.

On the day of the assay, media is aspirated and the cells incubated in RPMI-1640 media containing 40 µg/ml bacitracin, 4 µg/ml each of leupeptin and chymostatin, 0.1% bovine serum albumin, 10 µM thiorphan, and 10 mM lithium chloride. After 15 minutes, the test compound is added to the cells in a volume of 0.1 mL. After another 15 min, substance P is added to UC11 cells at various concentrations to start the reaction followed by incubation for 60 min at 37° C. in 5% $CO_2$ environment in a final volume of 1 mL. To terminate the reaction, the media is aspirated and methanol (0.1 mL) is added to each well. Two aliquots of methanol (0.5 mL) are added to the wells to harvest the cells into chloroform resistant tubes. Chloroform (1 mL) is added to each tube followed by doubly distilled water (0.5 mL). Samples are vortexed for 15 seconds and centrifuged at 1700×g for 10 minutes. An aliquot (0.9 mL) of the aqueous (top) phase is removed and added to doubly distilled water (2 mL). The mixture is vortexed and loaded onto a 50% Bio-Rad AG 1-X8 (formate form, 100–200 mesh) exchange column (Bio-Rad Laboratories, Hercules, Calif.). The columns are washed, in order, with: 1) 10 ml doubly distilled water, 2) 5 mL of 5 mM disodium tetraborate/60 mM sodium formate, and 3) 2 mL of 1 M ammonium formate/0.1 M formic acid. The third elution is collected and counted in 9 mL scintillation fluid. A 50 $\mu l$ aliquot of the organic (bottom) phase is removed, dried in a scintillation vial and counted in 7 mL scintillation fluid. The ratio of DPM in the aqueous phase aliquot (total inositol phosphates) to the DPM in the 50 $\mu l$ organic phase aliquot (total [$^3$H] inositol incorporated) is calculated for each sample. Data are expressed as a percent of agonist-induced accumulation of [$^3$H]-inositol phosphates over basal levels. The ratios in the presence of test compound and/or standards are compared to the ratios for control samples (i.e. no stimulating agonist).

Dose-response graphs are constructed and the ability of the test compounds to inhibit tachykinin-induced phosphatidyinositol turnover determined with the aid of a computer program. Data is expressed as percent stimulation of total inositol phosphate accumulation over basal levels and normalized to the maximum response produced by substance P. Schild analysis is performed using dose response curves to obtain a value indicative of the strength of a competitive antagonist and is expressed as the $pA_2$, which is the negative logarithm of the molar concentration of antagonist which reduces the effect of a dose of agonist to one-half of that expected at the dose of agonist. The slope of the lines obtained by a Schild analysis are not significantly different from one (1) the compound is acting as a competitive antagonist.

EXAMPLE E

Evaluation of $H_1$ (or $NK_1$) antagonism in vivo

One skilled in the art can determine that the compounds of the present invention mediate the immediate hypersensitivity response in vivo by evaluating the ability of the compounds to inhibit the formation of histamine (or substance P) induced wheals in guinea pigs. Animals are anesthetized with pentobarbitol (i.p.). Dorsal skin is shaved and intradermal injections of histamine (or substance P) are given in the shaved area at appropriate times after the administration of the test compounds. Doses, routes, and times of administration may vary according to experimental design. The design of such experiments is well known and appreciated in the art. Immediately after the intradermal challenges, the animal is given an intravenous injection of 1% Evan's blue dye to make the wheals visible. At an appropriate time after the challenge the animals are sacrificed by $CO_2$ inhalation. The skin is removed and the diameter of each wheal is measured in two perpendicular directions.

The wheal response is used an the index of the edema response. The percent of inhibition of the wheal response is calculated by comparing the drug-treated group to a vehicle-treated group. Linear regression of the dose-response inhibition curve is used to determine an $ED_{50}$ value, expressed in mg/kg, which is the dose of compound which inhibits histamine-induced skin wheal by 50%.

EXAMPLE F

Evaluation of $NK_1$ antagonism in vivo

One skilled in the art can also determine that the compounds of the present invention are $NK_1$ receptor antagonists in vivo by evaluating the compound's ability to inhibit substance P-induced plasma protein extravasation in guinea pig trachea. Substance P-induced protein leakage through postcapillary venules is assessed by measuring Evans Blue dye accumulation in guinea pig trachea.

When putative antagonists are administered intravenously, animals are anesthetized with pentobarbitol then injected with Evans Blue dye (20 mg/kg, i.v., prepared in 0.9% sodium chloride solution). One minute after dye administration, the antagonist is administered (i.v.) followed by substance P (0.3 nmole/kg, i.v.) and, after 5 min, excess dye removed from the circulation by transcardiac perfusion with 50 ml 0.9% sodium chloride solution. The trachea and primary bronchi are removed, blotted dry and weighed.

When the putative antagonist is administered orally, one hour after dosing the animals are anesthetized with pentobarbitol one hour after dosing and injected with Evans Blue dye (20 mg/kg, i.v., prepared in 0.9% sodium chloride solution). One minute after dye administration, substance P (0.3 nmole/kg, i.v.) is administered and, after 5 min, excess dye removed from the circulation by transcardiac perfusion with 50 ml 0.9% sodium chloride solution. The trachea and primary bronchi are removed, blotted dry and weighed.

Dye quantitation is performed spectrophotometrically (620 nm) after extracting tissues in formamide for 24 hr at 50° C. Values are subtracted from background (dye only, no agonist). $ED_{50}$ (dose of compound which inhibits substance P-induced plasma protein extravasation by 50%) is calculated from linear regression analysis.

What is claimed is:

1. A compound of the formula

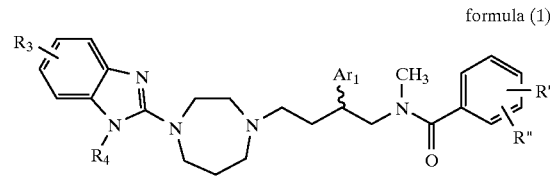

formula (1)

wherein

R' is from 1 to 3 substituents each independently chosen from the group consisting of hydrogen, halogen, —$OCF_3$, $C_1$–$C_6$ alkyl, and $C_1$–$C_6$ alkoxy;

R" is hydrogen or a radical chosen from the group consisting of

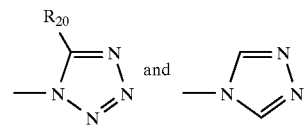

wherein $R_{20}$ is selected from the group consisting of hydrogen, $C_1$–$C_4$ alkyl, and —$CF_3$;

$R_3$ is from 1 to 3 substituents each independently chosen from the group consisting of hydrogen, halogen, $C_1$–$C_6$ alkyl, and $C_1$–$C_6$ alkoxy;

$Ar_1$ is a radical chosen from the group consisting of

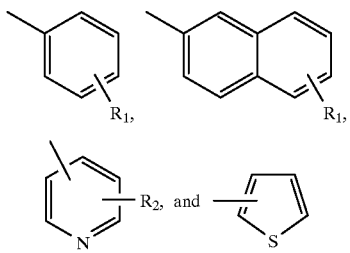

wherein $R_1$ is from 1 to 3 substituents each independently chosen from the group consisting of hydrogen, halogen, hydroxy, $CF_3$, $C_1$–$C_6$ alkyl, and $C_1$–$C_6$ alkoxy;

$R_2$ is from 1 to 2 substituents each independently chosen from the group consisting of hydrogen, halogen, $C_1$–$C_6$ alkyl, and $C_1$–$C_6$ alkoxy;

$R_4$ is chosen from the group consisting of hydrogen, $C_1$–$C_6$ alkyl, —$(CH_2)_w$—O—$(CH_2)_tCO_2R_8$, —$(CH_2)_jCN$, —$(CH_2)_uCO_2R_6$, —$(CH_2)_uC(O)NR_{16}R_{17}$, —$(CH_2)_pAr_2$, —$(CH_2)_w$—O—$R_7$, —$CH_2CF_3$, —$CH_2CH_2CH_2CF_3$, —$(CH_2)_2CH=CH_2$, —$CH_2CH=CH_2$, —$CH_2CH=CHCH_3$, —$CH_2CH=CHCH_2CH_3$, —$CH_2CH=C(CH_3)_2$, and —$(CH_2)_gS(O)_kR_{19}$, wherein w is an integer from 2 to 5;
t is an integer from 1 to 3;
j is an integer from 1 to 5;
u is an integer from 1 to 5;
p is 1 or 2;
g is 2 or 3;
k is an integer from 0, 1, or 2;
$R_6$ is hydrogen or $C_1$–$C_4$ alkyl;
$R_7$ is hydrogen, $C_1$–$C_4$ alkyl, —$(CH_2)_y$—$CF_3$, —$CH_2CN$ or a radical chosen from the group consisting of

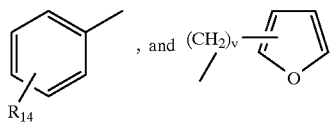

wherein v is an integer from 1 to 3;
y is an integer from 0 to 2;
$R_{14}$ is chosen from the group consisting of hydrogen, halogen, $C_1$–$C_4$ alkyl, and —$CO_2R_{15}$ wherein $R_{15}$ is hydrogen or $C_1$–$C_4$ alkyl;
$R_8$ is hydrogen or $C_1$–$C_4$ alkyl;
$R_{16}$ is hydrogen or $C_1$–$C_4$ alkyl;
$R_{17}$ is hydrogen or $C_1$–$C_4$ alkyl;

$Ar_2$ is a radical chosen from the group consisting of

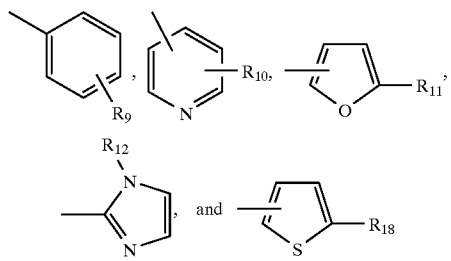

wherein $R_9$ is from 1 to 3 substituents each independently chosen from the group consisting of hydrogen, halogen, $CF_3$, $C_1$–$C_6$ alkyl, $C_1$–$C_6$ alkoxy, and —$CO_2R_{13}$ wherein $R_{13}$ is chosen from the group consisting of hydrogen and $C_1$–$C_4$ alkyl;

$R_{10}$ is from 1 to 2 substituents each independently chosen from the group consisting of hydrogen, halogen, $C_1$–$C_6$ alkyl, and $C_1$–$C_6$ alkoxy;

$R_{11}$ is chosen from the group consisting of hydrogen, —$CH_3$, and —$CH_2OH$;

$R_{12}$ is chosen from the group consisting of hydrogen, $C_1$–$C_4$ alkyl, and benzyl;

$R_{18}$ is chosen from the group consisting of hydrogen, halogen, —$CH_3$, and —$CH_2OH$;

$R_{19}$ is $C_1$–$C_4$ alkyl or a radical of the formula

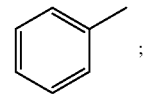;

and stereoisomers, and pharmaceutically acceptable salts thereof.

2. A compound of claim 1 wherein $R_4$ is —$(CH_2)_w$—O—$R_7$ wherein w and $R_7$ are as defined in claim 1.

3. A compound of claim 2 wherein w is 2.

4. A compound of claim 1 wherein $R_4$ is —$(CH_2)_pAr_2$ wherein p and $Ar_2$ are as defined in claim 1.

5. A compound of claim 4 wherein p is 1.

6. A compound of claim 5 wherein $Ar_2$ is fur-2-yl.

7. A compound of claim 5 wherein $Ar_2$ is 5-hydroxymethylfur-2-yl.

8. A compound of claim 5 wherein $Ar_2$ is pyrid-2-yl.

9. A compound of claim 1 wherein $R_4$ is —$CH_2CH=CHCH_3$.

10. A compound of claim 1 wherein the compound is (+)- or (−)-N-Methyl-N-(4-(4-(1-(2-ethoxyethyl)-1H-benzimidazol-2-yl)[1,4]diazepan-1-yl)-2-(4-fluorophenyl)butyl)-3,4,5-trimethoxybenzamide or a mixture thereof.

11. A compound of claim 1 wherein the compound is (+)- or (−)-N-Methyl-N-(4-(4-(1-(5-hydroxymethylfur-2-ylmethyl)-1H-benzimidazol-2-yl)[1,4]diazepan-1-yl)-2-(4-fluorophenyl)butyl)-3,4,5-trimethoxybenzamide or a mixture thereof.

12. A compound of claim 1 wherein the compound is (+)- or (−)-N-Methyl-N-(4-(4-(1-(4-fluorobenzyl)-1H-benzimidazol-2-yl)[1,4]diazepan-1-yl)-2-(4-fluorophenyl)butyl)-2-methoxy-5-(1H-tetrazol-1-yl)benzamide or a mixture thereof.

13. A pharmaceutical composition comprising a compound of claim 1 and a pharmaceutically acceptable carrier.

14. A method for treating allergic rhinitis in a patient in need thereof comprising administering to said patient a therapeutically effective amount of a compound of claim 1.

15. A method for treating asthma in a patient in need thereof comprising administering to said patient a therapeutically effective amount of a compound of claim 1.

16. A method for treating emesis in a patient in need thereof comprising administering to said patient a therapeutically effective amount of a compound of claim 1.

17. A method for treating inflammatory bowel disease in a patient in need thereof comprising administering to said patient a therapeutically effective amount of a compound of claim 1.

18. A method for treating uveitis in a patient in need thereof comprising administering to said patient a therapeutically effective amount of a compound of claim 1.

19. A method for treating ophthalmic allergies in a patient in need thereof comprising administering to said patient a therapeutically effective amount of a compound of claim 1.

* * * * *